(12) United States Patent
Benvenisty

(10) Patent No.: US 11,859,232 B2
(45) Date of Patent: *Jan. 2, 2024

(54) SCREENING FOR CHEMOTHERAPY RESISTANCE IN HUMAN HAPLOID CELLS

(71) Applicant: YISSUM RESEARCH DEVELOPMENT COMPANY OF THE HEBREW UNIVERSITY OF JERUSALEM LTD., Jerusalem (IL)

(72) Inventor: Nissim Benvenisty, Jerusalem (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 1186 days.

This patent is subject to a terminal disclaimer.

(21) Appl. No.: 16/311,130

(22) PCT Filed: Jun. 19, 2016

(86) PCT No.: PCT/IL2016/050644
§ 371 (c)(1),
(2) Date: Dec. 18, 2018

(87) PCT Pub. No.: WO2017/221225
PCT Pub. Date: Dec. 28, 2017

(65) Prior Publication Data
US 2019/0226003 A1  Jul. 25, 2019

(51) Int. Cl.
| | | |
|---|---|---|
| *C12Q 1/02* | (2006.01) | |
| *A61K 31/704* | (2006.01) | |
| *C07H 15/24* | (2006.01) | |
| *C12N 5/0735* | (2010.01) | |
| *C12Q 1/6806* | (2018.01) | |
| *C12Q 1/6886* | (2018.01) | |
| *C12Q 1/686* | (2018.01) | |

(52) U.S. Cl.
CPC ............ *C12Q 1/025* (2013.01); *A61K 31/704* (2013.01); *C07H 15/24* (2013.01); *C12N 5/0606* (2013.01); *C12Q 1/6806* (2013.01); *C12Q 1/686* (2013.01); *C12Q 1/6886* (2013.01); *C12N 2310/20* (2017.05); *C12Q 2600/142* (2013.01)

(58) Field of Classification Search
CPC .............. C12Q 1/025; C12Q 2600/142; C12N 2310/20
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,656,127 A | 4/1987 | Mundy |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 5,451,503 A | 9/1995 | Hogan et al. |
| 5,589,136 A | 12/1996 | Northrup et al. |
| 6,300,063 B1 | 10/2001 | Lipshutz et al. |
| 8,021,867 B2 | 9/2011 | Smith et al. |
| 8,119,381 B2 | 2/2012 | Smith et al. |

(Continued)

FOREIGN PATENT DOCUMENTS

| | | |
|---|---|---|
| CN | 102300578 A | 12/2011 |
| CN | 105112446 A | 12/2015 |

(Continued)

OTHER PUBLICATIONS

Li et al., A tight control of Rif1 by Oct4 and Smad3 is critical for mouse embryonic stem cell stability. Cell Death and Disease (2015) 6, e1588 (Year: 2015).*

(Continued)

*Primary Examiner* — Samuel C Woolwine
*Assistant Examiner* — Catherine Konopka
(74) *Attorney, Agent, or Firm* — The Roy Gross Law Firm, LLC; Roy Gross

(57) ABSTRACT

A method of selecting an agent for treating a disease of a subject is disclosed which includes identifying genes which bring about resistance to a cytotoxic agent in haploid human embryonic stem (ES) cells. Once the gene is identified, the method includes analyzing the sequence and/or expression of the gene in a cell sample of the subject, wherein an alteration in the sequence and/or level of expression of the gene as compared to the sequence and/or expression of the gene in a control sample is indicative that the agent should be ruled out as a monotherapy for treating the disease in the subject.

19 Claims, 23 Drawing Sheets
(21 of 23 Drawing Sheet(s) Filed in Color)
Specification includes a Sequence Listing.

(56) References Cited

U.S. PATENT DOCUMENTS

| | | | |
|---|---|---|---|
| 8,124,369 | B2 | 2/2012 | Smith et al. |
| 8,129,134 | B2 | 3/2012 | Smith et al. |
| 8,133,697 | B2 | 3/2012 | Smith et al. |
| 8,143,015 | B2 | 3/2012 | Smith et al. |
| 8,143,016 | B2 | 3/2012 | Smith et al. |
| 8,148,098 | B2 | 4/2012 | Smith et al. |
| 8,163,514 | B2 | 4/2012 | Smith et al. |
| 8,304,222 | B1 | 11/2012 | Smith et al. |
| 10,961,503 | B2 * | 3/2021 | Egli ............... C12N 5/0612 |
| 2003/0022367 | A1 | 1/2003 | Xu |
| 2014/0342369 | A1 | 11/2014 | Elling et al. |

FOREIGN PATENT DOCUMENTS

| | | | |
|---|---|---|---|
| EP | 2599859 | A1 | 6/2013 |
| WO | 9001069 | A1 | 2/1990 |
| WO | 9215712 | A1 | 9/1992 |
| WO | 9521271 | A1 | 8/1995 |
| WO | 2006040763 | A2 | 4/2006 |
| WO | 2011006145 | A2 | 1/2011 |
| WO | 2012117254 | A1 | 9/2012 |
| WO | WO-2013079670 | A1 * | 6/2013 ........... C12N 5/0606 |
| WO | 2015042570 | A1 | 3/2015 |

OTHER PUBLICATIONS

Wang et al., Genetic Screens in Human Cells Using the CRISPR-Cas9 System. Science (2014), 343: 80-84, and Supplemental Materials (Year: 2014).*

Liao et al., Targeted disruption of DNMT1, DNMT3A and DNMT3B in human embryonic stem cells. Nature Genetics (2015), 47(5): 469-478 and Online Material (Year: 2015).*

Horii et al., Genome engineering of mammalian haploid embryonic stem cells using the Cas9/RNA system. PeerJ (2013), 10.7717, 1-14 (Year: 2013).*

Mullenders and Bernards, Loss-of-function genetic screens as a tool to improve the diagnosis and treatment of cancer. Oncogene (2009), 28: 4409-4420 (Year: 2009).*

Aouida et al., The Human Carnitine Transporter SLC22A16 Mediates High Affinity Uptake of the Anticancer Polyamine Analogue Bleomycin-A5*. The Journal of Biological Chemistry (2010) 285(9): 6275-6284 (Year: 2010).*

Sagi et al., Derivation and differentiation of haploid human embryonic stem cells. Nature (2016), 532: 107-111 and online material (Year: 2016).*

Zhong et al., Generation of human haploid embryonic stem cells from parthenogenetic embryos obtained by microsurgical removal of male pronucleus. Cell Research (2016), 26: 743-746 and Supplemental Material (Year: 2016).*

Pettitt et al., A Genetic Screen Using the PiggyBac Transposon in Haploid Cells Identifies Parp1 as a Mediator of Olaparib Toxicity. PLOS ONE (2013), 8: e61520 (Year: 2013).*

Sagi, et al, Derivation and differentiation of haploid human embryonic stem cells. Nature, 532(7597), 107-111, 2016.

Pettitt et al., A Genetic Screen Using the PiggyBac Transposon in Haploid Cells Identifies Parp1 as a Mediator of Olaparib Toxicity, PLoS One. 2013; 8(4): e61520.

Donnez et al., Principles and Practice of Fertility Preservation, Cambridge University Press 2011, pp. 1-569.

Okabe et al., Development of neuronal precursor cells and functional postmitotic neurons from embryonic stem cells in vitro, Mech Dev., vol. 59, Issue 1, Sep. 1996, pp. 89-102.

Brustle et al., In vitro-generated neural precursors participate in mammalian brain development, Proc. Natl. Acad. Sci. USA, vol. 94, No. 26, pp. 14809-14814, Dec. 1997.

Bottenstein et al., Growth of a rat neuroblastoma cell line in serum-free supplemented medium, Proc Natl Acad Sci U S A. Jan. 1979;76(1):514-7.

Raff et al., A glial progenitor cell that develops in vitro into an astrocyte or an oligodendrocyte depending on culture medium, Nature. Jun. 2-8, 1983;303(5916):390-6.

Liu et al., Embryonic stem cells differentiate into oligodendrocytes and myelinate in culture and after spinal cord transplantation, Proc Natl Acad Sci U S A. May 23, 2000;97(11):6126-31.

Tsai et al., In vivo immunological function of mast cells derived from embryonic stem cells: an approach for the rapid analysis of even embryonic lethal mutations in adult mice in vivo, Proc Natl Acad Sci U S A. Aug. 1, 2000,97(16):9186-90.

Potocnik et al., Hemato-lymphoid in vivo reconstitution potential of subpopulations derived from in vitro differentiated embryonic stem cells, PNAS Sep. 16, 1997; 94 (19); 10295-10300.

Levenberg et al., Endothelial cells derived from human embryonic stem cells, Proc Natl Acad Sci U S A. Apr. 2, 2002;99(7):4391-6.

Kaufman et al., Hematopoietic colony-forming cells derived from human embryonic stem cells, PNAS Sep. 11, 2001 98 (19) 10716-10721.

Maltsev et al., Cardiomyocytes differentiated in vitro from embryonic stem cells developmentally express cardiac-specific genes and ionic currents, Circ Res. Aug. 1994;75(2):233-44.

Fijnvandraat et al., Development of heart muscle-cell diversity: a help or a hindrance for phenotyping embryonic stem cell-derived cardiomyocytes, Cardiovascular Research, vol. 58, Issue 2, May 2003, pp. 303-312.

Sachinidis et al., Cardiac specific differentiation of mouse embryonic stem cells, Cardiovasc Res. May 1, 2003,58(2):278-91.

Stavridis et al., Neural differentiation of mouse embryonic stem cells, Biochem Soc Trans. Feb. 2003;31(Pt 1):45-9.

Wei et al., Abolition of Cyclin-Dependent Kinase Inhibitor p16Ink4a and p21Cip1/Waf1 Functions Permits Ras-Induced Anchorage-Independent Growth in Telomerase-Immortalized Human Fibroblasts, Mol Cell Biol. Apr. 2003; 23(8): 2859-2870.

Trivedi et al., Derivation and immunological characterization of mesenchymal stromal cells from human embryonic stem cells, Exp Hematol. Mar. 2008;36(3):350-9.

Vazin, A Novel Combination of Factors, Termed SPIE, which Promotes Dopaminergic Neuron Differentiation from Human Embryonic Stem Cells, PLoS One. Aug. 12, 2009;4(8)-e6606.

Elkabetz et al., Human ES cell-derived neural rosettes reveal a functionally distinct early neural stem cell stage, Genes Dev. Jan. 15, 2008;22(2):152-65.

Friling et al., Efficient production of mesencephalic dopamine neurons by Lmx1a expression in embryonic stem cells, Proc Natl Acad Sci U S A. May 5, 2009;106(18):7613-8.

Rippon et al., Embryonic Stem Cells as a Source of Pulmonary Epithelium In Vitro and In Vivo, Proc Am Thorac Soc. Aug. 15, 2008; 5(6): 717-722.

Li et al., Specification of motoneurons from human embryonic stem cells, Nat Biotechnol. Feb. 2005,23(2):215-21.

Chambers et al., Highly efficient neural conversion of human ES and iPS cells by dual inhibition of SMAD signaling, Nat Biotechnol. Mar. 2009;27(3):275-80.

Christian et al., Targeting DNA double-strand breaks with TAL effector nucleases, Genetics. Oct. 2010;186(2):757-61.

Kim et al., Hybrid restriction enzymes: zinc finger fusions to Fok I cleavage domain, Proc Natl Acad Sci U S A. Feb. 6, 1996; 93(3): 1156-1160.

Li, A statistical framework for SNP calling, mutation discovery, association mapping and population genetical parameter estimation from sequencing data, Bioinformatics. Nov. 1, 2011; 27(21): 2987-2993.

Mahfouz et al., Compliance to diabetes self-management in rural El-Mina, Egypt, Cent Eur J Public Health. Mar. 2011;19(1):35-41.

Carlson et al., Mindfulness-based interventions for physical conditions: a narrative review evaluating levels of evidence, ISRN Psychiatry Nov. 14, 2012;2012:651583.

Urnov et al., Highly efficient endogenous human gene correction using designed zinc-finger nucleases, Nature. Jun. 2, 2005:435(7042):646-51.

Reyon et al., FLASH assembly of TALENs for high-throughput genome editing, Nat Biotechnol. May 2012;30(5):460-5.

(56) References Cited

OTHER PUBLICATIONS

Cermak et al., Efficient design and assembly of custom TALEN and other TAL effector-based constructs for DNA targeting, Nucleic Acids Res. Jul. 2011;39(12):e82.

Miller et al., A TALE nuclease architecture for efficient genome editing, Nat Biotechnol. Feb. 2011;29(2):143-8.

Zhang et al., Efficient construction of sequence-specific TAL effectors for modulating mammalian transcription, Nat Biotechnol. Feb. 2011;29(2):149-53.

Jinek et al., A programmable dual-RNA-guided DNA endonuclease in adaptive bacterial immunity, Science. Aug. 17, 2012;337(6096):816-21.

Cho et al., Targeted genome engineering in human cells with the Cas9 RNA-guided endonuclease, Nat Biotechnol. Mar. 2013;31(3):230-2.

Cong et al, Multiplex genome engineering using CRISPR/Cas systems, Science. Feb. 15, 2013;339(6121):819-23.

DiCarlo et al., Genome engineering in Saccharomyces cerevisiae using CRISPR-Cas systems, Nucleic Acids Res. Apr. 2013;41(7):4336-43.

Hwang et al., Heritable and Precise Zebrafish Genome Editing Using a CRISPR-Cas System, PLoS One. Jul. 9, 2013;8(7):e68708.

Jinek et al., RNA-programmed genome editing in human cells, Elife. Jan. 29, 2013;2:e00471.

Mali et al., RNA-guided human genome engineering via Cas9, Science. Feb. 15, 2013; 339(6121): 823-826.

Carette et al., Replication-dependent transgene expression from a conditionally replicating adenovirus via alternative splicing to a heterologous splice acceptor site, J Gene Med. Aug. 2005;7(8):1053-62.

Wang et al., A piggyBac transposon-based genome wide library of insertionally mutated Blm-deficient murine ES cells, Genome Res. Apr. 2009; 19(4): 667-673.

Horn et al., Splinkerette PCR for more efficient characterization of gene trap events, Nat Genet. Aug. 2007;39(8):933-4.

Shendure et al., Next-generation DNA sequencing, Nat Biotechnol. Oct. 2008;26(10):1135-45.

Mardis, Next-generation DNA sequencing methods, Annu Rev Genomics Hum Genet. 2008;9:387-402.

Metzker et al., Sequencing technologies—the next generation, Nat Rev Genet. Jan. 2010;11(1):31-46.

Rhead et al., The UCSC Genome Browser database: update 2010, Nucleic Acids Res. Jan. 2010;38(Database issue):D613-9.

Langmead et al., Ultrafast and memory-efficient alignment of short DNA sequences to the human genome, Genome Biology. 2009; 10.

Gogos et al., Detection of single base mismatches of thymine and cytosine residues by potassium permanganate and hydroxylamine in the presence of tetralkylammonium salts, Nucleic Acids Res. Dec. 11, 1990; 18(23): 6807-6814.

Kotecki, et al., "Isolation and Characterization of a Near-Haploid Human Cell Line", Experimental Cell Research, vol. 252, pp. 273-280 (1999).

Schimenti, J., Haploid Embryonic Stem Cells and the Dominance of Recessive Traits, Cell Stem Cell, vol. 9, Issue 6, Dec. 2, 2011, pp. 488-489.

Shi, et al., "Haploid embryonic stem cells: an ideal tool for mammalian genetic analyses", Protein Cell vol. 3, 806-810 (2012).

Wan, et al., "Parthenogenetic haploid embryonic stem cells produce fertile mice", Cell Research vol. 23, 1330-1333 (2013).

Leeb, et al., "Genetic Exploration of the Exit from Self-Renewal Using Haploid Embryonic Stem Cells", Cell Stem Cell, vol. 14, Issue 3, Mar. 6, 2014, pp. 385-393.

Essletzbichler, et al., "Megabase-scale deletion using CRISPR/Cas9 to generate a fully haploid human cell line", Genome Research, Dec;24(12):2059-65 (2014).

Wutz, A., "Haploid animal cells", Development, vol. 141: 1423-1426 (2014).

Dixon, et al., "Human Haploid Cell Genetics Reveals Roles for Lipid Metabolism Genes in Nonapoptotic Cell Death", ACS Chemical Biology, vol. 10, Issue 7, 1604-1609, Publication Date: May 12, 2015.

Blomen, et al., "Gene essentiality and synthetic lethality in haploid human cells", Science, vol. 350, Issue 6264, pp. 1092-1096 Publication Date: Nov. 27, 2015.

Monfort, et al., "Identification of Spen as a Crucial Factor for Xist Function through Forward Genetic Screening in Haploid Embryonic Stem Cells", Cell Reports, vol. 12, Issue 4, Jul. 28, 2015, pp. 554-561.

Kimura, et al., "CRISPR/Cas9-mediated reporter knock-in in mouse haploid embryonic stem cells", Science Reports vol. 5, 10710 (2015).

Zhong, et al., "CRISPR-Cas9-Mediated Genetic Screening in Mice with Haploid Embryonic Stem Cells Carrying a Guide RNA Library", Cell Stem Cell, vol. 17, Issue 2, Aug. 6, 2015, pp. 221-232.

Horii, et al., "Genome Editing Using Mammalian Haploid Cells", International Journal of Molecular Sciences, vol. 16, 23604-23614 (2015).

Witten Opinion of the International Searching Authority PCT/IL2016/050644 dated Feb. 16, 2017 9 pages.

Wenying Deng et al., "Decreased expression of PinX1 protein predicts poor prognosis of 4 colorectal cancer patients receiving 5-FU adjuvant chemotherapy", Biomedicine & Pharmacotherapy, vol. 73, Jul. 1, 2015, pp. 1-5.

Dong, Qian, "The telomere/telomerase binding factor PinX1 is a new target to improve the radiotherapy effect of oesophageal squamous cell carcinomas", The Journal of Pathology, vol. 229, No. 5, Feb. 22, 2013, pp. 765-774.

S.P. Pitroda et al., "DNA Repair Pathway Gene Expression Score Correlates with Repair Proficiency and Tumor Sensitivity to Chemotherapy", Science Translation Medicine, vol. 6, No. 229, Mar. 26, 2014, 229ra42, 10 pages.

Pettitt S.J. et al., A Genetic Screen Using the PiggyBac Transposon in Haploid Cells Identifies Parp1 as a Mediator of Olaparib Toxicity, PLoS One vol. 8, No. 4, Apr. 25, 2013, e61520, 10 pages.

Ido, Sagi et al., "Derivation and differentiation of haploid human embryonic stem cells", Nature, vol. 532, No. 7597, Apr. 7, 2016, pp. 107-111.

Yang, et al., Generation of haploid embryonic stem cells from Macaca fascicularis monkey parthenotes. Cell Research, 23(10), 1187-1200 (2013).

Wutz, Haploid Mouse Embryonic Stem Cells: Rapid Genetic Screening and Germline Transmission. Annual Review of Cell and Developmental Biology, 30(1), 705-722 (2014).

Tarkowski, et al., Experimental Parthenogenesis in the Mouse. Nature, 226(5241), 162-165 (1970).

Kaufman, et al., Establishment of pluripotential cell lines from haploid mouse embryos. J. Embryol. Exp. Morphol. Feb. 1983;73:249-61.

Egli, et al. Impracticality of egg donor recruitment in the absence of compensation. Cell Stem Cell. Oct. 4, 2011;9(4):293-4.

Leeb, et al., Haploid genomes illustrate epigenetic constraints and gene dosage effects in mammals. Epigenetics Chromatin 6, 41 (2013).

Tesar, et al. New cell lines from mouse epiblast share defining features with human embryonic stem cells. Nature. Jul. 12, 2007;448(7150):196-9.

Revazova, et al. Patient-specific stem cell lines derived from human parthenogenetic blastocysts. Cloning Stem Cells 2007 Fall;9(3):432-49.

Kim, et al. Recombination signatures distinguish embryonic stem cells derived by parthenogenesis and somatic cell nuclear transfer. Cell Stem Cell. Sep. 13, 2007;1(3):346-52.

Paul, et al. Nuclear genome transfer in human oocytes eliminates mitochondrial DNA variants. Nature 493, 632-7 (2013).

Leeb, et al. Germline potential of parthenogenetic haploid mouse embryonic stem cells. Development. Sep. 2012;139(18):3301-5.

Takahashi, et al. Induction of the G2/M transition stabilizes haploid embryonic stem cells. Development. Oct. 2014; 141(20):3842-7.

(56) References Cited

OTHER PUBLICATIONS

Ben-David, et al., Immunologic and chemical targeting of the tight-junction protein Claudin-6 eliminates tumorigenic human pluripotent stem cells. Nat Commun. 2013;4:1992.
Silva, et al., X-chromosome inactivation and epigenetic fluidity in human embryonic stem cells. Proc. Natl. Acad. Sci. U. S. A. 105, 4820-5 (2008).
Bruck, et al., Human pluripotent stem cells with distinct X inactivation status show molecular and cellular differences controlled by the X-Linked ELK-1 gene. Cell Rep. Jul. 25, 2013;4(2):262-70.
Loven, et al. Revisiting global gene expression analysis. Cell. Oct. 26, 2012;151(3):476-82.
McGrath, J. et al., Completion of mouse embryogenesis requires both the maternal and paternal genomes. Cell. May 1984;37(1):179-83.
Barton, et al., Role of paternal and maternal genomes in mouse development. Nature. Sep. 27-Oct. 3, 1984;311(5984):374-6.
Mai, et al. Derivation of human embryonic stem cell lines from parthenogenetic blastocysts. Cell Res. Dec. 2007;17(12):1008-19.
Stelzer, et al., Global analysis of parental imprinting in human parthenogenetic induced pluripotent stem cells. Nat Struct Mol Biol. Jun. 2011;18(6):735-41.
Minkovsky, et al., Concise review: Pluripotency and the transcriptional inactivation of the female Mammalian X chromosome. Stem Cells. Jan. 2012;30(1):48-54.
Biancotti, et al. The in vitro survival of human monosomies and trisomies as embryonic stem cells. Stem Cell Res. Nov. 2012;9(3):218-24.
Zhou, et al. HIF1α induced switch from bivalent to exclusively glycolytic metabolism during ESC-to-EpiSC/hESC transition. EMBO J. May 2, 2012; 31(9): 2103-2116.
Shuai, et al. Durable pluripotency and haploidy in epiblast stem cells derived from haploid embryonic stem cells in vitro. J Mol Cell Biol. Aug. 2015;7(4):326-37.
Carette et al. Haploid genetic screens in human cells identify host factors used by pathogens. Science. Nov. 27, 2009;326(5957):1231-5.
Carette, et al. Ebola virus entry requires the cholesterol transporter Niemann-Pick C1. Nature. Sep. 15, 2011; 477(7364): 340-343.
Wang, et al., Genetic screens in human cells using the CRISPR-Cas9 system. Science. Jan. 3, 2014;343(6166):80-4.
Shalem, et al. Genome-scale CRISPR-Cas9 knockout screening in human cells. Science. Jan. 3, 2014;343(6166):84-87.
Noggle, et al. Human oocytes reprogram somatic cells to a pluripotent state. Nature. Oct. 5, 2011;478(7367):70-5.
Cowan, et al., Nuclear reprogramming of somatic cells after fusion with human embryonic stem cells. Science. Aug. 26, 2005;309(5739):1369-73.
Johannesson, et al. Comparable Frequencies of Coding Mutations and Loss of Imprinting in Human Pluripotent Cells Derived by Nuclear Transfer and Defined Factors. Cell Stem Cell. Nov. 6, 2014;15(5):634-42.
Chen, et al. Optimal timing of inner cell mass isolation increases the efficiency of human embryonic stem cell derivation and allows generation of sibling cell lines. Cell Stem Cell. Feb. 6, 2009;4(2):103-6.
Rao, et al., Molecular cytogenetic applications in analysis of the cancer genome. Methods Mol Biol. 2007;383:165-85.
Lonsdale, et al., The Genotype-Tissue Expression (GTEx) project. Nat Genet. Jun. 2013;45(6):580-5.
Yamada, et al. Human oocytes reprogram adult somatic nuclei of a type 1 diabetic to diploid pluripotent stem cells. Nature. Jun. 26, 2014;510(7506):533-6.
Wanet, et al. Mitochondrial remodeling in hepatic differentiation and dedifferentiation. Int J Biochem Cell Biol. Sep. 2014;54:174-85.
Kim, et al. Robust enhancement of neural differentiation from human ES and iPS cells regardless of their innate difference in differentiation propensity Stem Cell Rev Rep. Jun. 2010;6(2):270-81.
Stelzer, et al., Involvement of parental imprinting in the antisense regulation of onco-miR-372-373. Nat Commun. 2013;4:2724.
Wang, et al. Differentiation of hypothalamic-like neurons from human pluripotent stem cells. J Clin Invest. Feb. 2015;125(2):796-808.
Lian, et al. Directed cardiomyocyte differentiation from human pluripotent stem cells by modulating Wnt/β-catenin signaling under fully defined conditions. Nat Protoc. Jan. 2013;8(1):162-75.
Hua, et al. iPSC-derived β cells model diabetes due to glucokinase deficiency. J Clin Invest. Jul. 2013;123(7):3146-53.
Pagliuca, et al. Generation of functional human pancreatic β cells in vitro. Cell. Oct. 9, 2014;159(2):428-39.
Rezania, et al. Reversal of diabetes with insulin-producing cells derived in vitro from human pluripotent stem cells. Nat Biotechnol. Nov. 2014;32(11):1121-33.
Doench, et al. Optimized sgRNA design to maximize activity and minimize off-target effects of CRISPR-Cas9. Nat Biotechnol. Feb. 2016;34(2):184-191.
Cadinanos, et al., Generation of an inducible and optimized piggyBac transposon system. Nucleic Acids Res. 2007;35(12):e87.
Wang, et al. Chromosomal transposition of PiggyBac in mouse embryonic stem cells. Proc Natl Acad Sci U S A. Jul. 8, 2008;105(27):9290-5.
Chen, et al. Transposon activation mutagenesis as a screening tool for identifying resistance to cancer therapeutics. BMC Cancer. Feb. 27, 2013;13:93.
Deng et al., Decreased expression of PinX1 protein predicts poor prognosis of colorectal cancer patients receiving 5-FU adjuvant chemotherapy, Biomed Pharmacother. Jul. 2015;73:1-5.
Pitroda et al., DNA Repair Pathway Gene Expression Score Correlates with Repair Proficiency and Tumor Sensitivity to Chemotherapy, Sci Transl Med. Mar. 26, 2014;6(229):229ra42.
International Search Report PCT/IL2016/050644 Completed Feb. 8, 2017; dated Feb. 16, 2017 5 pages.
"PinX1 suppresses the proliferation of gastric carcinoma cells and enhances the sensitivity of gastric carcinoma cells to 5-Fluorouracil through Mad1/c-Myc pathway" Chinese Doctoral Dissertations & Master's Theses Full-text Database, 2010, Abstract.
Borrensen et al., Constant denaturant gel electrophoresis as a rapid screening technique for p53 mutations, Proc. Nadl. Acad. Sci. USA, ol. 88, pp. 8405-8409, Oct. 1991.
Liu et al., Parameters Affecting the Sensitivities of Dideoxy Fingerprinting and SSCP, PCR Methods Appli., 4:97, 1994.
Turner et al., Typing of Multiple Single Nucleotide Polymorphisms in Cytokine and Receptor Genes Using SNaPshot, Human Immunology 63, 508-513 (2002).
Cashman et al., Population distribution of human flavin-containing monooxygenase form 3: Gene polymorphisms, Drug Metabolism and Disposition vol. 29, No. 12, 1629-3, 2001.
Leushner et al., Automated Mass Spectrometry: A Revolutionary Technology for Clinical Diagnostics, Molecular Diagnosis vol. 5 No. 4, 341-80, 2000.
Sheffield et al., Oligonucleotides Antisense to Catalytic Subunit of Cyclic AMP-Dependent Protein Kinase Inhibit Mouse Mammary Epithelial Cell DNA Synthesis, Experimental Cell Research 192, 307-310 (1991).
White et al., Detecting Single Base Substitutions as Heteroduplex Polymorphisms, Genomics 12, 301-306 (1992).
Grompe et al., Scanning detection of mutations in human ornithine transcarbamoylase by chemical mismatch cleavage, Proc. Nati. Acad. Sci. USA, vol. 86, pp. 5888-5892, Aug. 1989.
Grompe, The rapid detection of unknown mutations in nucleic acids, Nature Geneties vol. 5 Oct. 1993.
Otto et al., Haploids—Hapless or Happening? Science vol. 292, Issue 5526, pp. 2441-2443, 2001.
Hawley et al., "The HOX11 homebox-containing gene of human leukemia immortalizes murine hematopoietic precursors" Oncogene 9, 1-12, 1994.
Syvanen, "Detection of point mutations in human genes by the solid-phase minisequencing method", Clinica Chimica Acta 226, 225-236, 1994.

(56) References Cited

OTHER PUBLICATIONS

Manz et al. "Planar Chips Technology for Miniaturization of Separation Systems: A Developing Perspective in Chemical Monitoring", Adv in Chromatogr 1993; 33:1-66.
Day et al., "High-Throughput Genotyping Using Horizontal Polyacrylamide Gels with Wells Arranged for Microplate Array Diagonal Gel Electrophoresis (MADGE)", Biotechniques. 19: 830-5, 1995.
Stanford et al., Gene Trapping in Embryonic Stem Cells, Methods in Enzymology, vol. 420, pp. 136-162, 2006.
Certo, et al., Coupling endonucleases with DNA end-processing enzymes to drive gene disruption. Nat Methods. Oct. 2012;9(10):973-5.
Haff, et al., Multiplex genotyping of PCR products with MassTag-labeled primers. Nucleic Acids Res. Sep. 15, 1997,25(18):3749-50.
Syvanen, Detection of point mutations in human genes by the solid-phase minisequencing method. Clinica Chimica Acta, 226(2), 225-236 (1994).
Livak, et al A microtiter plate assay for determining apolipoprotein E genotype and discovery of a rare allele. Hum Mutat. 1994;3(4):379-85.
Harju et al., Colorimetric solid-phase minisequencing assay illustrated by detection of alpha 1-antitrypsin Z mutation. Clin Chem. Nov. 1993;39(11 Pt 1):2282-7.
Nyren, et al., Solid Phase DNA Minisequencing by an Enzymatic Luminometric Inorganic Pyrophosphate Detection Assay. Anal Biochem. Jan. 1993;208(1):171-5.
Pastinen, et al., Minisequencing: A Specific Tool for DNA Analysis and Diagnostics on Oligonucleotide Arrays. Genome Res. Jun. 1997;7(6):606-14.
Nickerson, et al., Automated DNA diagnostics using an ELISA-based oligonucleotide ligation assay. Proc Natl Acad Sci U S A. Nov. 1990; 87(22): 8923-8927.
Landegren, et al., Reading Bits of Genetic Information: Methods for Single-Nucleotide Polymorphism Analysis. Genome Res. Aug. 1998;8(8):769-76.
Tyagi, et al., Multicolor molecular beacons for allele discrimination. Nature Biotechnology, Nat Biotechnol. Jan. 1998;16(1):49-53.
Hacia, et al., Detection of heterozygous mutations in BRCA1 using high density oligonucleotide arrays and two-colour fluorescence analysis. Nat Genet. Dec. 1996;14(4):441-7.
Shoemaker, et al., Quantitative phenotypic analysis of yeast deletion mutants using a highly parallel molecular bar-coding strategy. Nat Genet. Dec. 1996;14(4):450-6.
Kozal, et al., Extensive polymorphisms observed in HIV-1 clade B protease gene using high-density oligonucleotide arrays. Nat Med. Jul. 1996;2(7):753-9.
Sosnowski, et al, Rapid determination of single base mismatch mutations in DNA hybrids by direct electric field control. Proc Natl Acad Sci U S A. Feb. 18, 1997; 94(4): 1119-1123.
Conner, et al., Detection of sickle cell beta S-globin allele by hybridization with synthetic oligonucleotides. Proc Natl Acad Sci U S A. Jan. 1983;80(1):278-82.
Abrams, et al., Comprehensive detection of single base changes in human genomic DNA using denaturing gradient gel electrophoresis and a GC clamp. Genomics, Aug. 1990;7(4):463-75.
Sheffield, et al., Attachment of a 40-base-pair G + C-rich sequence (GC-clamp) to genomic DNA fragments by the polymerase chain reaction results in improved detection of single-base changes. Proc Natl Acad Sci U S A. Jan. 1989;86(1):232-6.
Lerman, et al., Computational simulation of DNA melting and its application to denaturing gradient gel electrophoresis. Methods Enzymol. 1987;155:482-501.
Wartell, et al., Detecting base pair substitutions in DNA fragments by temperature-gradient gel electrophoresis. Nucleic Acids Res. May 11, 1990;18(9):2699-705.
Smith, et al., Novel method of detecting single base substitutions in RNA molecules by differential melting behavior in solution. Genomics, Oct. 1988;3(3):217-23.

Scholz et al., Rapid screening for Tp53 mutations by temperature gradient gel electrophoresis: a comparison with SSCP analysis. Hum Mol Genet. Dec. 1993;2(12):2155-8.
Hayashi, PCR-SSCP: a simple and sensitive method for detection of mutations in the genomic DNA. PCR Methods Appl. Aug. 1991;1(1):34-8.
Orita, et al., Rapid and sensitive detection of point mutations and DNA polymorphisms using the polymerase chain reaction. Genomics. Nov. 1989;5(4):874-9.
Orita, et al., Detection of polymorphisms of human DNA by gel electrophoresis as single-strand conformation polymorphisms. Proc Natl Acad Sci U S A. Apr. 1989;86(8):2766-70.
Howell, et al., Dynamic allele-specific hybridization. A new method for scoring single nucleotide polymorphisms. Nat Biotechnol. Jan. 1999;17(1):87-8.
Holland, et al., Detection of specific polymerase chain reaction product by utilizing the 5'→ 3' exonuclease activity of Thermus aquaticus DNA polymerase. Proc Natl Acad Sci U S A. Aug. 15, 1991;88(16):7276-80.
Ren, et al., Straightforward detection of SNPs in double-stranded DNA by using exonuclease III/nuclease S1/PNA system. Nucleic Acids Res. Feb. 24, 2004;32(4):e42.
Latorra, et al., Enhanced allele-specific PCR discrimination in SNP genotyping using 3? locked nucleic acid (LNA) primers. Hum Mutat. Jul. 2003;22(1):79-85.
Abravaya, et al., Molecular Beacons as Diagnostic Tools: Technology and Applications. Clin Chem Lab Med. Apr. 2003;41(4):468-74.
Germer et al., Single-Tube Genotyping without Oligonucleotide Probes, Genome Res. Jan. 1999;9(1):72-8.
Solinas, et al., Duplex Scorpion primers in SNP analysis and FRET applications. Nucleic Acids Res. Oct. 15, 2001; 29(20): e96.
Beaudet et al., Homogeneous Assays for Single-Nucleotide Polymorphism Typing Using AlphaScreen, Genome Res. Apr. 2001;11(4):600-8.
Bell et al., SNPstream UHT: ultra-high throughput SNP genotyping for pharmacogenomics and drug discovery, Biotechniques. Jun. 2002;Suppl:70-2, 74, 76-7.
Curcio, et al., Multiplex high-throughput solid-phase minisequencing by capillary electrophoresis and liquid core waveguide fluorescence detection. Electrophoresis. May 2002;23(10):1467-72.
Sauer, et al., Extension of the GOOD assay for genotyping single nucleotide polymorphisms by matrix-assisted laser desorption/ionization mass spectrometry. Rapid Commun Mass Spectrom. 2003;17(12):1265-72.
Liljedahl, et al., A microarray minisequencing system for pharmacogenetic profiling of antihypertensive drug response, Pharmacogenetics. Jan. 2003;13(1):7-17.
Tonisson, et al., Unravelling Genetic Data by Arrayed Primer Extension. Clin Chem Lab Med. Feb. 2000,38(2):165-70.
O'Meara, et al., SNP typing by apyrase-mediated allele-specific primer extension on DNA microarrays. Nucleic Acids Research, 30(15), pp. 1-8, (2002).
Fan, et al., Parallel Genotyping of Human SNPs Using Generic High-density Oligonucleotide Tag Arrays. Genome Res. Jun. 2000; 10(6): 853-860.
Akula, et al., Utility and Accuracy of Template-Directed Dye-Terminator Incorporation with Fluorescence-Polarization Detection for Genotyping Single Nucleotide Polymorphisms. Biotechniques. May 2002;32(5):1072-6, 1078.
Hsu, et al., Universal SNP Genotyping Assay with Fluorescence Polarization Detection. Biotechniques. Sep. 2001;31(3):560, 562, 564-8.
Gasparini, et al., Analysis of 31 CFTR mutations by polymerase chain reaction/oligonucleotide ligation assay in a pilot screening of 4476 newborns for cystic fibrosis. J Med Screen. 1999;6(2):67-9.
Shi et al., Enabling Large-Scale Pharmacogenetic Studies by High-Throughput Mutation Detection and Genotyping Technologies, Clinical Chemistry Feb. 2001;47(2):164-72.
Rao, et al., Genotyping single nucleotide polymorphisms directly from genomic DNA by invasive cleavage reaction on microspheres. Nucleic Acids Res. Jun. 1, 2003; 31(11): e66.

(56) References Cited

OTHER PUBLICATIONS

Leeb, et al., Derivation of haploid embryonic stem cells from mouse embryos. Nature. Sep. 7, 2011;479(7371):131-4.

Elling, et al., Forward and Reverse Genetics through Derivation of Haploid Mouse Embryonic Stem Cells. Cell Stem Cell. Dec. 2, 2011;9(6):563-74.

Yang, et al., Generation of Genetically Modified Mice by Oocyte Injection of Androgenetic Haploid Embryonic Stem Cells. Cell. Apr. 27, 2012;149(3):605-17.

Li, et al., Androgenetic haploid embryonic stem cells produce live transgenic mice. Nature. Oct. 18, 2012;490(7420):407-11.

Li, et al., Genetic Modification and Screening in Rat Using Haploid Embryonic Stem Cells. Cell Stem Cell. Mar. 6, 2014;14(3):404-14.

\* cited by examiner

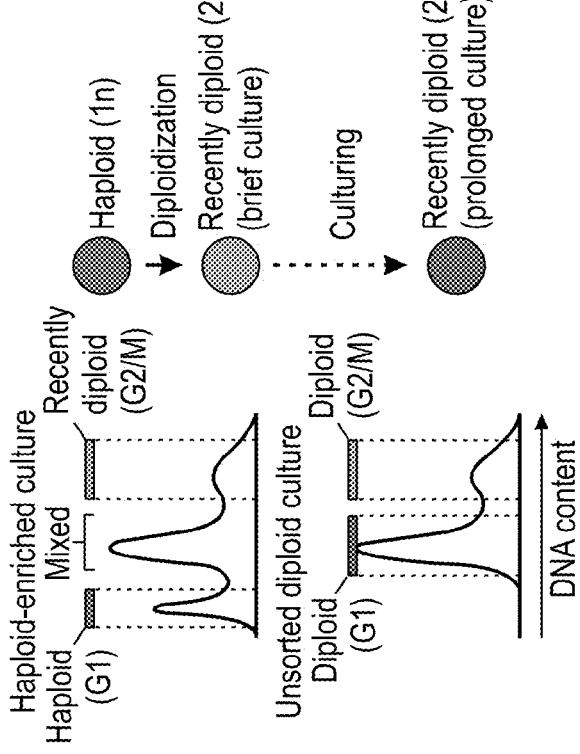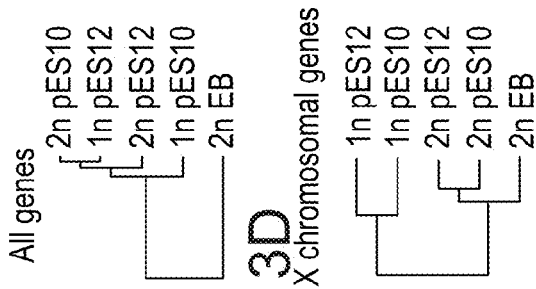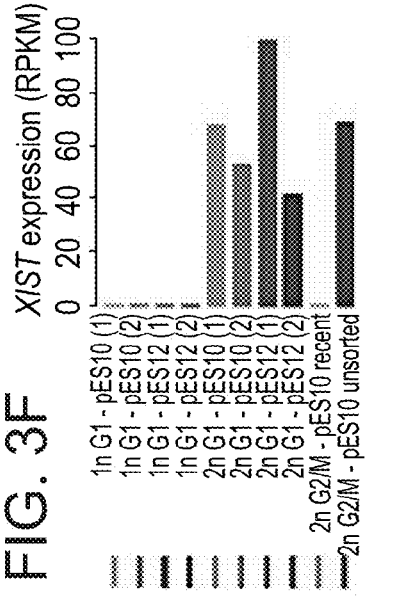

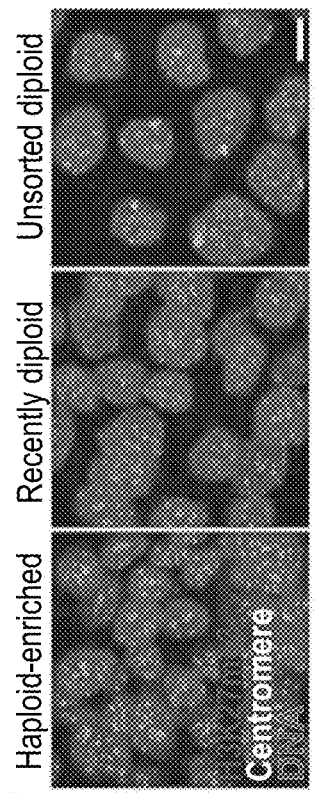
FIG. 3G
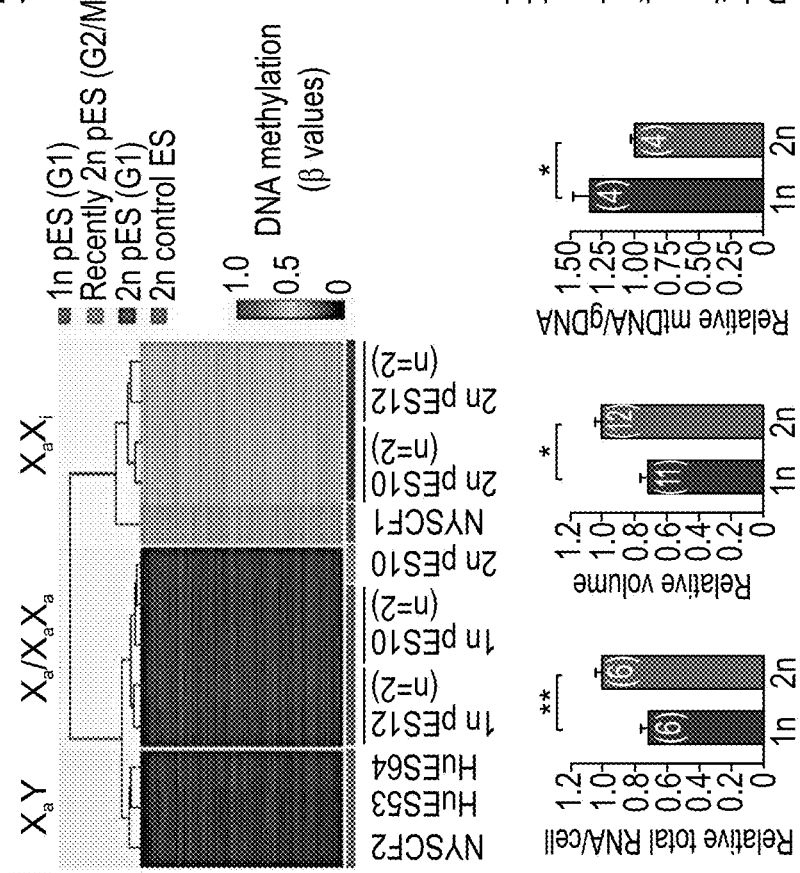
FIG. 3H
FIG. 3I
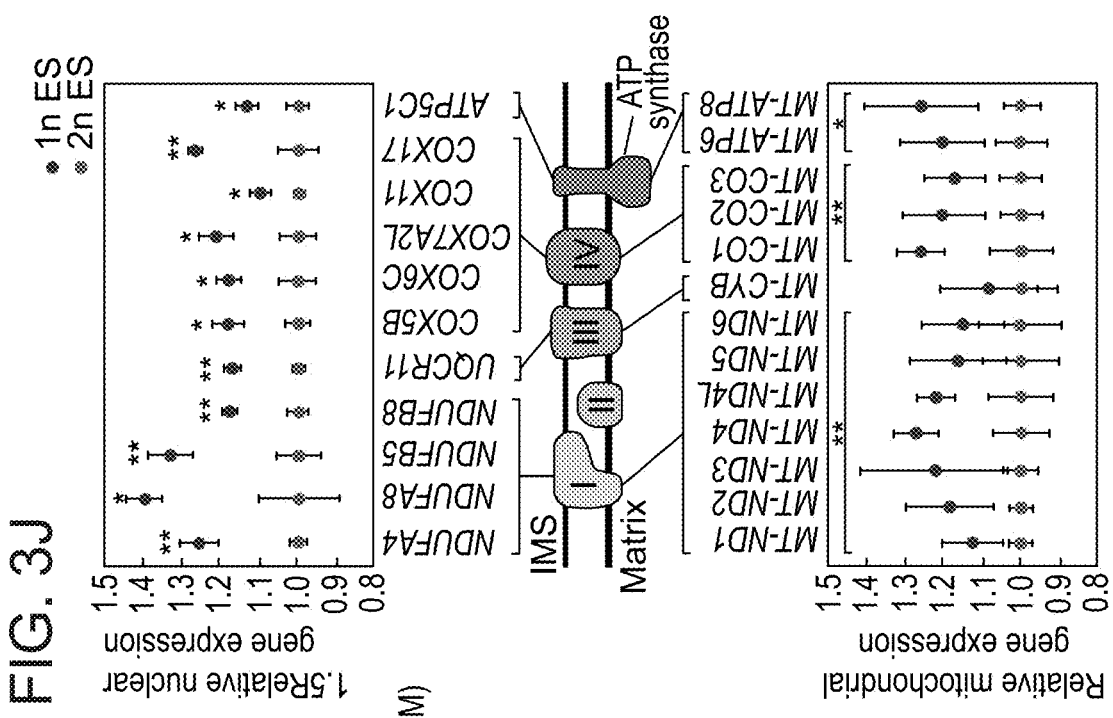
FIG. 3J

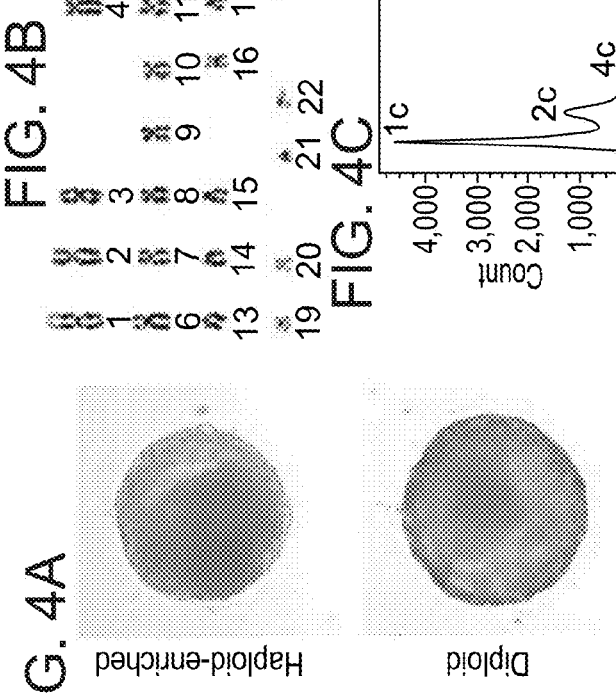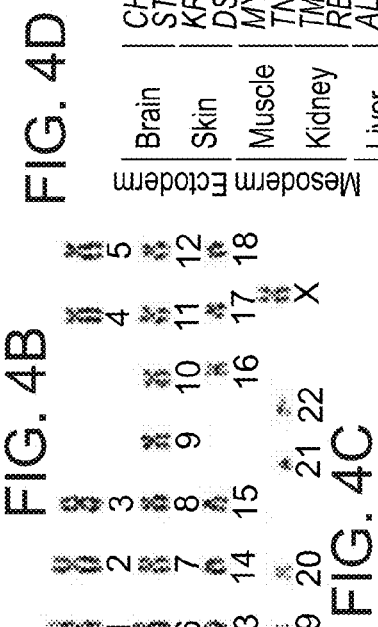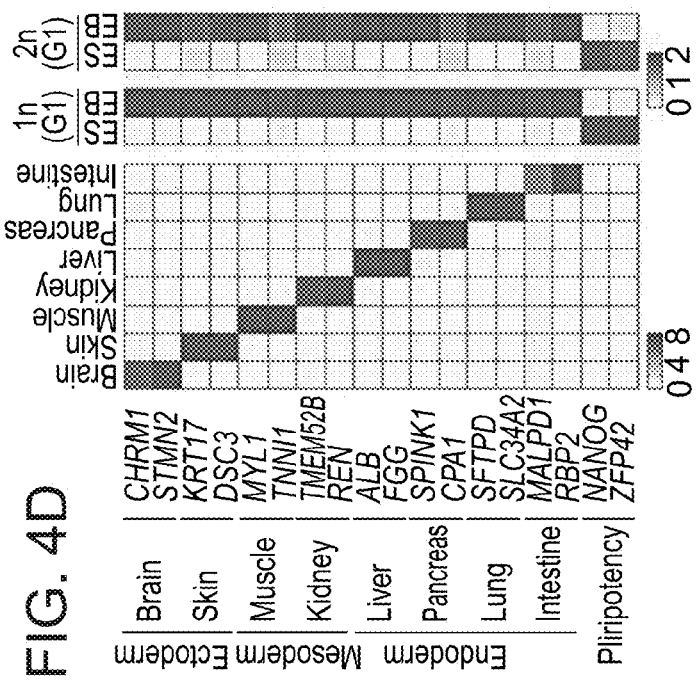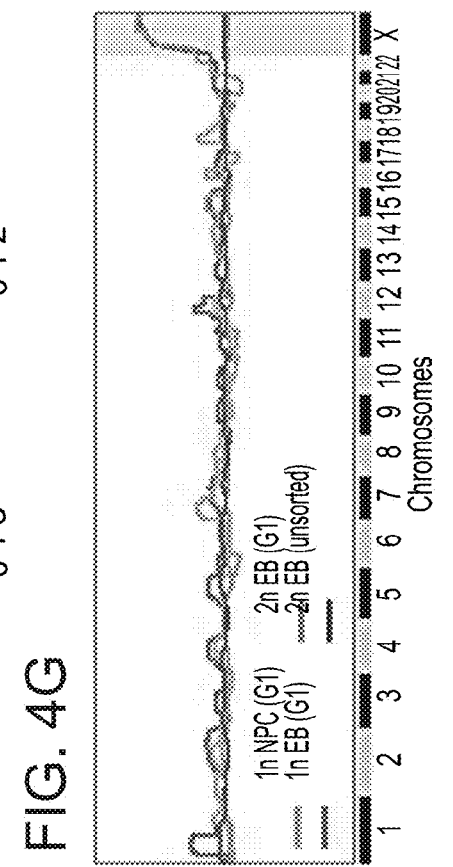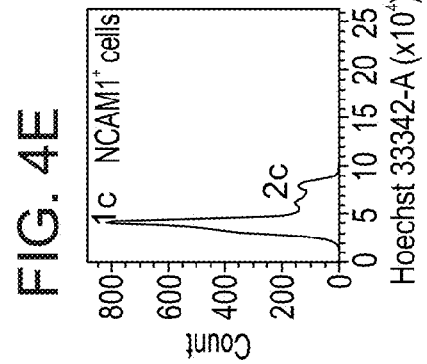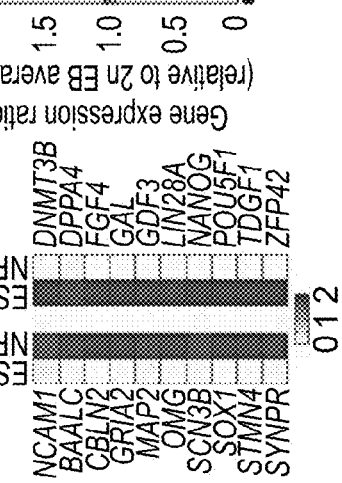

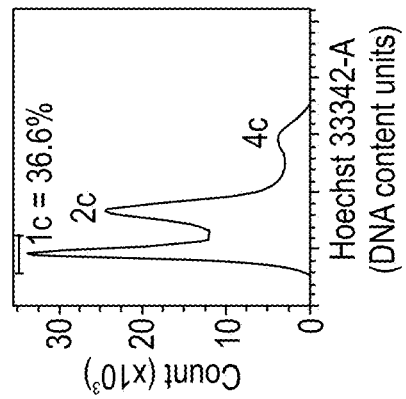
FIG. 6C
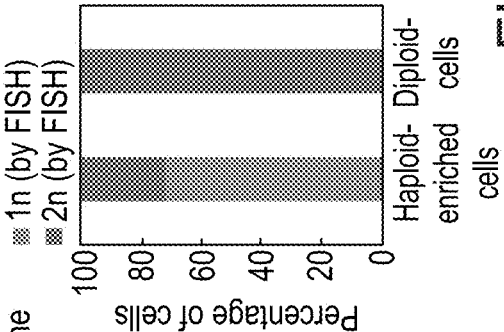
FIG. 6B
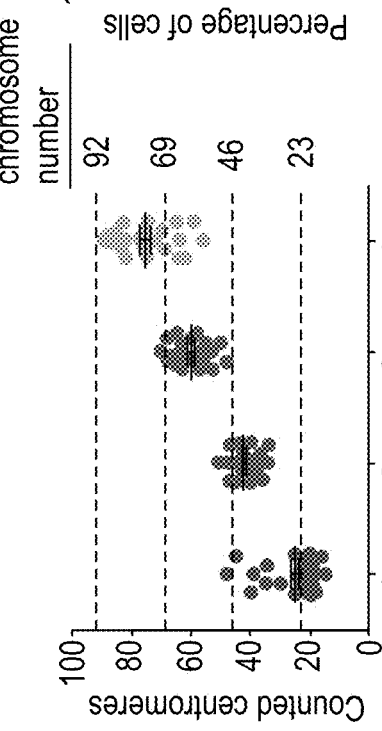
FIG. 6A
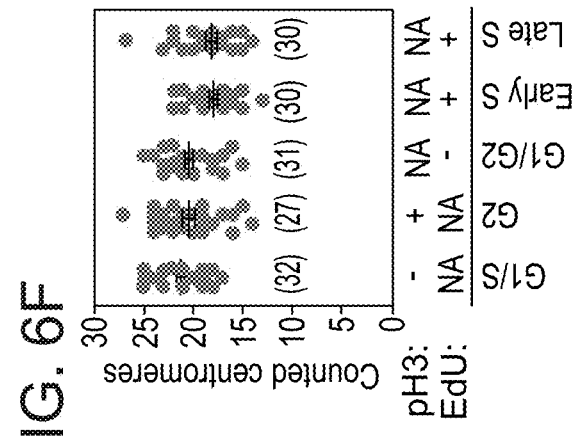
FIG. 6F
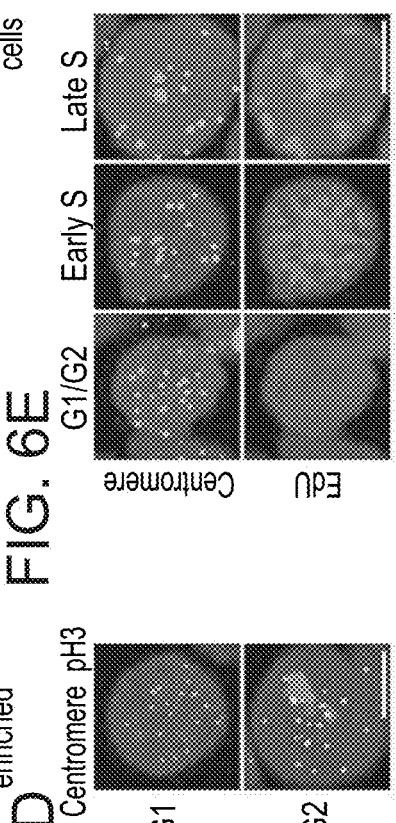
FIG. 6D
FIG. 6E

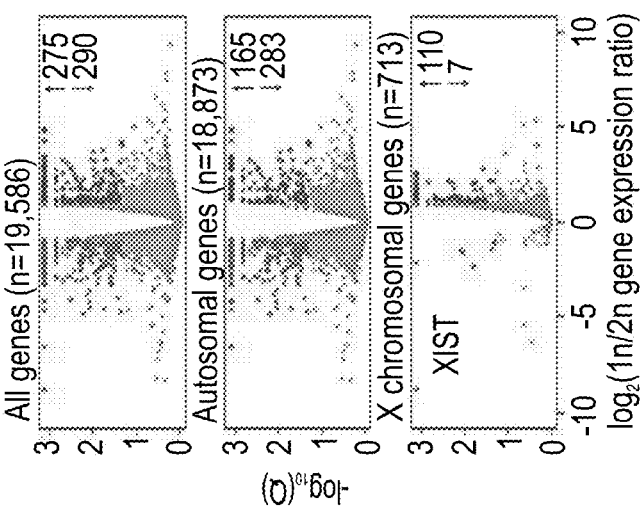
FIG. 9B
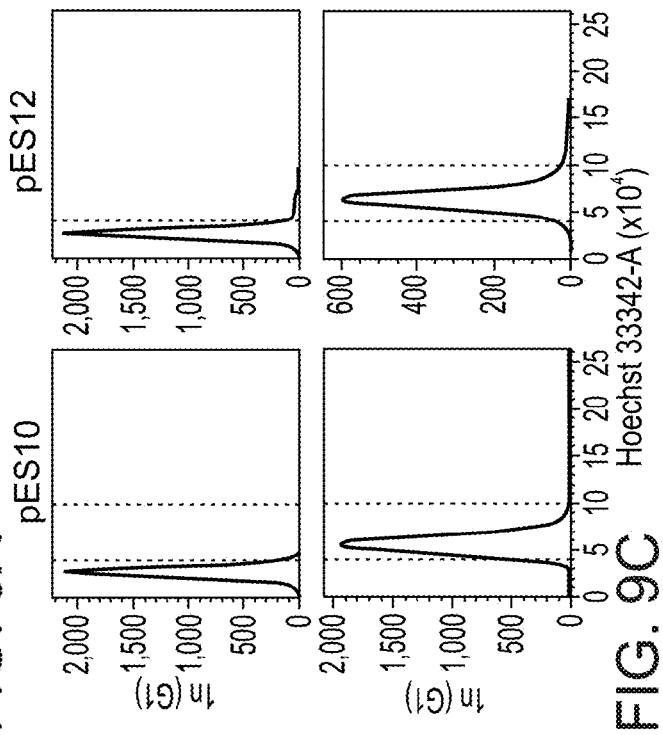
FIG. 9A
FIG. 9C
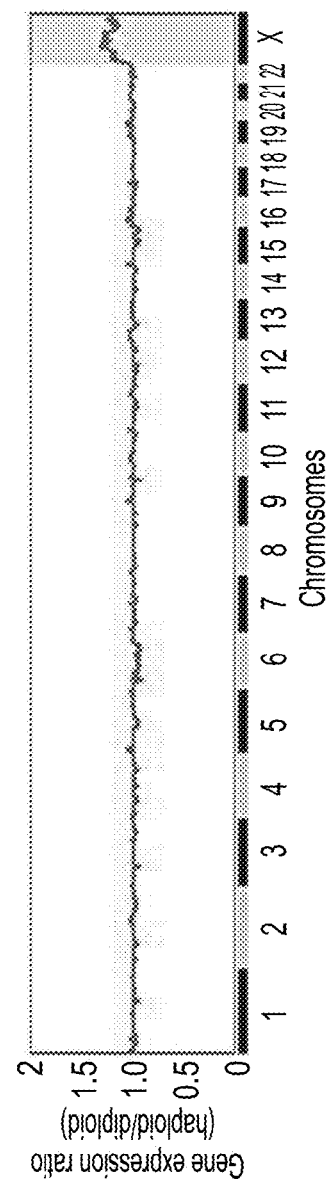
FIG. 9D

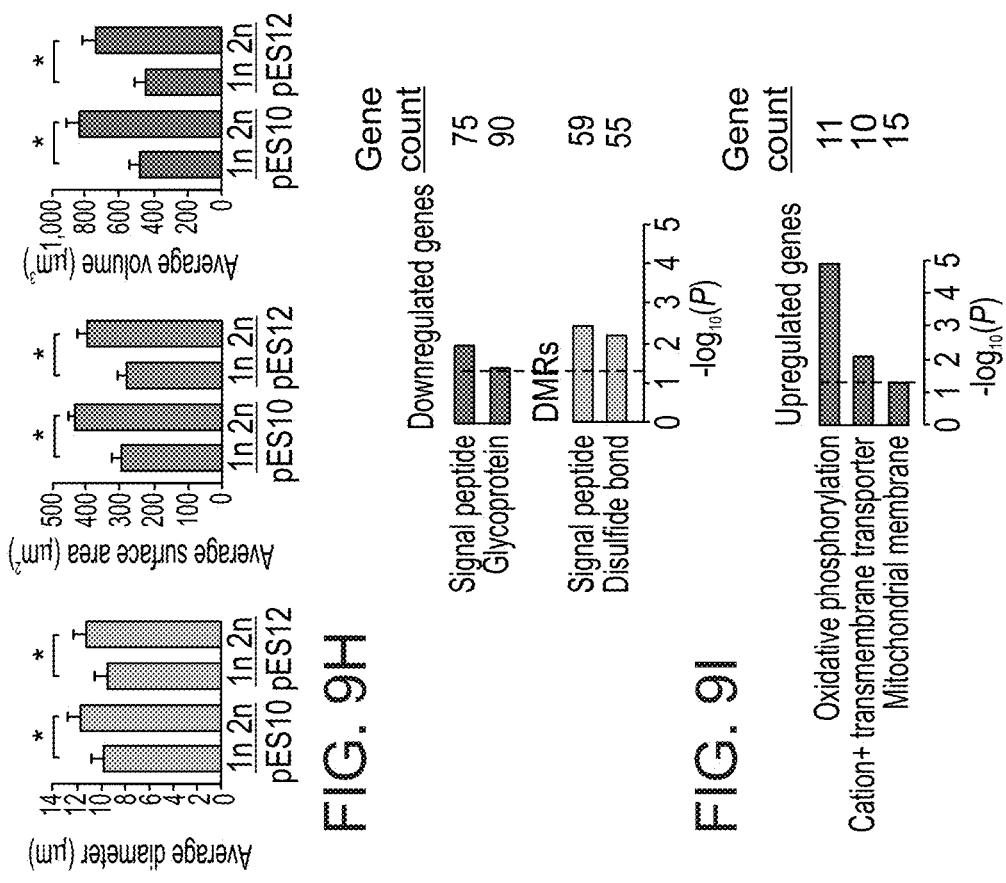
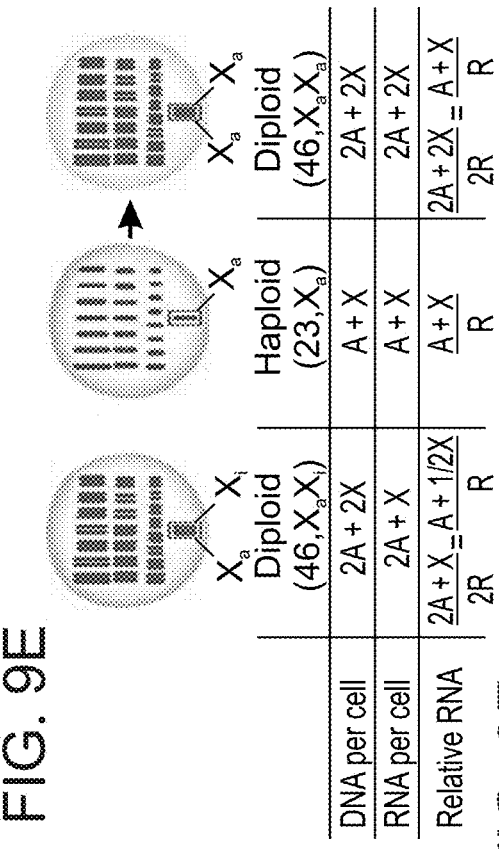
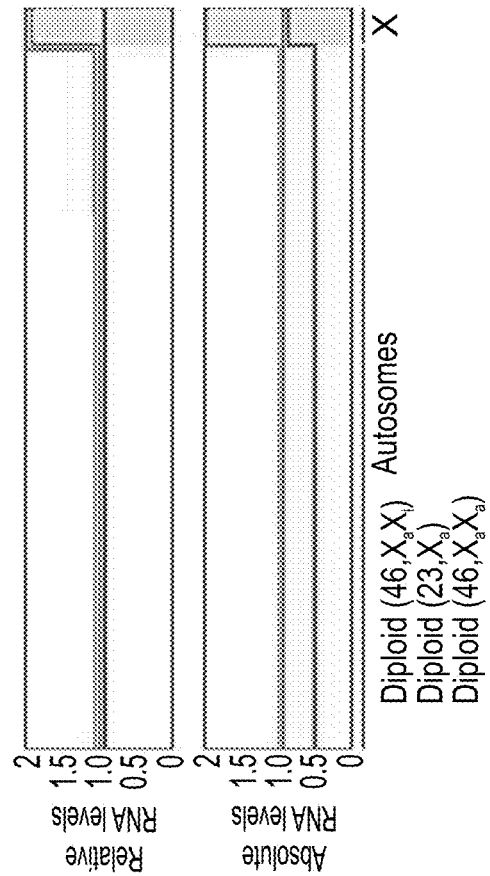
FIG. 9E  FIG. 9G  FIG. 9H
FIG. 9F  FIG. 9I

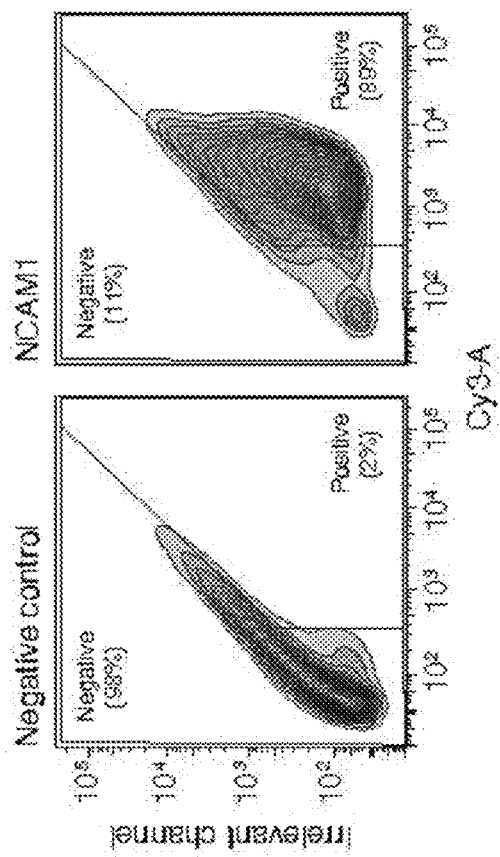
FIG. 11A
FIG. 11B
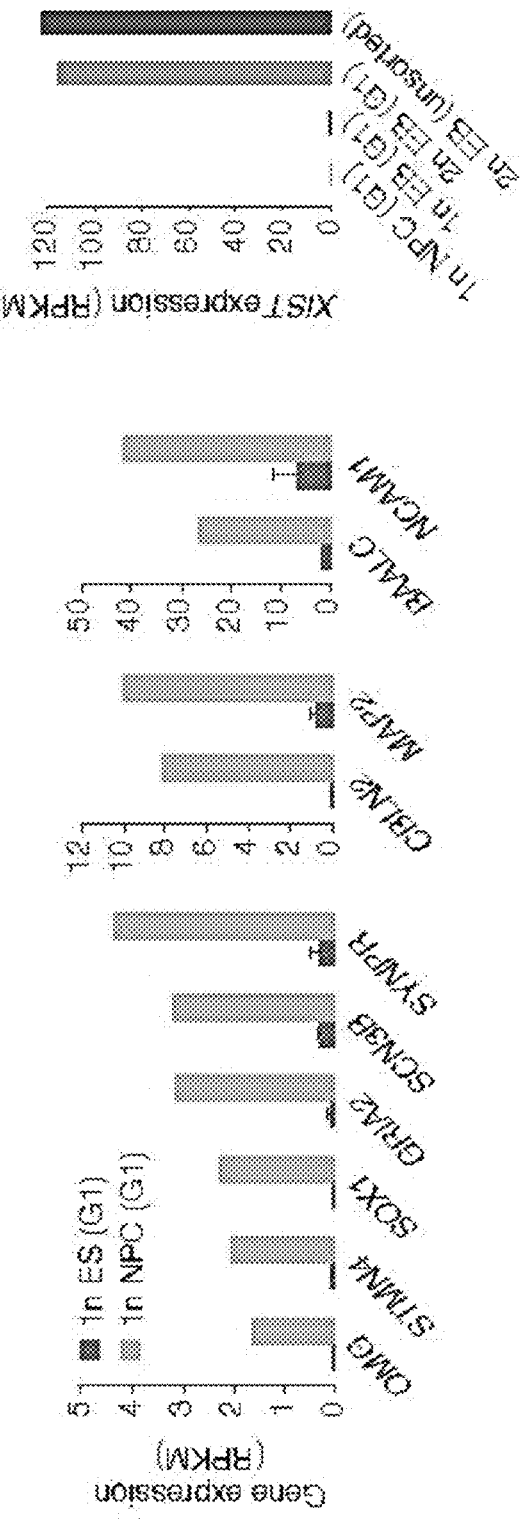
FIG. 11C
FIG. 11D

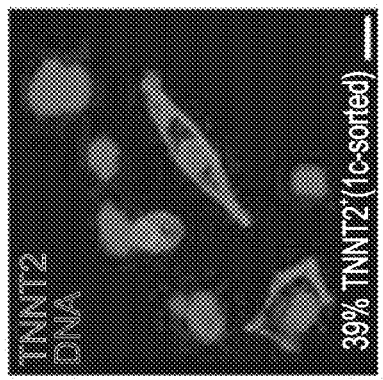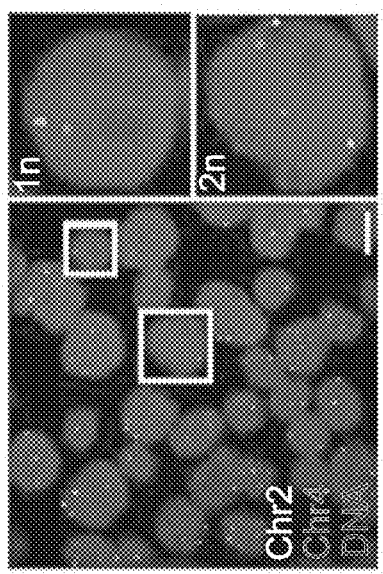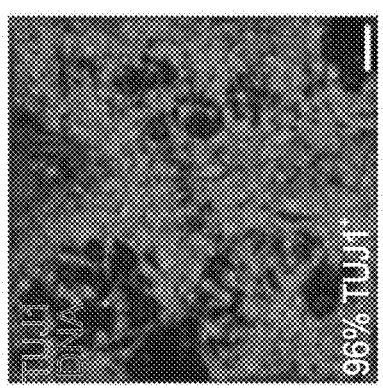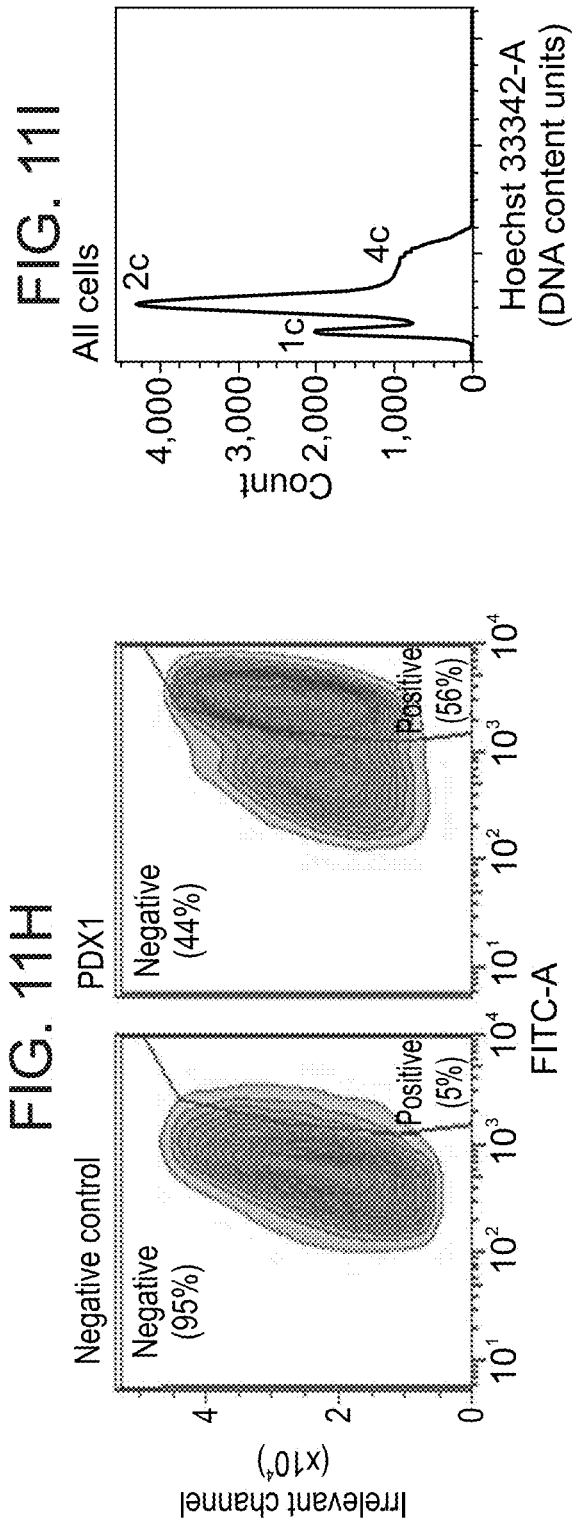

SEQUENCE LISTING

<160> NUMBER OF SEQ ID NOS: 5

<210> SEQ ID NO 1
<211> LENGTH: 25
<212> TYPE: DNA
<213> ORGANISM: Artificial Sequence
<220> FEATURE:
<223> OTHER INFORMATION: Single strand DNA oligonucleotide

<400> SEQUENCE: 1
tgttggttat acccttcccg tacta                                  25

<210> SEQ ID NO 2
<211> LENGTH: 25
<212> TYPE: DNA
<213> ORGANISM: Artificial Sequence
<220> FEATURE:
<223> OTHER INFORMATION: Single strand DNA oligonucleotide

<400> SEQUENCE: 2
cctgcaaaga tggtagagta gatga                                  25

<210> SEQ ID NO 3
<211> LENGTH: 23
<212> TYPE: DNA
<213> ORGANISM: Artificial Sequence
<220> FEATURE:
<223> OTHER INFORMATION: Single strand DNA oligonucleotide

<400> SEQUENCE: 3
ccctcatcac agggctctct cca                                    23

<210> SEQ ID NO 4
<211> LENGTH: 24
<212> TYPE: DNA
<213> ORGANISM: Artificial Sequence
<220> FEATURE:
<223> OTHER INFORMATION: Single strand DNA oligonucleotide

<400> SEQUENCE: 4
gggactgtag gctgggaact atgc                                   24

<210> SEQ ID NO 5
<211> LENGTH: 164
<212> TYPE: DNA
<213> ORGANISM: Homo sapiens

<400> SEQUENCE: 5
ctatgagtgt atcgttctgg tgaaacagtt ccgaccacca atgggggct actgcataga      60 gttccctgca ggtgagtcac tcaacatcga attgcttctt agggatgttg gcctgaacca    120
gggtaaagcc tgagaactgc aaagctcagc tctgcagttt ttaa                     164

SCREENING FOR CHEMOTHERAPY RESISTANCE IN HUMAN HAPLOID CELLS

CROSS-REFERENCE TO RELATED APPLICATIONS

This application is a National Phase of PCT Patent Application No. PCT/IL2016/050644 having International filing date of Jun. 19, 2016. The content of this application is incorporated by reference as if fully set forth herein in its entirety.

FIELD AND BACKGROUND OF THE INVENTION

The present invention, in some embodiments thereof, relates to personalized medicine and more specifically to methods of selecting an appropriate therapy for treatment of disease in a subject so as to minimize the chances of drug resistance.

Chemotherapy of malignant tumors is essentially based on the results of prospective, randomized, double-blind phase III studies and corresponding clinical guidelines. However, the clinical response of the individual patient still remains uncertain, although the statistical probability of treatment success is known within large groups of patients from clinical studies. Tumors differ in their molecular architecture and biological behavior from patient to patient and even within the same tumor. There is a large heterogeneity between different subpopulations of tumor cells.

Drug resistance is a major reason for failure of cancer chemotherapy. In present clinical practice, drug resistance can only be recognized during larger periods of treatment. It, therefore, would be of great value for each individual patient to determine resistance before commencing treatment with antineoplastic substances. In nearly 50% of all cancer cases, resistance to chemotherapy already exists before drug treatment. Meanwhile, the knowledge of various resistance mechanisms has increased over the years. While the responsiveness of tumor cells to targeted anti-cancer drugs (e.g., HER2– or estrogen-receptor-targeting small molecules) can be predicted by pre-therapeutic determination of their corresponding targets, the situation is more complicated for clinically long established cytotoxic drugs, where the molecular targets are either less well-defined or which have broader modes of action.

Human haploid embryonic stem cells have been disclosed in Sagi et al. 2016., Nature, 532,107-111. The utility of these cells as a platform for loss-of-function genetic screening was disclosed therein.

Additional background art includes Pettitt et al., PLoS One. 2013; 8(4): e61520 and US Patent Application No. 20140342369.

SUMMARY OF THE INVENTION

According to an aspect of some embodiments of the present invention there is provided a method of selecting an agent for treating a disease of a subject comprising:

(a) exposing a plurality of haploid human embryonic stem (ES) cells to a cytotoxic therapy, wherein at least a portion of said plurality of haploid ES cells comprises a distinct artificially inactivated or overactivated gene;

(b) selecting a cell of said plurality of haploid human embryonic stem (ES) cells which shows resistance to said cytotoxic therapy;

(c) identifying in said cell said distinct artificially inactivated gene; and (d) analyzing the sequence and/or expression of said distinct artificially inactivated gene or activated gene in a cell sample of the subject, wherein an alteration in the sequence and/or level of expression of said gene as compared to the sequence and/or expression of said gene in a control sample is indicative that the agent should be ruled out as a monotherapy for treating the disease in the subject.

According to an aspect of some embodiments of the present invention there is provided a method of ruling out treatment of a cancer with a chemotherapeutic agent in a subject comprising analyzing the sequence and/or expression of Replication Timing Regulatory Factor 1 (RIF1) and/or PIN2/TERF1 Interacting, Telomerase Inhibitor 1 (PINX1) in a tumor sample of the subject wherein an alteration in the sequence and/or level of expression of said RIF1 and/or PINX1 as compared to the sequence and/or expression of said RIF1 and/or PINX1 in a control sample is indicative that the chemotherapeutic agent should be ruled out as a monotherapy for treating the cancer in the subject.

According to an aspect of some embodiments of the present invention there is provided a method of selecting an agent for treating a disease comprising:

(a) exposing a plurality of human haploid cells to a cytotoxic therapy, wherein said cells were differentiated from isolated haploid human embryonic stem (ES) cells, and wherein at least a portion of said plurality of cells comprises a distinct artificially inactivated or overactivated gene;

(b) selecting a cell of said plurality of cells which shows resistance to said cytotoxic therapy; and (c) identifying in said cell said distinct artificially inactivated or overactivated gene.

According to an aspect of some embodiments of the present invention there is provided a kit comprising a first detection agent which specifically detects Replication Timing Regulatory Factor 1 (RIF1) and a second detection agent which specifically detects PIN2/TERF1 Interacting, Telomerase Inhibitor 1 (PINX1).

According to some embodiments of the invention, at least a portion of said plurality of haploid ES cells comprises a distinct artificially inactivated gene.

According to some embodiments of the invention, the haploid human ES cells comprise a gene trap vector which brings about inactivation of the gene.

According to some embodiments of the invention, gene trap vector encodes a reporter polypeptide which is used to identify said artificially inactivated gene.

According to some embodiments of the invention, the haploid human ES cells comprise components of the CRISPR system which brings about inactivation or activation of said gene.

According to some embodiments of the invention, the exposing a plurality of haploid human embryonic stem (ES) cells is effected in a single container.

According to some embodiments of the invention, the exposing a plurality of haploid human embryonic stem (ES) cells is effected in a plurality of containers, wherein each container of said plurality of containers comprises haploid human embryonic stem (ES) cells with an identical artificially inactivated gene.

According to some embodiments of the invention, the disease is cancer.

According to some embodiments of the invention, the cell sample is a tumor sample.

According to some embodiments of the invention, the cytotoxic therapy comprises a pharmaceutical agent.

According to some embodiments of the invention, pharmaceutical agent is a chemotherapeutic agent.

According to some embodiments of the invention, the chemotherapeutic agent is an antibiotic agent.

According to some embodiments of the invention, the antibiotic agent is an anthracycline or a chromomycin.

According to some embodiments of the invention, the antibiotic agent is selected from the group consisting of Doxorubicin, Daunorubicin, Mitoxantrone, Idarubicin, Dactinomycin, Plicamycin, Mitomycin and Bleomycin.

According to some embodiments of the invention, the antibiotic agent is Bleomycin.

According to some embodiments of the invention, the cytotoxic therapy comprises a radiation therapy.

According to some embodiments of the invention, identifying is effected by sequencing DNA of said cells.

According to some embodiments of the invention, haploid human ES cells are generated by:
  (a) identifying haploid metaphase cells in a sample from a population of ES cells, wherein the ES cells are derived from an artificially activated human oocyte; and
  (b) sorting the population of ES cells based on cell ploidy to produce a population of haploid human ES cells.

According to some embodiments of the invention, the method further comprises maintaining the enriched population of ES cells in culture for at least three passages.

According to some embodiments of the invention, the haploid metaphase cells in the sample are identified by metaphase spread analysis or sub-2c cell sorting.

According to some embodiments of the invention, the haploid metaphase cells in the sample are identified by flow cytometry, centromere protein immunofluorescence staining, or DNA fluorescence in situ hybridization.

According to some embodiments of the invention, the sorting step comprises at least one cycle of fluorescence-activated cell sorting (FACS).

According to some embodiments of the invention, the chemotherapeutic agent is an antibiotic agent.

According to some embodiments of the invention, the antibiotic agent is an anthracycline or a chromomycin.

According to some embodiments of the invention, the antibiotic agent is selected from the group consisting of Doxorubicin, Daunorubicin, Mitoxantrone, Idarubicin, Dactinomycin, Plicamycin, Mitomycin and Bleomycin.

According to some embodiments of the invention, the antibiotic agent is Bleomycin.

According to some embodiments of the invention, the method further comprises treating the subject with an anti cancer therapy which is not said chemotherapy.

According to some embodiments of the invention, the detection reagent and/or said second detection agent is an antibody or a nucleic acid.

According to some embodiments of the invention, the method further comprises analyzing the sequence and/or expression of said distinct artificially inactivated gene in a cell sample of a subject having the disease, wherein an alteration in the sequence and/or level of expression of said gene as compared to the sequence and/or expression of said gene in a control sample is indicative that the agent should be ruled out as a monotherapy for treating the disease in the subject.

According to some embodiments of the invention, the haploid cells are multipotent cells.

According to some embodiments of the invention, the haploid cells are terminally differentiated cells.

According to some embodiments of the invention, at least a portion of the plurality of cells comprises a distinct artificially inactivated gene.

According to some embodiments of the invention, the haploid cells comprise a gene trap vector which brings about inactivation of said gene.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
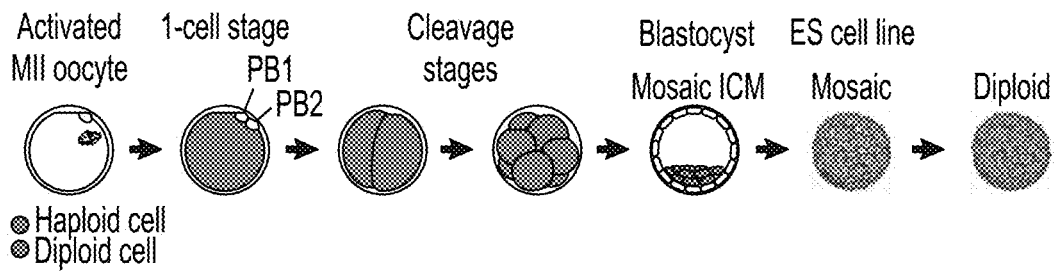
Figure 1C:
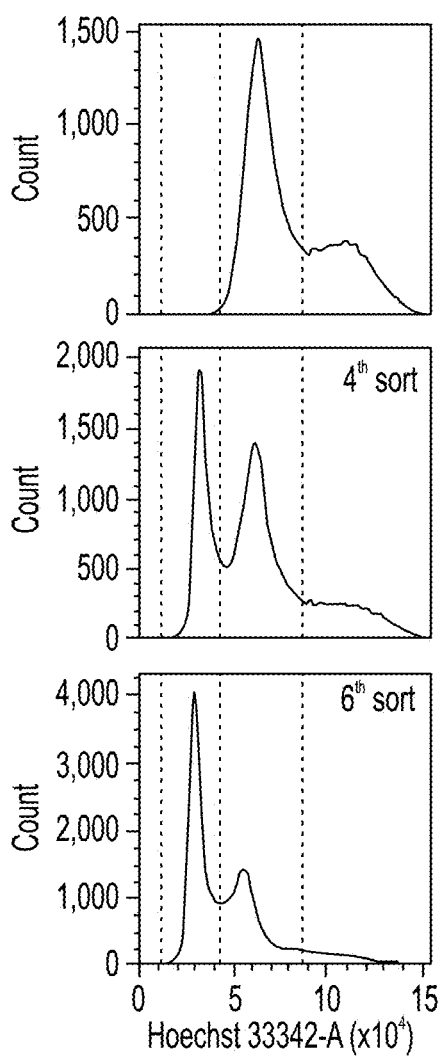
Figure 1D:
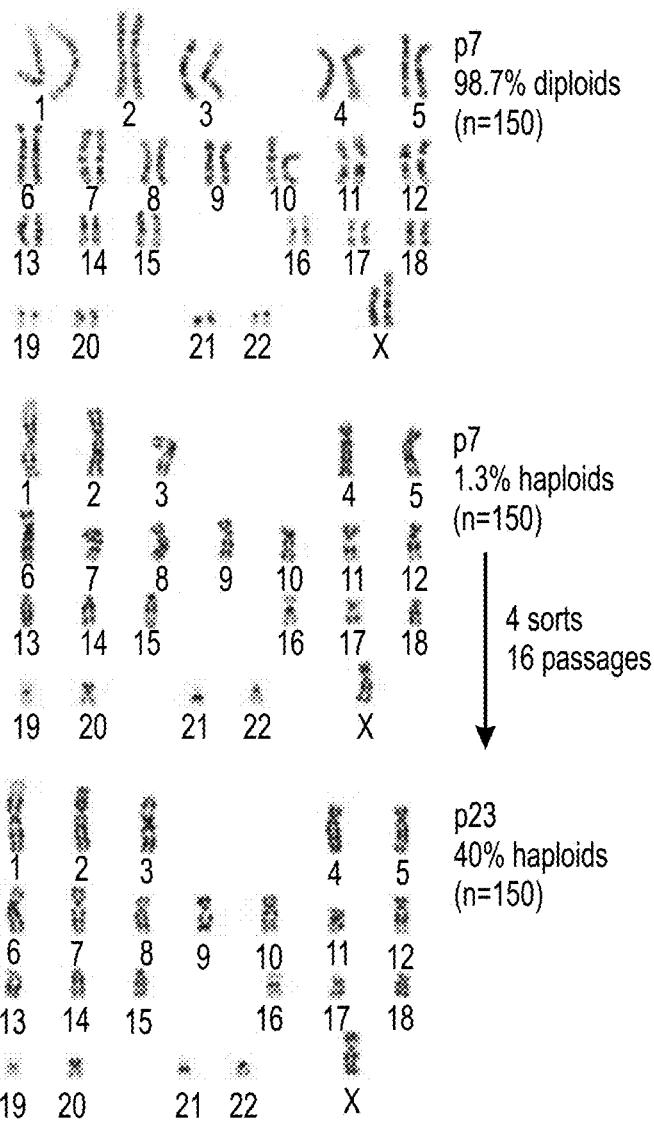
Figure 1B:
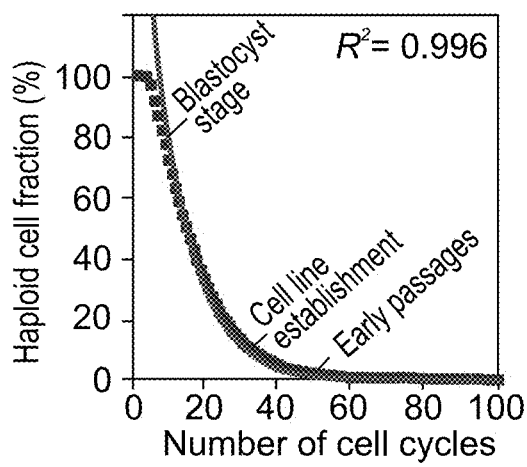
Figure 1E:
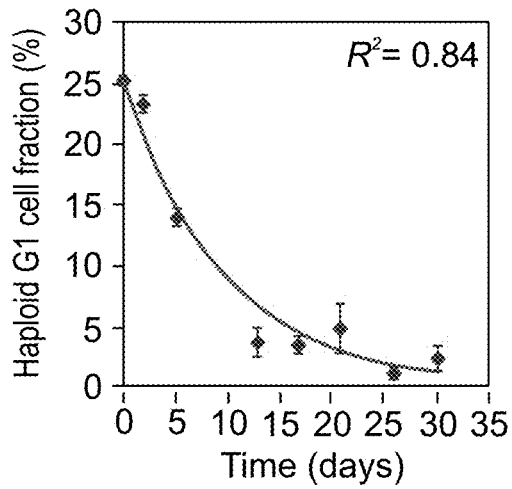
Figure 1F:
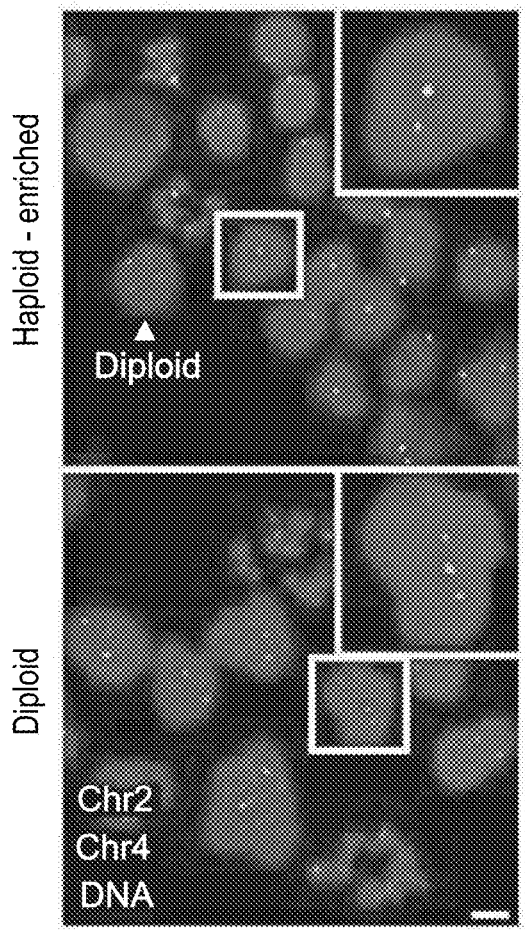
Figure 1G:
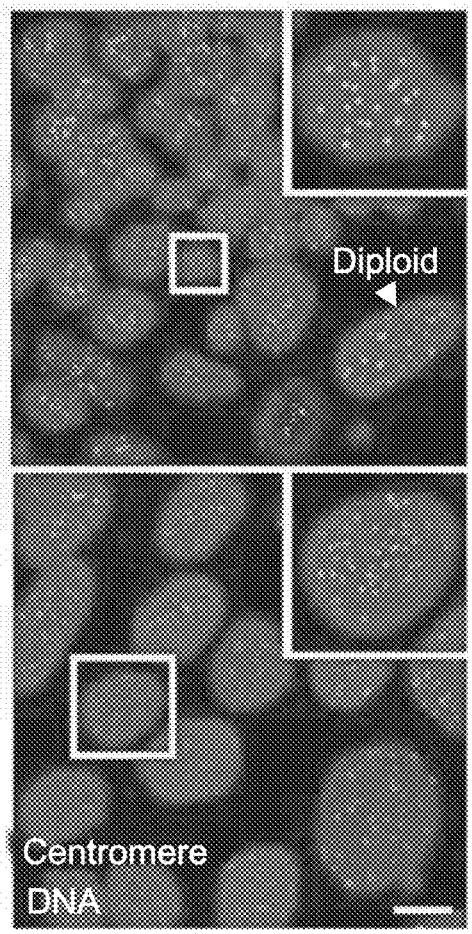

FIGS. 1A-G show derivation of haploid human ES cell lines. FIG. 1A shows a schematic outline of parthenogenetic oocyte activation and potential haploidy in resulting ES cell lines. Second polar body (PB) extrusion at MII without fertilization results in a haploid 1-cell stage embryo and haploid cells are gradually eliminated due to diploidization. FIG. 1B shows a diploidization rate model for a haploid egg with a theoretical diploidization probability of 10%, overlaid with an exponential decay fit (red curve). Approximated cell cycle numbers for different ES cell line derivation stages is indicated. FIG. 1C shows establishment of the haploid-enriched human ES cell line h-pES10 after repeated sorting and enrichment of 1c-cells. c: chromosomal copies. From top to bottom: DNA content profiles of unsorted diploid cells, partially purified haploid cells at the fourth sort, and mostly purified haploid cells at the sixth sort. FIG. 1D shows diploid and haploid karyotypes of pES10 before and after 4 rounds of haploid cell enrichment and expansion. FIG. 1E shows diploidization dynamics of h-pES10 over seven passages by flow cytometry, overlaid with an exponential fit to the data (red curve). Error bars show standard deviation (s.d.). FIG. 1F shows DNA FISH and FIG. 1G shows centromere staining in haploid-enriched and unsorted diploid pES10 cells. Magnified insets show representative haploid and diploid nuclei with either single or double hybridization signals (FIG. 1F) and 23 or 46 centromeres (FIG. 1G), respectively. White arrows point to diploid nuclei. Scale bars=10 μm.

Figure 2A:
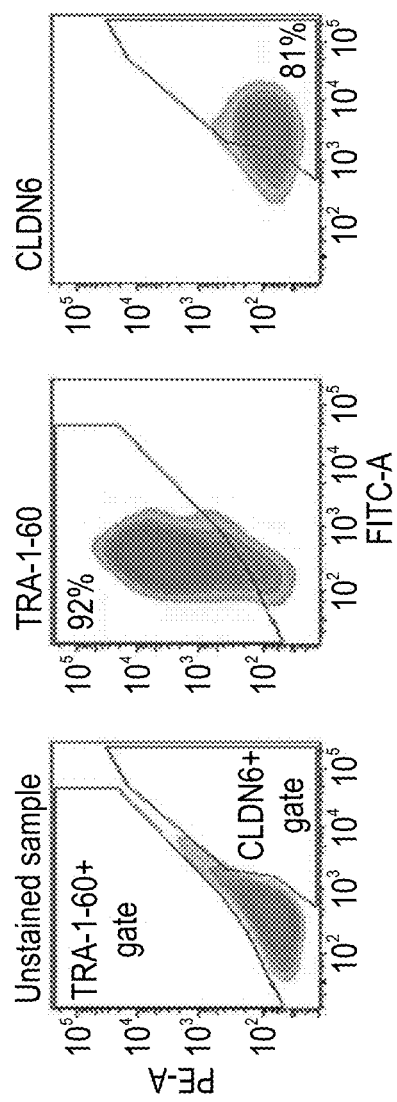
Figure 2B:
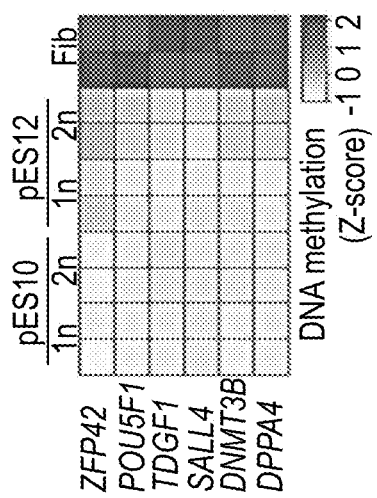
Figure 2D:
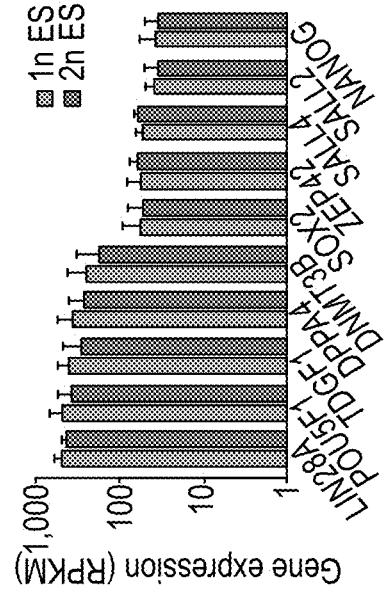
Figure 2E:
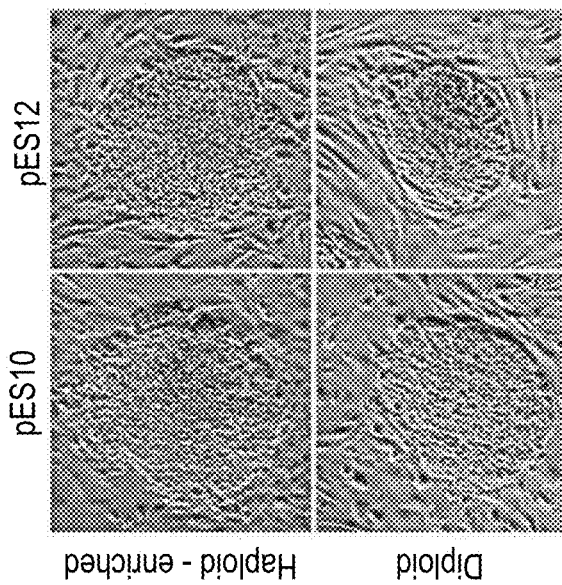
Figure 2F:
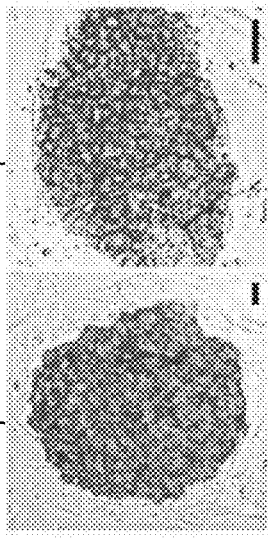
Figure 2C:
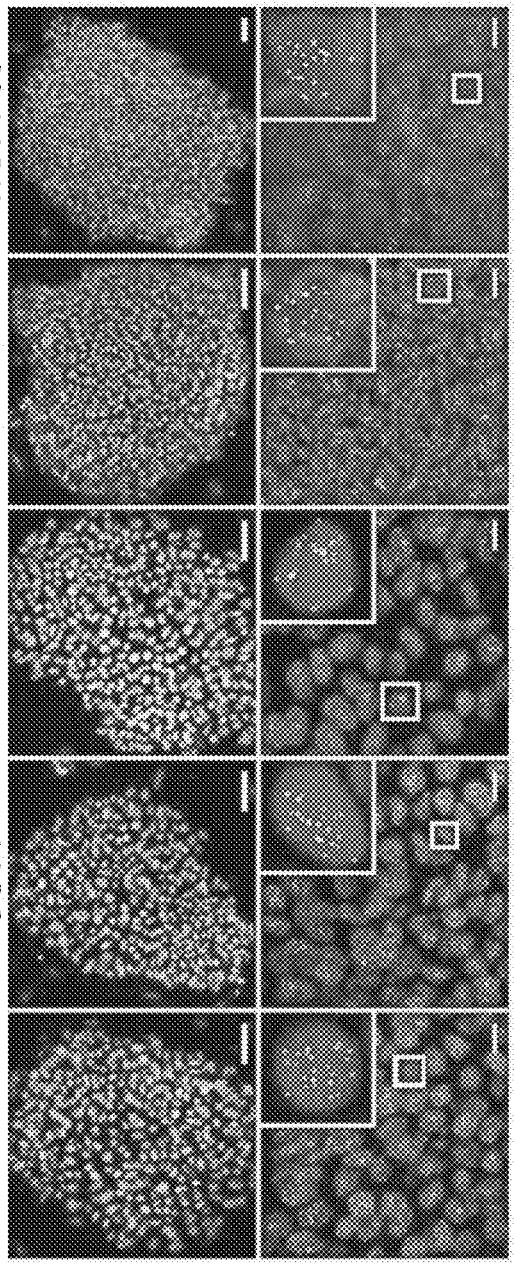
Figure 2G:
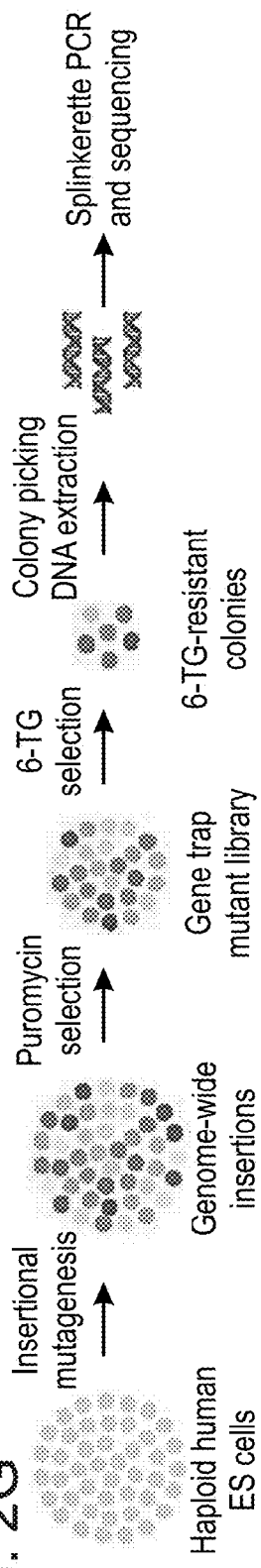
Figure 2H:
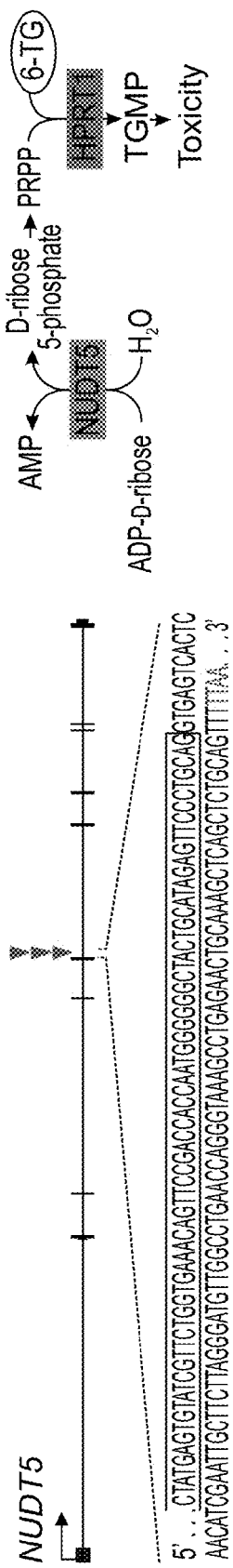
Figure 2I:
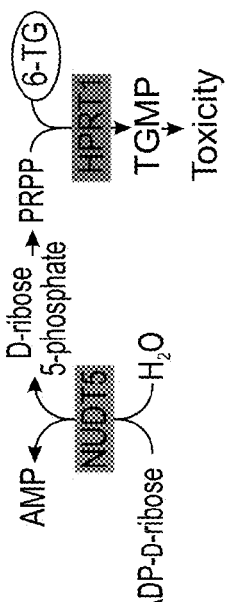

FIGS. 2A-I show that haploid human ES cells display classical characteristics of pluripotent stem cells and enable loss-of-function genetic screening. FIG. 2A shows colony morphology of haploid-enriched and matching diploid cell lines. Scale bar is 50 μm. FIG. 2B shows alkaline phosphatase staining of h-pES10 and h-pES12. Scale bars=50 µm. FIG. 2C shows co-staining of pluripotency markers (red), centromeres (green) and DNA (blue) in h-pES10 at colony resolution (upper panel; scale bars=50 µm) and single-cell resolution (lower panel; scale bars=10 µm). Magnified insets show representative haploid cells with 23 centromeres. FIG. 2D shows flow cytometry analysis of h-pES10 by co-staining DNA and cell surface markers TRA-1-60 and CLDN6, after gating for haploid cells in G1. FIG. 2E shows mean expression levels±s.d. of pluripotency genes in haploid (1n) and diploid (2n) pES10 and pES12 cells in G1 (n=4 for each group, with two biological replicates for each cell line, logarithmic scale). RPKM: reads per kilobase per million fragments mapped. FIG. 2F shows DNA methylation levels at pluripotency genes in duplicates of haploid (1n) and diploid (2n) pES10 and pES12 cells in G1, as well as control fibroblasts (Fib). FIG. 2G shows a schematic overview of genome-wide gene trapping in haploid human ES cells and screening for 6-TG-resistance genes. FIG. 2H shows NUDT5 insertions (red arrows) detected in 3 6-TG-resistant colonies. Upper panel shows gene structure. Lower panel shows genomic sequence of the intronic insertion site (indicated by TTAA) and upstream exonic sequence (in box). The sequence in the figure is set forth in SEQ ID NO: 5. FIG. 2I shows a schematic of the metabolic pathway leading to 6-TG toxicity through NUDT5-mediated PRPP production. ADP: adenosine diphosphate; AMP: adenosine monophosphate.

FIGS. 3A-J show molecular and cellular comparisons of haploid and diploid ES cells. FIG. 3A shows an experimental scheme of haploid and diploid ES cell isolation for comparative analyses. FIG. 3B shows RNA-Seq-based hierarchical clustering analysis of isogenic haploid (1n) and diploid (2n) cells in G1 (two biological replicates per cell line), compared with a 2n pES12-derived embryoid body (EB) sample. FIG. 3C shows a pie chart representation of relatively downregulated and upregulated genes in haploid vs. diploid ES cells on autosomes and X chromosome. FIG. 3D shows hierarchical clustering analysis by X chromosomal genes. FIGS. 3E-H show differential X chromosome inactivation (XCI) status in haploid and diploid ES cells. FIG. 3E shows genome-wide gene expression moving median plot (relative to the average of diploids in G1 by RNA-Seq, window size=100 genes). FIG. 3F shows XIST expression levels. (1) and (2) denote biological replicates. FIG. 3G shows H3K27me3 staining. Scale bar=10 µm. FIG. 3H shows DNA methylation levels on the X chromosome. FIG. 3I shows relative total RNA, cell volume and ratio of mitochondrial DNA (mtDNA) to genomic DNA (gDNA) between G1-sorted haploid and diploid ES cells. Numbers of replicates are indicated in parenthesis. Error bars represent s.d. FIG. 3J shows mean expression levels±standard error of the mean (s.e.m.) of nuclear (top panel) and mitochondrial oxidative phosphorylation genes (lower panel), upregulated in haploid ES cells relative to diploid ES cells (n=4 for each group, as in FIG. 2e), and schematic representation of their organization in this pathway. IMS: intermembrane space. *$P<0.05$; **$P<0.01$ (two-tailed unpaired Student's t test).

Figure 4H:
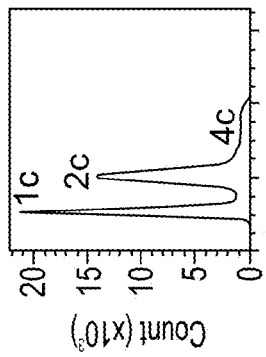
Figure 4I:
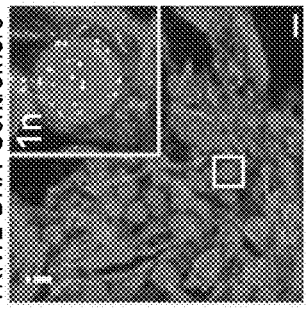
Figure 4J:
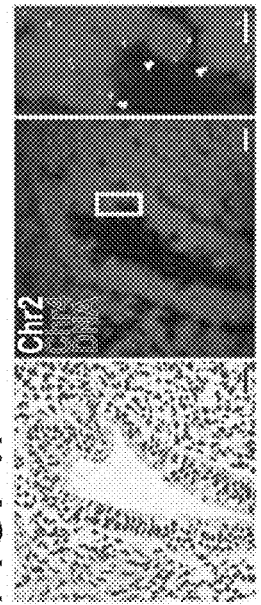
Figure 4K:
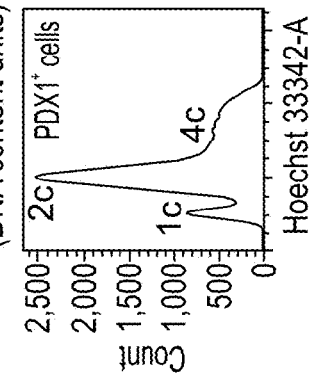
Figure 4M:
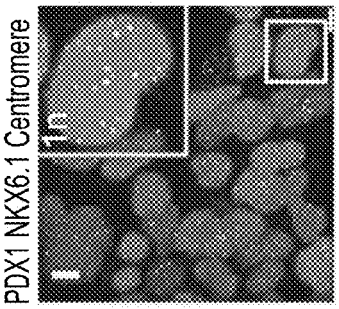
Figure 4N:
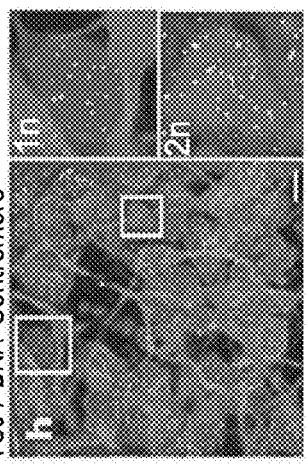
Figure 4O:
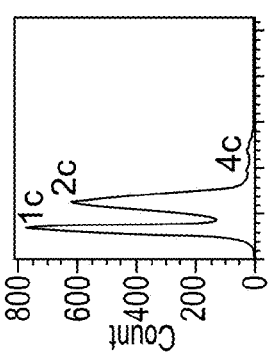
Figure 4P:
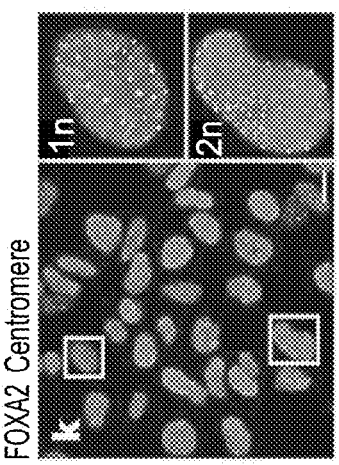

FIGS. 4A-P show the differentiation potential of haploid human cells. FIG. 4A shows representative images of 21-day EBs from haploid-enriched and diploid pES12 cells. Scale bar=100 µm. FIG. 4B shows haploid karyotype of cells dissociated from haploid-enriched EBs in FIG. 4a (plated cells shown in FIG. 10a). FIG. 4C shows the DNA content profile of h-pES10 EB cells. FIG. 4D shows expression of tissue- and pluripotency-specific genes in G1-sorted haploid (1n) and diploid (2n) ES and EB pES10 cells. FIG. 4E shows the DNA content profile of NCAM1-positive h-pES10-derived neural progenitor cells (NPCs). FIG. 4F shows expression of neural- and pluripotency-specific genes (right and left panels, respectively) in G1-sorted haploid pES10 ES cells and NPCs. Color-coded scale shows expression relative to the mean across the NPC sample and an ES cell duplicate. FIG. 4G shows differential XCI status in haploid and diploid pES10-derived EBs and NPCs, as shown by genome-wide gene expression moving median plot (window size=200 genes). Centromere and differentiation marker co-staining is shown in h-pES12-derived TUJ1-positive neurons (FIG. 4H), TNNT2-positive cardiomyocytes (FIG. 4I), FOXA2-positive definitive endoderm cells (FIG. 4K) and PDX1-positive and NKX6.1-positive PPCs (FIG. 4l). Magnified insets show representative haploid and diploid nuclei. Scale bars=10 µm. DNA content profiles are shown for h-pES12 cells differentiated into cardiomyocytes (FIG. 4J) and PDX1-positive PPCs (FIG. 4M). FIG. 4N shows TUJ1 (ectoderm), α-SMA (mesoderm), AFP (endoderm) and OCT4 (pluripotency) staining in an h-pES12-derived teratoma. Scale bars=50 µm. FIG. 4O shows DNA content profile of an h-pES10-derived teratoma. FIG. 4P shows serial h-pES12-derived teratoma sections analyzed by histology with hematoxylin and eosin staining (left panel; scale bar=20 µm) and DNA FISH (right panel; scale bar=20 µm). Magnified inset shows representative haploid nuclei (scale bar=5 µm).

Figures 5A, 5B:
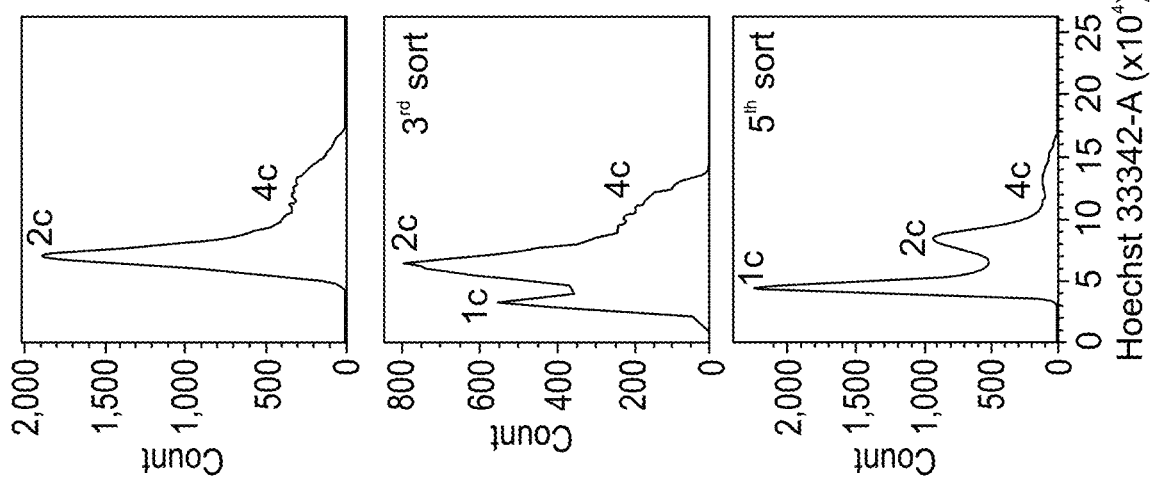
Figure 5C:
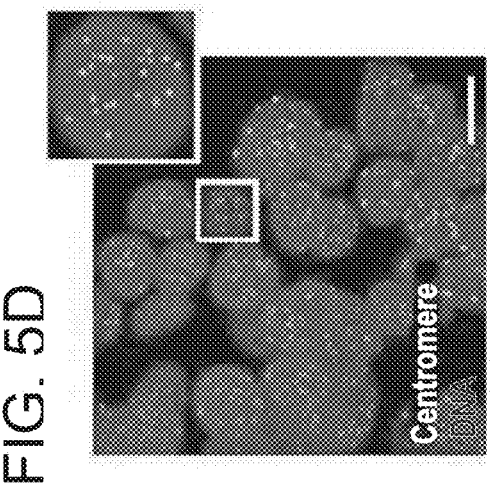
Figure 5D:
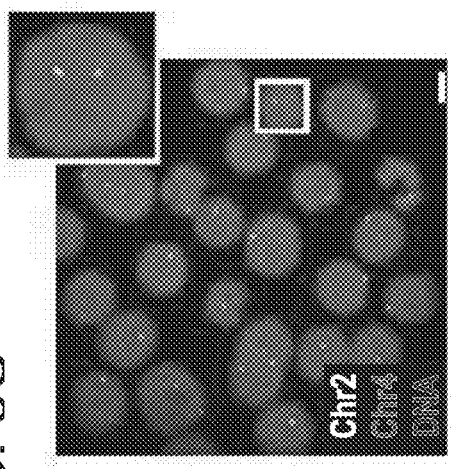
Figure 5E:
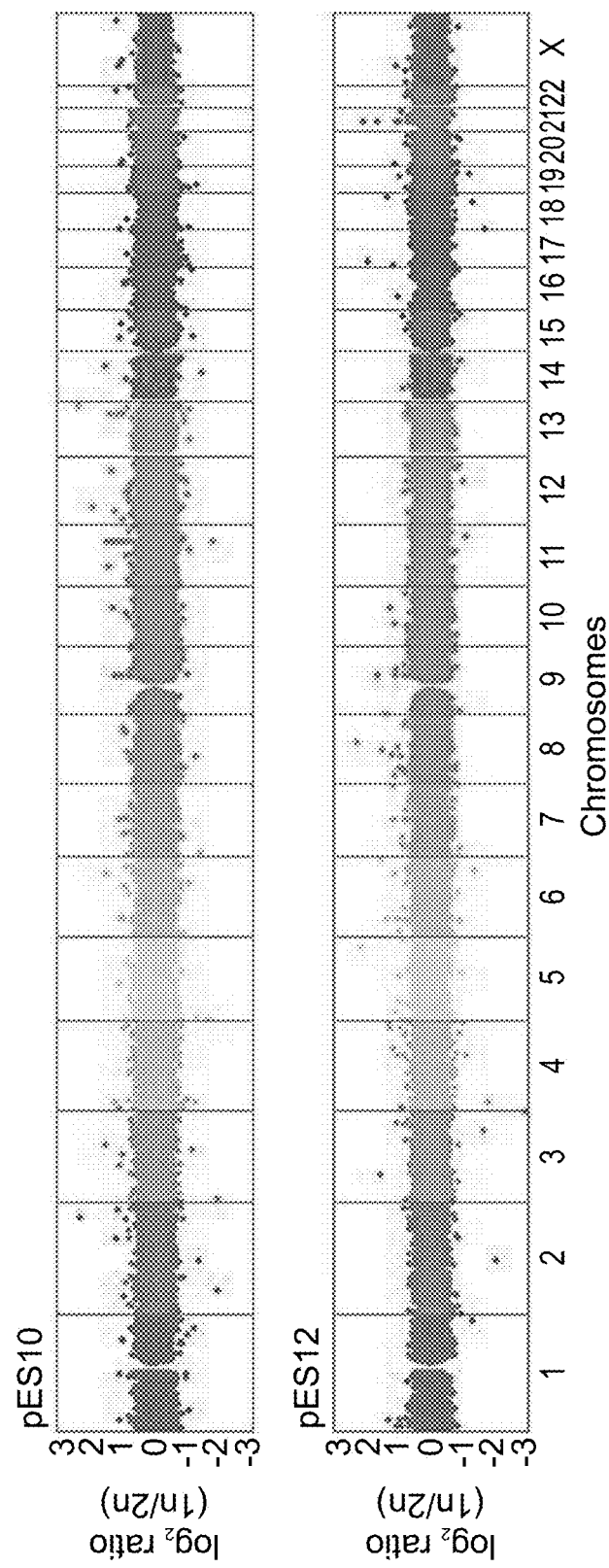

FIGS. 5A-E show derivation of haploid human ES cell line h-pES12. FIG. 5A shows establishment of a haploid-enriched human ES cell line from pES12 cells after repeated sorting and enrichment of 1c-cells using Hoechst 33342 staining. Shown from top to bottom are the DNA content profiles of unsorted diploid cells, partially purified haploid cells at the third sort, and mostly purified haploid cells at the fifth sort. c: chromosomal copies. FIG. 5B shows karyotypes and haploid metaphase percentage over the course of enrichment and passaging. FIG. 5C shows DNA FISH and FIG. 5D shows centromere protein immunofluorescence staining in h-pES12. Magnified insets show representative haploid nuclei with single hybridization signals (FIG. 5C) and 23 centromeres (FIG. 5D), respectively. Scale bars=10 µm. FIG. 5E shows single nucleotide polymorphism (SNP) array-based copy number variation (CNV) analysis comparing haploid (1n) pES10 and pES12 cells to their unsorted diploid (2n) counterparts (logarithmic scale).

FIGS. 6A-F show determination of ploidy at single-cell level by quantification of centromere foci. FIG. 6A shows that the counted number of centromeres correlates with ploidy. 1n: haploid-enriched pES10 cells grown for 4 passages after the forth sort (n=33; 76% haploids by this assay); 2n: unsorted diploid pES10 cells (n=34); 3n: soPS2 cells[35] (n=27); 4n: Hybrid1 cells[36] (n=27). Black horizontal lines indicate mean±s.e.m. and dashed lines mark expected chromosome numbers. FIG. 6B shows quantification of haploid (1n) and diploid (2n) cells by DNA FISH in the haploid-enriched (n=152; 73% haploids by this assay) and diploid (n=135) cells in FIG. 6a. FIG. 6C shows the DNA content profile of the haploid-enriched cells in FIG. 6a (73% haploids by this assay). c: chromosomal copies. Co-staining of centromeres and either phospho-histone 3 (pH3, Ser10) (FIG. 6D) or 5-ethynyl-2'-deoxyuridine (EdU) (FIG. 6E) distinguishes between different stages of interphase in haploid pES12 cells. DNA staining is shown in blue. Scale bar=5 µm. FIG. 6F shows quantification of centromere counts in the different cell cycle stages shown in FIG. 6D and FIG. 6E. n indicated in parenthesis. Black horizontal lines indicate mean±s.e.m.

Figure 7:
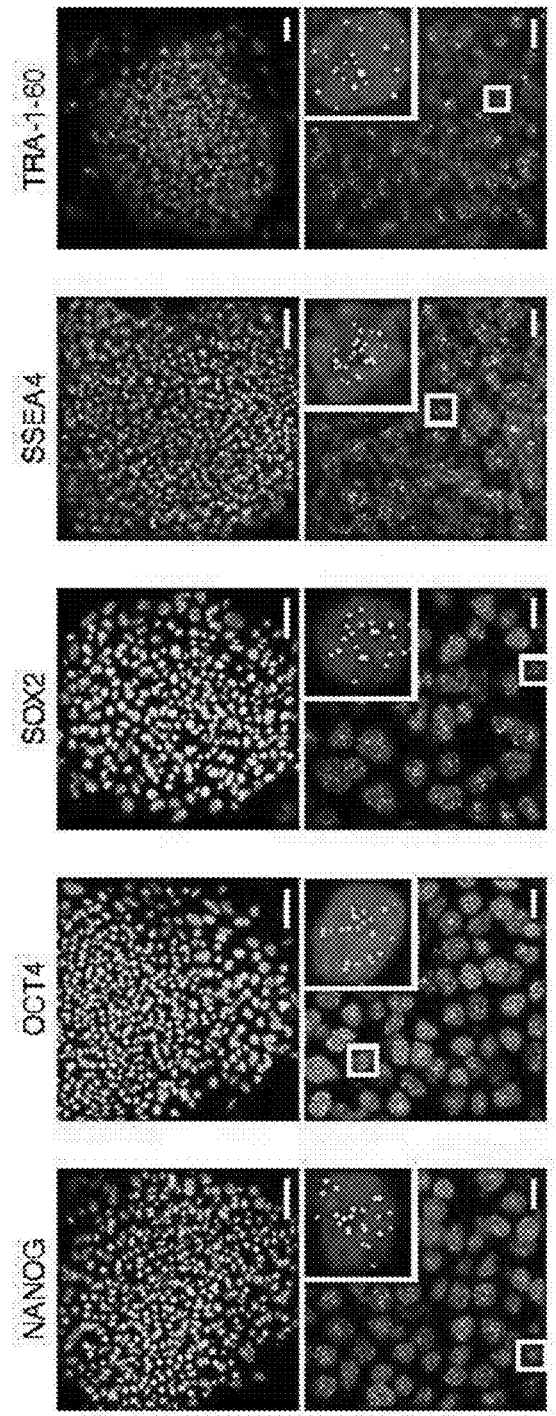

FIG. 7 shows pluripotent stem cell markers in haploid pES12 cells. Co-staining of pluripotency markers NANOG, OCT4, SOX2, SSEA4 and TRA-1-6 (red), centromeres (green) and DNA (blue) in h-pES12 at colony resolution (upper panel; scale bars=50 μm) and single-cell resolution (lower panel; scale bars=10 μm) is shown. Magnified insets show representative haploid cells with 23 centromeres.

Figure 8C:
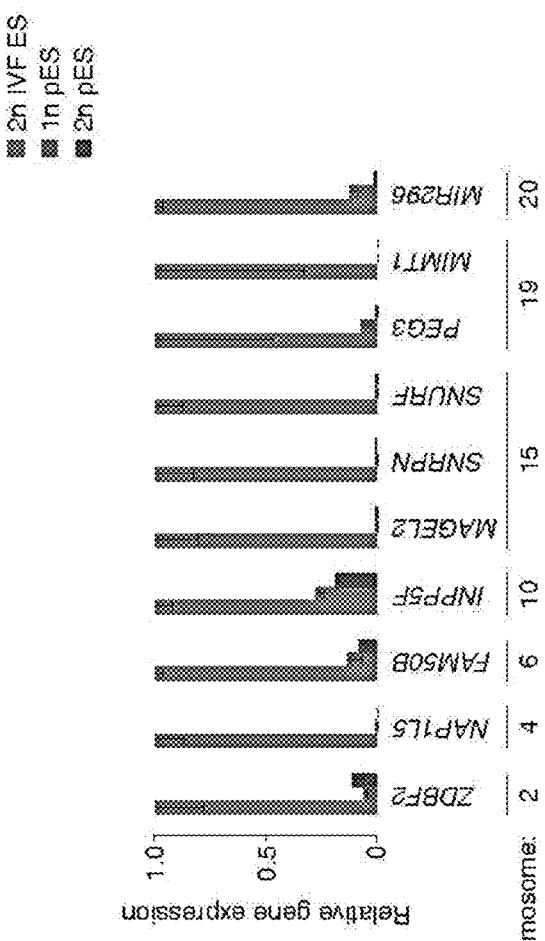
Figure 8D:
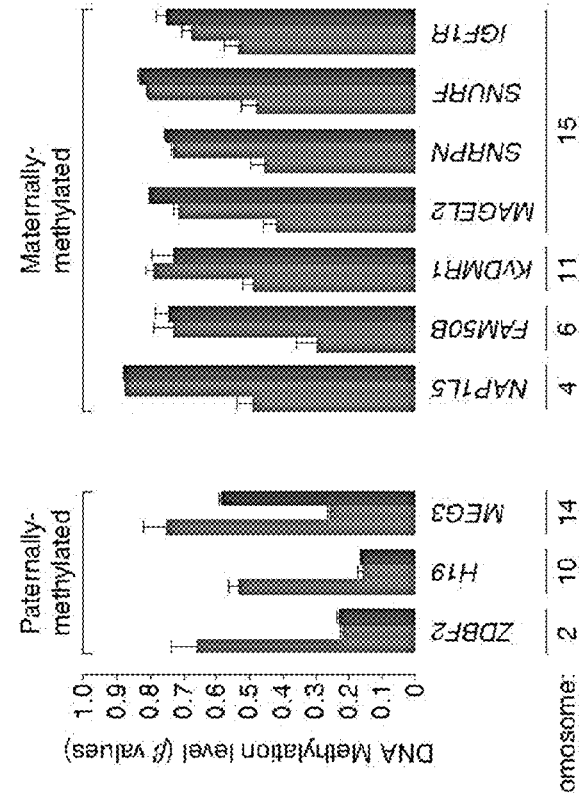
Figure 8A:
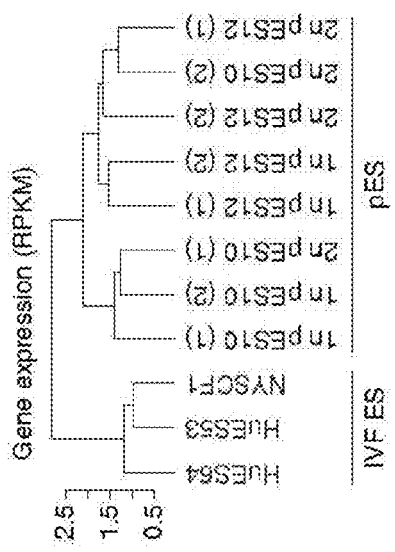
Figure 8B:
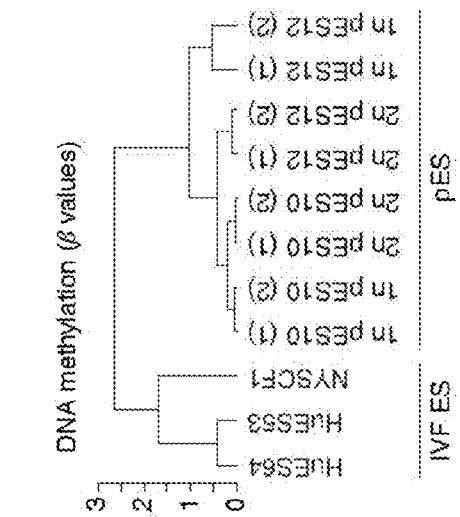
Figure 8E:
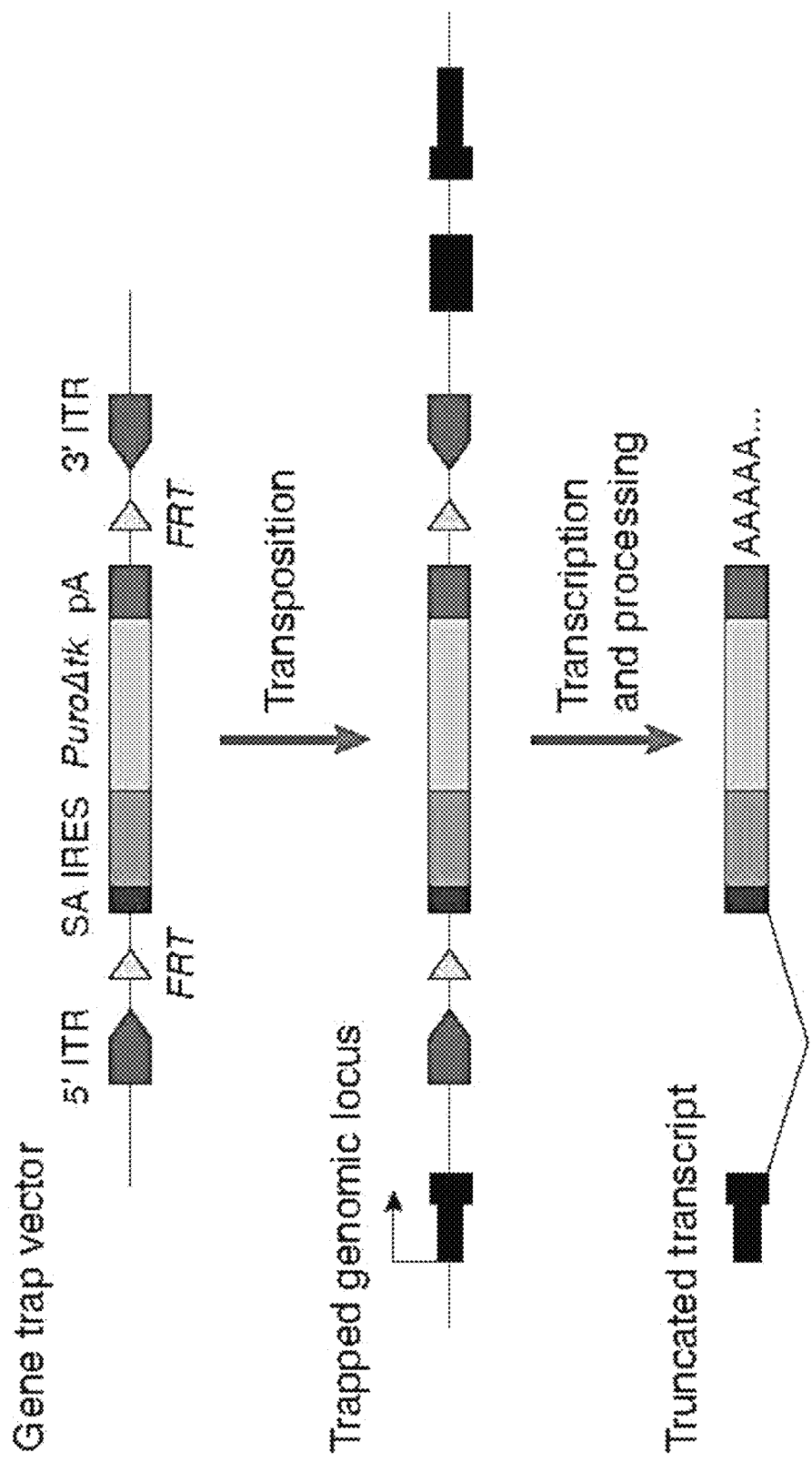

FIGS. 8A-E show analysis of parental imprinting and gene trap mutagenesis in haploid human parthenogenetic ES cells. FIG. 8A and FIG. 8B show hierarchical clustering analysis of diploid (2n) in vitro fertilization (IVF) ES cells and G1-sorted haploid (1n) and diploid parthenogenetic ES (pES) cells by expression levels of imprinted genes (n=75, see Table 6) (FIG. 8A) and DNA methylation levels at imprinted differentially methylated regions (iDMRs, n=35)[37] (FIG. 8B). (1) and (2) denote biological replicates. FIG. 8C shows relative mean expression levels±s.e.m. of representative paternally-expressed imprinted genes across seven chromosomes in the samples shown in FIG. 8a (RPKM ratios). FIG. 8D shows mean DNA methylation levels±s.e.m. at representative paternally-methylated and maternally-methylated iDMRs (typically intermediately methylated in bi-parental control cells, and respectively hypomethylated and hypermethylated in parthenogenetic cells) in the samples shown in FIG. 8B. β values range from complete hypomethylation (0) to complete hypermethylation (1). FIG. 8E shows a schematic outline of the piggyBac gene trap system. The gene trap vector[52] is flanked by piggyBac inverted terminal repeats (ITRs) and FRT sites, and carries a 5' splice acceptor (SA), an internal ribosome entry site (IRES) element followed by a promoterless puromycin resistance gene (Purodtk) and a 3' poly(A) signal (pA). In the presence of the PiggyBac transposase (encoded on a separate plasmid[53]), the gene trap vector undergoes random transposition into the genome. Insertion into a transcriptionally active gene results in truncation of the endogenous transcript and introduction of resistance to puromycin. ITR: inverted terminal repeat; FRT: flox sites.

FIGS. 9A-I show comparative analyses of isogenic haploid and diploid human ES cells. FIG. 9A shows sorting purity of haploid (1n) and diploid (2n) ES cells in G1. FIG. 9B shows log-scaled volcano plots of relative differential gene expression between haploid and diploid human ES cells, divided into panels by all genes (top), autosomal genes (middle) and X chromosomal genes (bottom). Q: false discovery rate (FDR). Significantly downregulated and upregulated genes (>2-fold change, Q<0.05) in haploid cells are marked in red and blue, respectively, and their totals are indicated to the right. Note that XIST is the most downregulated transcript in haploid cells. FIG. 9C shows smoothed distributions of the 1n/2n gene expression ratios for all expressed genes, all expressed autosomal genes and all expressed X chromosomal genes (expression threshold, mean RPKM>0.1). FIG. 9D shows a genome-wide moving median plot of the gene expression ratio between haploid and diploid pE10 cells in G1 by expression microarray analysis (window size=100 genes). FIG. 9E and FIG. 9F show a model for genome-wide autosomal gene level reduction in haploid human ES cell as inferred by differential XCI status. FIG. 9E shows that DNA content, RNA expression levels relative to total RNA, and presumed equality of absolute X chromosomal gene dosage in haploid ($X_a$) and diploid ($X_a X_i$) human ES cells enable the estimation of total RNA levels per haploid cell. $X_a$ and $X_i$ denote active (blue) and inactive (red) X chromosomes, respectively. A: autosomes; X: X chromosome; R: total RNA. FIG. 9F shows schematic genome-wide representation of relative and absolute RNA levels in the cells shown in FIG. 9e. FIG. 9G shows average diameter and calculated surface area and volume of G1-sorted haploid and diploid ES cells. Error bars represent s.d. (n=4-8). *P<0.01 (two-tailed unpaired Student's t test). FIG. 9H and FIG. 9I show functional annotation enrichment analysis for relatively downregulated genes and differentially methylated regions (DMRs) (FIG. 9H) as well as relatively upregulated genes (FIG. 9I) in haploid ES cells compared with diploid ES cells.

Figures 10A, 10B:
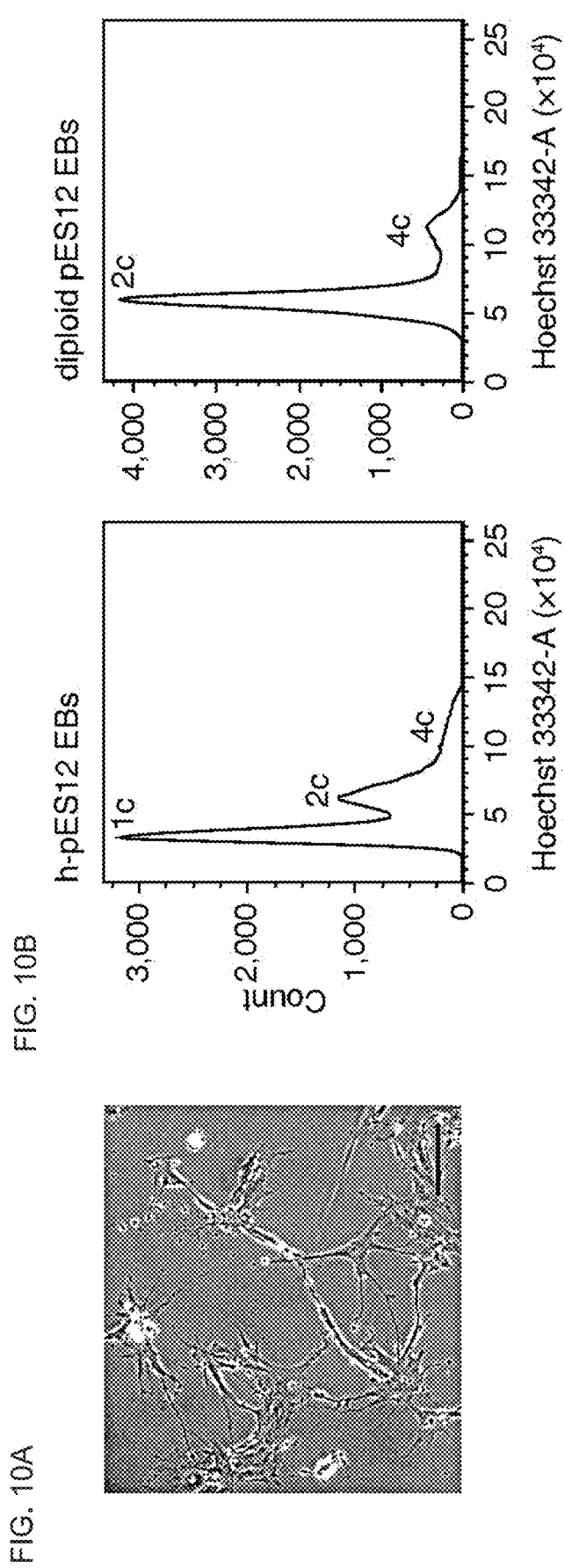
Figure 10C:
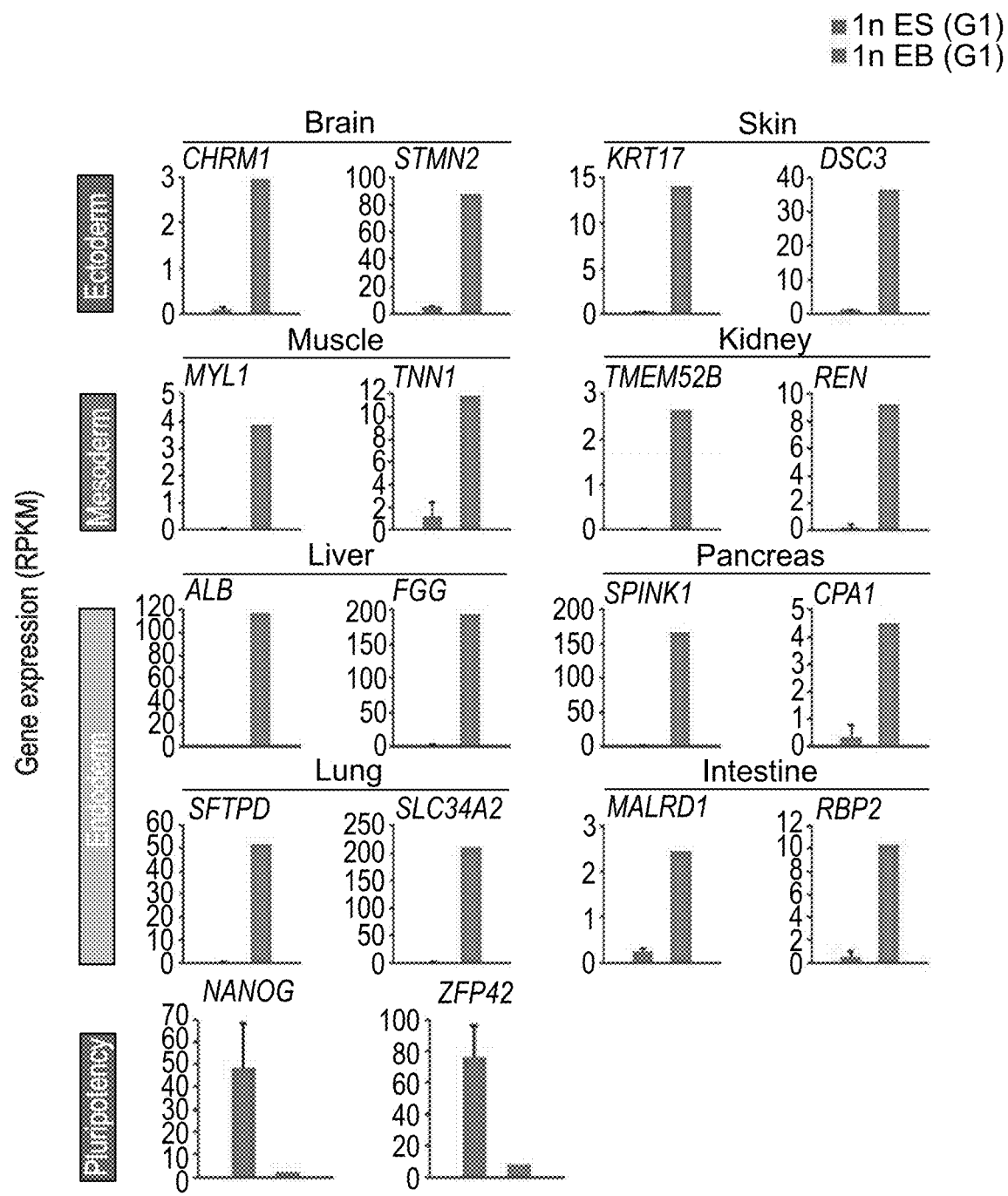

FIGS. 10A-C show EB differentiation of haploid human ES cells. FIG. 10A shows a representative image of plated cells dissociated from h-pES12-derived 21-day EBs, the karyotype of which is presented in FIG. 4b. Scale bar=100 μm. FIG. 10B shows DNA content profiles of dissociated EBs derived from haploid-enriched and diploid pES12 cells. c: chromosomal copies. FIG. 10C shows expression levels (RPKM) of tissue- and pluripotency-specific genes in undifferentiated (ES) and differentiated (EB) G1-sorted haploid (1n) pES10 cells.

FIGS. 11A-I show directed differentiation of haploid human ES cells. FIG. 11A and FIG. 11B show flow cytometry analysis with co-staining of DNA and NCAM1 in h-pES10 cells following neural differentiation. FIG. 11A shows gating for NCAM1-positive cells (right panel) based on a negative secondary-antibody-stained control sample (left panel). FIG. 11B shows DNA content profile of the entire cell population (related to FIG. 4e). c: chromosomal copies. FIG. 11C shows expression levels (RPKM) of neural-specific genes in G1-sorted haploid (1n) pES10 ES cells and NPCs. FIG. 11D shows XIST expression levels in haploid and diploid (2n) pES10-derived EBs and NPCs. FIG. 11E shows TUJ1 staining in h-pES12-derived neurons. Scale bar=100 μm. FIG. 11F shows DNA FISH on the neurons shown in FIG. 11E. Magnified insets show representative haploid and diploid nuclei with single and double hybridization signals, respectively. Scale bar=10 μm. FIG. 11G shows TNNT2 staining in G1-sorted haploid pES12-derived cardiomyocytes. Scale bar=10 μm. FIG. 11H and FIG. 11I show flow cytometry analysis with co-staining of DNA and PDX1 in h-pES10 cells following pancreatic differentiation. FIG. 11H shows gating for PDX1-positive cells (right panel) based on a negative secondary-antibody-stained control sample (left panel). FIG. 11I shows DNA content profile of the entire cell population (related to FIG. 4m). c: chromosomal copies.

Figure 12B:
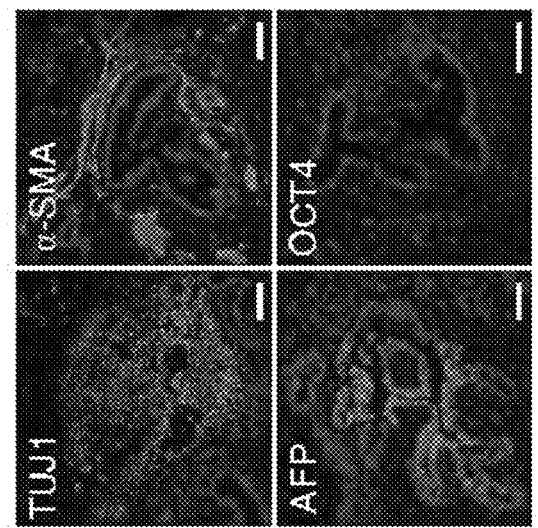
Figure 12A:
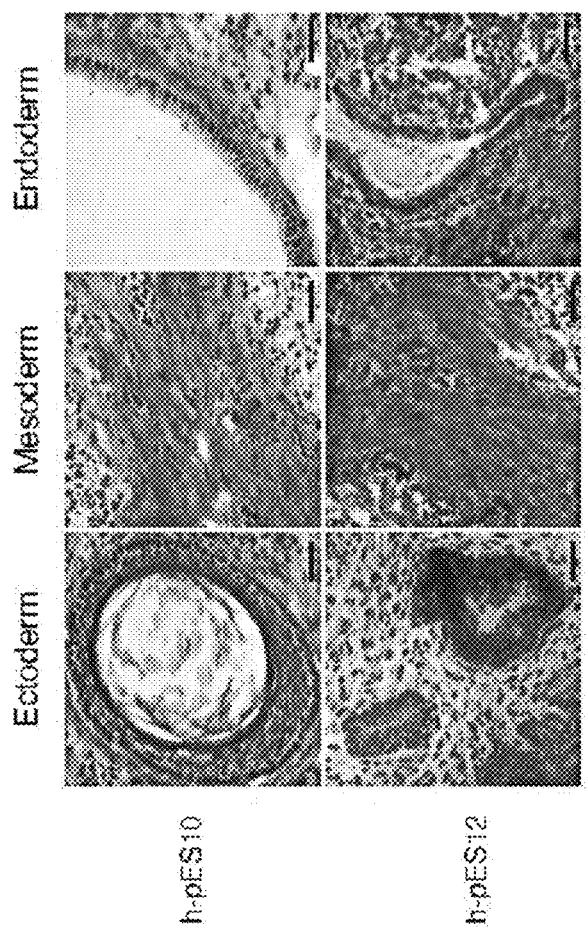

FIGS. 12A-B show in vivo differentiation of haploid human ES cells. FIG. 12A shows hematoxylin and eosin histological sections of teratomas derived from h-pES10 and h-pES12. Scale bar=50 μm. FIG. 12B shows TUJ1 (ectoderm), α-SMA (mesoderm), AFP (endoderm) and OCT4 (pluripotency) staining in an h-pES10-derived teratoma. DNA staining is shown in blue. Note the absence of nuclear OCT4 staining. Scale bars=100 μm.

Figure 13:
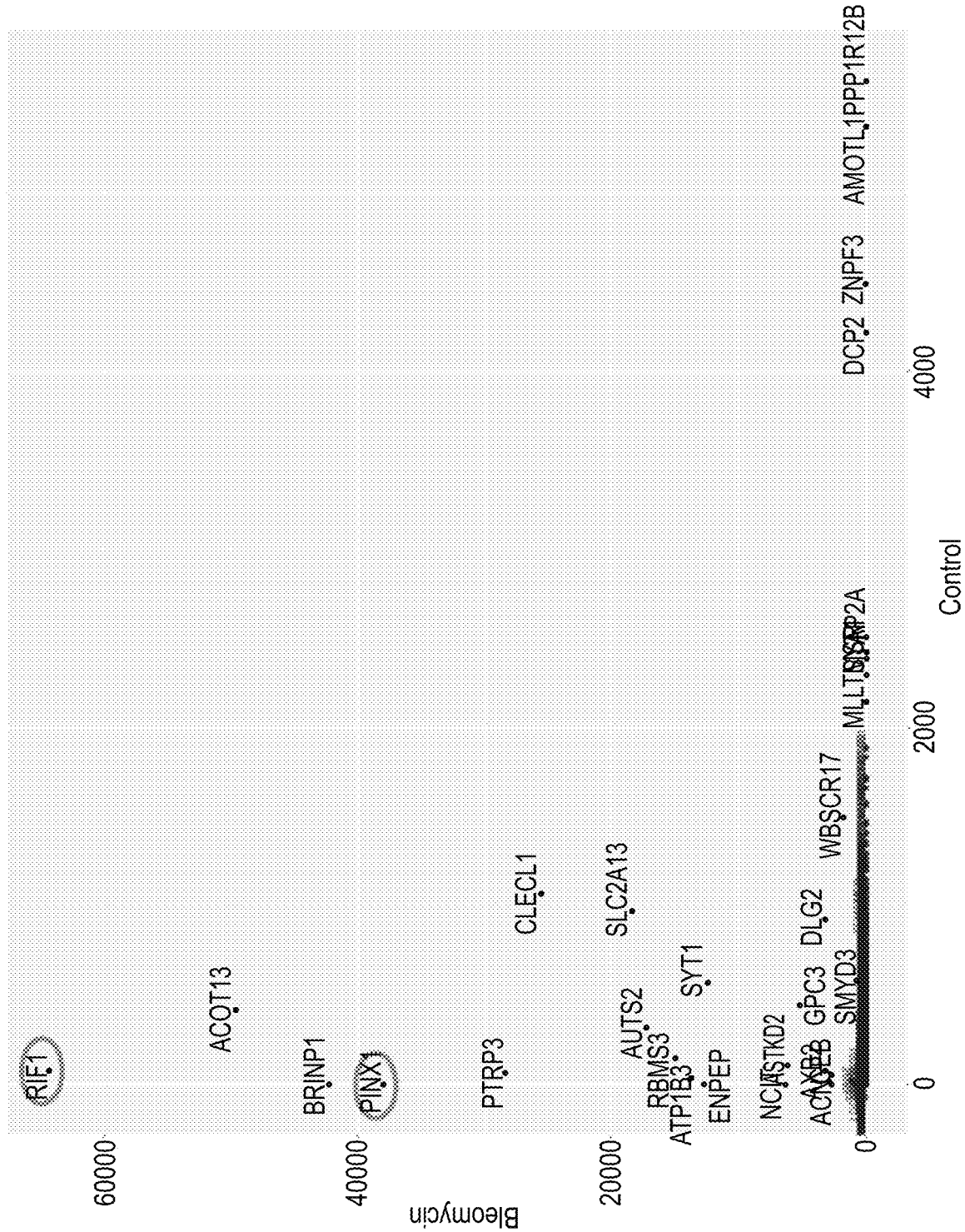

FIG. 13 represents an analysis of enrichment of genes that their mutation confer resistance to Bleomycin.

Figure 14:
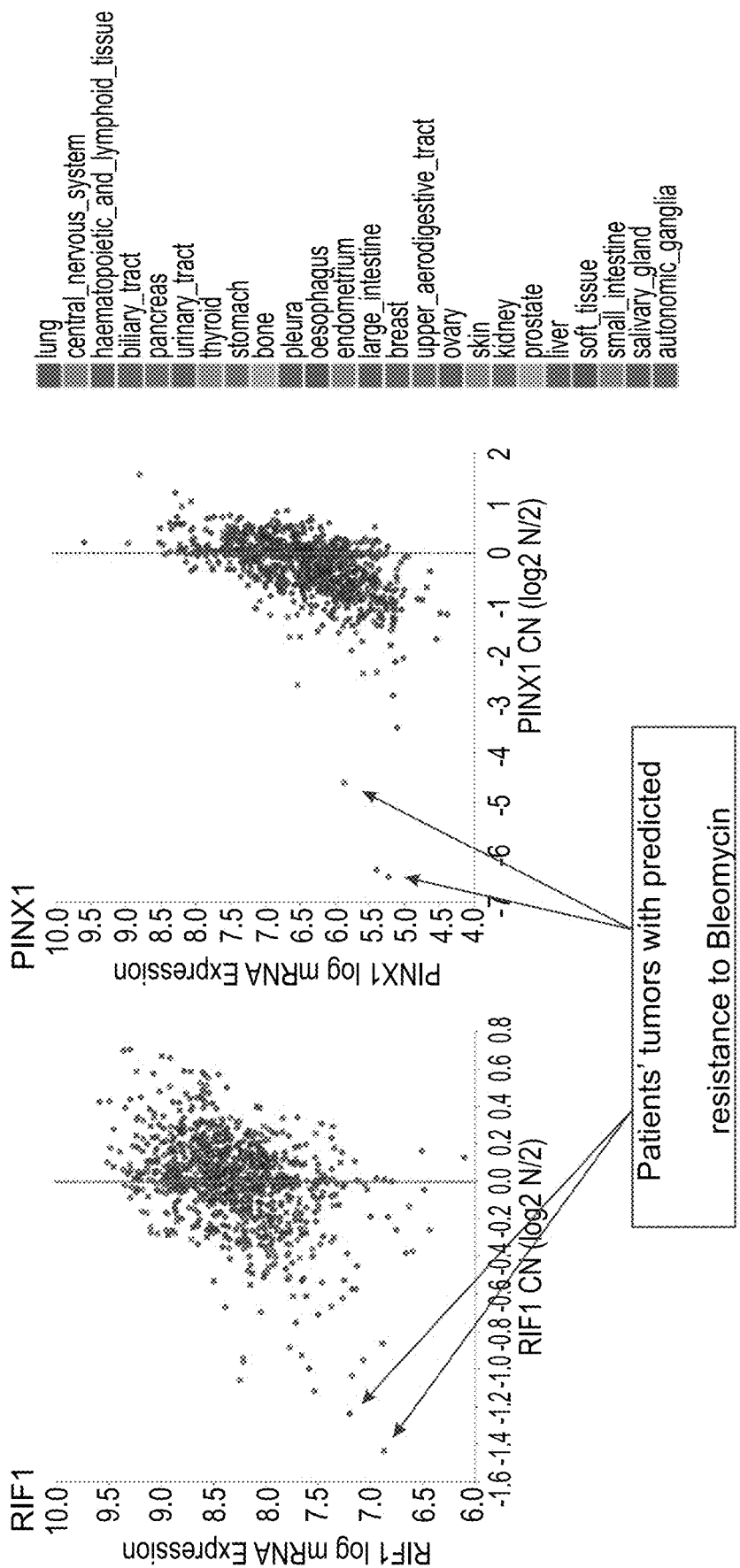

FIG. 14 are graphs illustrating the analysis of multiple tumors for deletion in genes that confer resistance to Bleomycin.

DESCRIPTION OF SPECIFIC EMBODIMENTS OF THE INVENTION

The present invention, in some embodiments thereof, relates to personalized medicine and more specifically to methods of selecting an appropriate therapy for treatment of disease in a subject so as to minimize the chances of drug resistance.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Cancer mortality is usually caused by incurable drug-resistant cancers. Although tremendous progress has been made in anticancer drug development during the past two decades, cancer medicine still faces unprecedented challenges associated with choosing effective treatments for individual patients.

The present inventors propose taking advantage of human haploid embryonic stem cells (ESCs) and cells differentiated therefrom, to select a therapy for the treatment of cancer in a personalized fashion. Specifically, the present inventors propose use of forward genetic screens with these cells to uncover gene candidates which are responsible for resistance to chemotherapeutic agents. Armed with this knowledge, the present inventors propose analyzing tumors of the subject for expression of these genes in order to avoid treatment with non-effective drugs. Furthermore, this knowledge may help stratify patient populations in clinical trials.

Whilst reducing the present invention to practice the present inventors uncovered a set of about 20 genes which are associated with bleomycin resistance. Two of these genes (RIF1 and PINX1) are involved in DNA damage response and telomerase length (FIG. 13).

The present inventors then analyzed multiple tumors and showed that some of them present deletion and/or absence of expression of these two genes, suggesting that these particular tumors would be resistant to bleomycin (FIG. 14).

Thus, according to a first aspect of the present invention, there is provided a method of selecting an agent for treating a disease of a subject comprising:

(a) exposing a plurality of haploid human embryonic stem (ES) cells to a cytotoxic therapy, wherein at least a portion of said plurality of haploid ES cells comprises a distinct artificially inactivated or overactivated gene;

(b) selecting a cell of said plurality of haploid human embryonic stem (ES) cells which shows resistance to said cytotoxic therapy;

(c) identifying in said cell said distinct artificially inactivated gene or overactivated gene; and (d) analyzing the sequence and/or expression of said distinct artificially inactivated gene or activated gene in a cell sample of the subject, wherein an alteration in the sequence and/or level of expression of said gene as compared to the sequence and/or expression of said gene in a control sample is indicative that the agent should be ruled out as a monotherapy for treating the disease in the subject.

According to another aspect of the present invention there is provided a method of selecting an agent for treating a disease comprising:

(a) exposing a plurality of human haploid cells to a cytotoxic therapy, wherein said cells were differentiated from haploid human embryonic stem (ES) cells, and wherein at least a portion of said plurality of cells comprises a distinct artificially inactivated or overactivated gene;

(b) selecting a cell of said plurality of cells which shows resistance to said cytotoxic therapy; and (c) identifying in said cell said distinct artificially inactivated or overactivated gene.

As used herein, the phrase "stem cells" refers to cells which are capable of remaining in an undifferentiated state (e.g., pluripotent or multipotent stem cells) for extended periods of time in culture until induced to differentiate into other cell types having a particular, specialized function (e.g., fully differentiated cells).

The phrase "embryonic stem cells" refers to pluripotent embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation.

As used herein, "haploid cell" refers to a cell, e.g., an oocyte, blastomer, embryonic stem cell or differentiated embryonic stem cell, having a haploid DNA content, wherein the haploid DNA is of all male or all female origin, preferably female origin. Similarly, a haploid (parthenogenetic) blastomere, morula or blastocyst, or an embryonic stem cell or cell line or cell population of the invention are characterized by a haploid DNA content. As used herein "haploid DNA" refers to 23 chromosomes of all male or all female origin in human. As shown in the following examples, haploid human embryonic stem cells may be generated from artificially activated human oocytes. The haploid ES cells are then sorted based on cell ploidy so as to produce an enriched population of haploid human ES cells.

As used herein, the term "isolated cell" or "isolated (haploid) embryonic stem cell" refers generally to a cell that is not associated with one or more cells or one or more cellular components with which the cell is associated in vivo. For example, an isolated cell may have been removed from its native environment, or may result from propagation, e.g., ex vivo propagation, of a cell that has been removed from its native environment.

The term "oocyte" as used herein means a female gametocyte or germ cell involved in reproduction. The oocyte may be an immature ovum, or an egg cell. An oocyte is produced in the ovary during female gametogenesis. Methods for isolation of oocytes are well known in the art. Essentially, this will comprise isolating oocytes from the ovaries or reproductive tract of a female subject (see for example "Principles and Practice of Fertility Preservation", Cambridge University Press 2011, edited by J. Donnez and S. S. Kim).

Oocytes used in the context of the present invention are obtained from a human female subject. The oocyte can be a non-fertilized and immature oocyte or a non-fertilized and mature oocyte. Preferably, the oocyte is a non-fertilized and immature oocyte. Said immature oocytes can be matured in vitro by methods described in the literature (see exemplarily Krotz et al. 2010).

In one embodiment of the method of the invention, unfertilized and immature oocytes are isolated and then matured in vitro, prior to the activation.

As used herein, the phrase "activation of an oocyte" refers to a process wherein an unfertilized oocyte is (preferably exogenously) activated such that it undergoes a process typically including separation of the chromatid pairs and extrusion of the second polar body, resulting inter alia in oocytes having a haploid number of chromosomes, each with one chromatid. "Activation" also includes methods whereby a cell containing DNA of all female origin is induced to develop into an embryo that has a discernible inner cell mass and trophectoderm, which is useful for producing pluripotent embryonic stem cells. Embodiments of the invention also include activation of oocytes or blastomere cells such as inner cell mass cells or trophoblast cells that have been transplanted with a male (androgenesis) or a female haploid nucleus (gynogenesis).

An "activated oocyte" as used herein, refers to an unfertilized and optionally mature(d) oocyte which has been parthenogenetically activated or androgenetically activated. Parthenogenetic techniques involve the activation of the oocyte using an electrical pulse, a calcium ionophore, a kinase inhibitor, a translation inhibitor or a combination of these. For instance, human oocytes can be activated as described in the Examples section herein below. Androgenetic techniques involve the fertilization of an enucleated oocyte with a sperm, typically by intracytoplasmic sperm injection. The genome of the oocyte is removed before or after fertilization of the oocyte to generate a cell that contains only the sperm genome. The oocyte may be exposed to an activation stimulus as for parthenogenesis.

Following activation, the oocyte begins to divide and differentiate in a programmed fashion until a blastocyst is generated which has the structure of a 5 day embryo.

Appropriate culture conditions for the generation of morulae and blastocysts derived from activated oocytes are described in the art (for example Sagi et al., Nature 532, pages 107-111, 2016).

The inner cell mass is then removed (isolated) from the blastocyst e.g. by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated.

Further details of generating the human haploid ES cells are provided in the Examples section herein below and in Sagi et al., Nature 532, pages 107-111, 2016.

Once generated, the haploid human ES cells are maintained in culture. Preferably, the haploid cells are selected from the culture or sorted in the culture. The haploid cells may be identified by metaphase spread analysis or sorting of cells with less than 2 chromosomal copies. In some embodiments, the sorting step is based on cell ploidy or cell surface markers and comprises at least one cycle of flow cytometry, preferably, fluorescence-activated cell sorting (FACS). Haploid cells can also be identified by flow cytometry, centromere protein immunofluorescence staining, or DNA fluorescence in situ hybridization (FISH). Other cell sorting techniques known in the art, for example, magnetic-activated cells sorting (MACS), can also be used in the methods of the invention.

The haploid human ES cells and cells lines of the invention may be maintained "in culture," for example under standard human ES cell growth conditions. According to one embodiment, culture is carried out on a feeder layer of arrested mouse embryonic fibroblasts in gelatin-coated plates in medium containing Knockout Dulbecco's Modified Eagle's Medium (Gibco, Life Technologies) supplemented with 15% Knockout Serum Replacement (KSR; Gibco, Life Technologies), 2 mM L-glutamine, 0.1 mM nonessential amino acids, penicillin and streptomycin (50 units mL-1 and 50 µg mL-1, respectively), 0.1 mM β-mercaptoethanol and 8 ng mL-1 basic fibroblast growth factor. Cells can be maintained in a humidified incubator at 37° C. and 5% $CO_2$ and passaged every 3-5 days using Trypsin Solution A without EDTA. Preferably, haploid human ES cells are maintained in culture for at least two passages, three passages, at least four passages, at least five passages, at least seven passages, at least ten passages, at least twenty passages, or at least thirty passages. Preferably, haploid human ES cells are maintained in culture for at least about ten days, at least about twenty days, at least about thirty days, at least about forty-five days, at least about sixty days, at least about three months, at least about four months, or at least about six months.

The term "cell lines" refers to cells that can grow in culture for many passages, and can be enriched for haploid cells by cell sorting. In accordance with one example of the invention, the cell lines are cultured under standard human ES cell growth conditions and occasional enrichment of the haploid fraction by sorting every 3 to 5 passages.

As used herein, the term "enriched population" refers to a percentage of haploid cells in a total cell population that is greater than 1%, preferably greater than 5%, 10%, 15%, 20%, 25%, 30%, 35%, 40%, 45%, 50%, 55%, 60%, 65%, 70%, 75%, 80%, 85%, or 90%. Typically, an enriched population can be obtained after a single cycle of sorting, such as FACS.

The term "substantially pure" refers to a percentage of haploid cells in a total cell population that is above 90%, preferably above 91%, 92%, 93%, 94%, 95%, 96%, 97%, 98%, or 99%. Most preferably, a substantially pure population is a confluent population of haploid cells.

Optionally, the human haploid embryonic stem cells may be differentiated (ex vivo) along a particular cell lineage. The inventors have demonstrated that differentiated cells can be produced from embryoid bodies differentiated from haploid human ES cells, or by directed differentiation of haploid human ES cells toward a particular lineage.

Following is a non-limiting description of a number of procedures and approaches for inducing differentiation of EBs to lineage specific cells.

Neural Precursor Cells

To differentiate the EBs of some embodiments of the invention into neural precursors, four-day-old EBs are cultured for 5-12 days in tissue culture dishes including DMEM/F-12 medium with 5 mg/ml insulin, 50 mg/ml transferrin, 30 nM selenium chloride, and 5 mg/ml fibronectin (ITSFn medium, Okabe, S. et al., 1996, Mech. Dev. 59: 89-102). The resultant neural precursors can be further transplanted to generate neural cells in vivo (Brüstle, O. et al., 1997. In vitro-generated neural precursors participate in mammalian brain development. Proc. Natl. Acad. Sci. USA. 94: 14809-14814). It will be appreciated that prior to their transplantation, the neural precursors are trypsinized and triturated to single-cell suspensions in the presence of 0.1% DNase.

Oligodendrocytes and Myelinate Cells

EBs of some embodiments of the invention can differentiate to oligodendrocytes and myelinate cells by culturing the cells in modified SATO medium, i.e., DMEM with bovine serum albumin (BSA), pyruvate, progesterone, putrescine, thyroxine, triiodothryonine, insulin, transferrin, sodium selenite, amino acids, neurotrophin 3, ciliary neurotrophic factor and Hepes (Bottenstein, J. E. & Sato, G. H., 1979, Proc. Natl. Acad. Sci. USA 76, 514-517; Raff, M. C., Miller, R. H., & Noble, M., 1983, Nature 303: 390-396]. Briefly, EBs are dissociated using 0.25% Trypsin/EDTA (5 min at 37° C.) and triturated to single cell suspensions. Suspended cells are plated in flasks containing SATO medium supplemented with 5% equine serum and 5% fetal calf serum (FCS). Following 4 days in culture, the flasks are gently shaken to suspend loosely adhering cells (primarily oligodendrocytes), while astrocytes are remained adhering to the flasks and further producing conditioned medium. Primary oligodendrocytes are transferred to new flasks containing SATO medium for additional two days. Following a total of 6 days in culture, oligospheres are either partially dissociated and resuspended in SATO medium for cell transplantation, or completely dissociated and a plated in an oligosphere-conditioned medium which is derived from the previous shaking step [Liu, S. et al., (2000). Embryonic stem cells differentiate into oligodendrocytes and myelinate in culture and after spinal cord transplantation. Proc. Natl. Acad. Sci. USA. 97: 6126-6131].

Mast Cells

For mast cell differentiation, two-week-old EBs of some embodiments of the invention are transferred to tissue culture dishes including DMEM medium supplemented with 10% FCS, 2 mM L-glutamine, 100 units/ml penicillin, 100 mg/ml streptomycin, 20% (v/v) WEHI-3 cell-conditioned medium and 50 ng/ml recombinant rat stem cell factor (rrSCF, Tsai, M. et al., 2000. In vivo immunological function of mast cells derived from embryonic stem cells: An approach for the rapid analysis of even embryonic lethal mutations in adult mice in vivo. Proc Natl Acad Sci USA. 97: 9186-9190). Cultures are expanded weekly by transferring the cells to new flasks and replacing half of the culture medium.

Hemato-Lymphoid Cells

To generate hemato-lymphoid cells from the EBs of some embodiments of the invention, 2-3 days-old EBs are transferred to gas-permeable culture dishes in the presence of 7.5% $CO_2$ and 5% $O_2$ using an incubator with adjustable oxygen content. Following 15 days of differentiation, cells are harvested and dissociated by gentle digestion with Collagenase (0.1 unit/mg) and Dispase (0.8 unit/mg), both are available from F.Hoffman-La Roche Ltd, Basel, Switzerland. CD45-positive cells are isolated using anti-CD45 monoclonal antibody (mAb) M1/9.3.4.HL.2 and paramagnetic microbeads (Miltenyi) conjugated to goat anti-rat immunoglobulin as described in Potocnik, A. J. et al., (Immunology Hemato-lymphoid in vivo reconstitution potential of subpopulations derived from in vitro differentiated embryonic stem cells. Proc. Natl. Acad. Sci. USA. 1997, 94: 10295-10300). The isolated CD45-positive cells can be further enriched using a single passage over a MACS column (Miltenyi).

It will be appreciated that since EBs are complex structures, differentiation of EBs into specific differentiated cells, tissue or organ may require isolation of lineage specific cells from the EBs.

Such isolation may be effected by sorting of cells of the EBs via fluorescence activated cell sorter (FACS) or mechanical separation of cells, tissues and/or tissue-like structures contained within the EBs.

Methods of isolating EB-derived-differentiated cells via FACS analysis are known in the art. According to one method, EBs are disaggregated using a solution of Trypsin and EDTA (0.025% and 0.01%, respectively), washed with 5% fetal bovine serum (FBS) in phosphate buffered saline (PBS) and incubated for 30 min on ice with fluorescently-labeled antibodies directed against cell surface antigens characteristics to a specific cell lineage. For example, endothelial cells are isolated by attaching an antibody directed against the platelet endothelial cell adhesion molecule-1 (PECAM1) such as the fluorescently-labeled PECAM1 antibodies (30884X) available from PharMingen (PharMingen, Becton Dickinson Bio Sciences, San Jose, CA, USA) as described in Levenberg, S. et al., (Endothelial cells derived from human embryonic stem cells. Proc. Natl. Acad. Sci. USA. 2002. 99: 4391-4396). Hematopoietic cells are isolated using fluorescently-labeled antibodies such as CD34-FITC, CD45-PE, CD31-PE, CD38-PE, CD90-FITC, CD117-PE, CD15-FITC, class I-FITC, all of which IgG1 are available from PharMingen, CD133/1-PE (IgG1) (available from Miltenyi Biotec, Auburn, CA), and glycophorin A-PE (IgG1), available from Immunotech (Miami, FL). Live cells (i.e., without fixation) are analyzed on a FACScan (Becton Dickinson Bio Sciences) by using propidium iodide to exclude dead cells with either the PC-LYSIS or the CELL-QUEST software. It will be appreciated that isolated cells can be further enriched using magnetically-labeled second antibodies and magnetic separation columns (MACS, Miltenyi) as described by Kaufman, D. S. et al., (Hematopoietic colony-forming cells derived from human embryonic stem cells. Proc. Natl. Acad. Sci. USA. 2001, 98: 10716-10721).

An example for mechanical isolation of beating cardiomyocytes from EBs is disclosed in U.S. Pat. Appl. No. 20030022367 to Xu et al. Briefly, four-day-old EBs of some embodiments of the invention are transferred to gelatin-coated plates or chamber slides and are allowed to attach and differentiate. Spontaneously contracting cells, which are observed from day 8 of differentiation, are mechanically separated and collected into a 15-mL tube containing low-calcium medium or PBS. Cells are dissociated using Collagenase B digestion for 60-120 minutes at 37° C., depending on the Collagenase activity. Dissociated cells are then resuspended in a differentiation KB medium (85 mM KCl, 30 mM $K_2HPO_4$, 5 mM $MgSO_4$, 1 mM EGTA, 5 mM creatine, 20 mM glucose, 2 mM $Na_2ATP$, 5 mM pyruvate, and 20 mM taurine, buffered to pH 7.2, Maltsev et al., Circ. Res. 75:233, 1994) and incubated at 37° C. for 15-30 min. Following dissociation cells are seeded into chamber slides and cultured in the differentiation medium to generate single cardiomyocytes capable of beating.

It will be appreciated that the culturing conditions suitable for the differentiation and expansion of the isolated lineage specific cells include various tissue culture medium, growth factors, antibiotic, amino acids and the like and it is within the capability of one skilled in the art to determine which conditions should be applied in order to expand and differentiate particular cell types and/or cell lineages [reviewed in Fijnvandraat A C, et al., Cardiovasc Res. 2003; 58: 303-12; Sachinidis A, et al., Cardiovasc Res. 2003; 58: 278-91; Stavridis M P and Smith A G, 2003; Biochem Soc Trans. 31(Pt 1): 45-9].

Cell lines of some embodiments of the invention can be produced by immortalizing the EB-derived cells by methods known in the art, including, for example, expressing a telomerase gene in the cells (Wei, W. et al., 2003. Mol Cell Biol. 23: 2859-2870) or co-culturing the cells with NIH 3T3 hph-HOX11 retroviral producer cells (Hawley, R. G. et al., 1994. Oncogene 9: 1-12).

Following are non-limiting examples of culturing conditions which are suitable for differentiating and/or expanding lineage specific cells from the haploid embryonic stem cells of the present invention.

Mesenchymal stromal cells which are CD73-positive and SSEA-4-negative can be generated from hESCs by mechanically increasing the fraction of fibroblast-like differentiated cells formed in cultures of hESCs, essentially as described in Trivedi P and Hematti P. Exp Hematol. 2008, 36(3):350-9. Briefly, to induce differentiation of hESC the intervals between medium changes are increased to 3-5 days, and the cells at the periphery of the ESC colonies become spindle-shaped fibroblast-looking cells. After 9-10 days under these conditions when about 40-50% of the cells in the culture acquire the fibroblast-looking appearance, the undifferentiated portions of ESC colonies are physically removed and the remaining differentiated cells are passaged to new culture plates under the same conditions.

To induce differentiation of hESCs into dopaminergic (DA) neurons, the cells can be co-cultured with the mouse stromal cell lines PA6 or MS5, or can be cultured with a combination of stromal cell-derived factor 1 (SDF-1/CXCL12), pleiotrophin (PTN), insulin-like growth factor 2 (IGF2) and ephrin B1 (EFNB1) essentially as described in Vazin T, et al., PLoS One. 2009 Aug. 12; 4(8):e6606; and in Elkabetz Y., et al., Genes Dev. 2008 Jan. 15; 22: 152-165.

To generate mesencephalic dopamine (mesDA) neurons, hESCs can be genetically modified to express the transcription factor Lmxla (e.g., using a lentiviral vector with the PGK promoter and Lmxla) essentially as described in Friling S., et al., Proc Natl Acad Sci USA. 2009, 106: 7613-7618.

To generate lung epithelium (type II pneumocytes) from hESCs, the ESCs can be cultured in the presence of a commercially available cell culture medium (Small Airway Growth Medium; Cambrex, College Park, MD), or alternatively, in the presence of a conditioned medium collected from a pneumocyte cell line (e.g., the A549 human lung adenocarcinoma cell line) as described in Rippon H J., et al., Proc Am Thorac Soc. 2008; 5: 717-722.

To induce differentiation of hESCs or human iPS cells into neural cells, the pluripotent stem cells can be cultured for about 5 days in the presence of a serum replacement medium supplemented with TGF-b inhibitor (SB431542, Tocris; e.g., 10 nM) and Noggin (R&D; e.g., 500 ng/ml), following which the cells are cultured with increasing amounts (e.g., 25%, 50%, 75%, changed every two days) of N2 medium (Li X J., et al., Nat Biotechnol. 2005, 23:215-21) in the presence of 500 ng/mL Noggin, essentially as described in Chambers S M., et al., Nat Biotechnol. 2009, 27: 275-280.

During differentiation the stem cells may be monitored for their differentiation state and or their ploidy status. Cell differentiation can be determined upon examination of cell or tissue-specific markers which are known to be indicative of differentiation. For example, primate ES cells may express the stage-specific embryonic antigen (SSEA) 4, the tumour-rejecting antigen (TRA)-1-60 and TRA-1-81.

Tissue/cell specific markers can be detected using immunological techniques well known in the art [Thomson J A et al., (1998). Science 282: 1145-7]. Examples include, but are not limited to, flow cytometry for membrane-bound markers, immunohistochemistry for extracellular and intracellular markers and enzymatic immunoassay, for secreted molecular markers.

Determination of ES cell differentiation can also be effected via measurements of alkaline phosphatase activity. Undifferentiated human ES cells have alkaline phosphatase activity which can be detected by fixing the cells with 4% paraformaldehyde and developing with the Vector Red substrate kit according to manufacturer's instructions (Vector Laboratories, Burlingame, California, USA).

The pluripotency of embryonic stem cells can be monitored in vitro by the formation of embryoid bodies (EBs) as well as in vivo via the formation of teratomas.

Isolation of Lineage Specific Cells from ESCs

As used herein, the phrase "isolating lineage specific cells" refers to the enrichment of a mixed population of cells in a culture with cells predominantly displaying at least one characteristic associated with a specific lineage phenotype. It will be appreciated that all cell lineages are derived from the three embryonic germ layers. Thus, for example, hepatocytes and pancreatic cells are derived from the embryonic endoderm, osseous, cartilaginous, elastic, fibrous connective tissues, myocytes, myocardial cells, bone marrow cells, vascular cells (namely endothelial and smooth muscle cells), and hematopoietic cells are differentiated from embryonic mesoderm and neural, retina and epidermal cells are derived from the embryonic ectoderm.

Lineage specific cells can be obtained by directly inducing the expanded, undifferentiated ESCs to culturing conditions suitable for the differentiation of specific cell lineage.

Thus, in one embodiment, the human haploid embryonic stem cells are differentiated into terminally differentiated cells (e.g., skin cells, neuronal cells, liver cells, pancreatic cells, ovarian cells, breast cells, retinal cells) or to cells with limited differentiation potential (e.g., precursors which are restricted to a specific cell lineage).

In some embodiments, the human haploid embryonic stem cells may be differentiated into multipotent haploid cells.

"Multipotent" haploid human cells of the invention are progenitor or stem cells that have the potential to develop into multiple, but not all, cell types. Neural stem cells, hematopoietic stem cells, and mesenchymal stem cells are non-limiting examples of multipotent cells.

Once generated, the haploid human cells of the invention are exposed to a mutagen so as to produce a mutant population of haploid human stem cells (e.g. haploid human embryonic stem cells). In one embodiment, the mutant population is a mutant library.

Mutagens suitable for use in the present invention include physical mutagens, such as ionizing radiation (X-rays, gamma rays, ultraviolet rays, etc.); chemical mutagens, such as alkylating agents; and biological agents, such as plasmid, phage, or viral vectors. Examples of biological agents include insertional vectors, for example, gene trap vectors, and technologies for site-directed mutagenesis, such as zinc-finger nucleases (ZFNs), transcription activator-like effector nucleases (TALENs), or the CRISPR/Cas9 system.

The present inventors contemplate generation of a mutant library, in which at least a portion (e.g. 5%, 10%, 20%, 30%, 40%, 50%, 60%, 70%, 80%, 90% or more) of the cells of the library have at least one distinct, artificially inactivated or activated gene. In one embodiment, at least a portion of the cells of the library have one artificially inactivated or activated gene. In another embodiment, at least a portion of the cells of the library have more than one (e.g. 2, 3, 4, 5 or more) artificially inactivated or activated gene.

The number of cells in the population (e.g. library) can vary. In some embodiments, the number of cells which are mutagenized is between $10^4$ and $10^{13}$ cells. In some embodiments the number of cells may be at least about $10^5$, $10^6$, $10^7$, $10^8$, $10^9$, $10^{10}$, $10^{11}$, $10^{12}$ cells, or more. In some embodiments, the number of cells mutagenized or screened is between $10^5$ and $10^{12}$ cells, e.g., at least $10^6$, $10^7$, $10^8$, $10^9$, $10^{10}$, $10^{11}$ and up to $10^{12}$. In some embodiments a mutagenesis or screen is performed using multiple populations of cells and/or is repeated multiple times. In some embodiments, the number of cells examined or assessed is between $10^5$ and $10^{12}$ cells, e.g., $10^6$, $10^7$, $10^8$, $10^9$, $10^{10}$, $10^{11}$ up to about $10^{12}$. In some embodiments smaller numbers of cells are of use, e.g., between 1-10$^4$ cells. In some embodiments a population of cells is contained in an individual vessel, e.g., a culture vessel such as a culture plate, flask, or well. In some embodiments a population of cells is contained in multiple vessels. In some embodiments two or more cell populations are pooled to form a larger population. In some embodiments the population of haploid human cells comprises cells that collectively have insertions in at least 50%, at least 75%, at least 90%, at least 95%, at least 96%, at least 97%, at least 98%, at least 99%, or 100% of the genes present in the cells.

The term "inactivate a gene" refers to a gene having an artificially altered nucleic acid sequence (e.g. a mutation) which brings about a down-regulation of expression thereof. In one embodiment, the artificially altered nucleic acid sequence of the gene ensures that a functional protein product of the gene is not expressed at all. In another embodiment, the artificially altered nucleic acid sequence of the gene ensures that the level of expression of a functional protein product of the gene is downregulated by at least 50%, 60%, 70%, 80%, 90%, 95% or more in comparison with the level in a control human haploid ESC which has not been exposed to an agent which artificially inactivates that gene.

The term "activate a gene" refers to a gene having an artificially altered nucleic acid sequence (e.g. a mutation) which brings about an up-regulation of expression thereof. In one embodiment, the artificially altered nucleic acid sequence of the gene ensures that the level of expression of a functional protein product of the gene is upregulated by at least 50%, 60%, 70%, 80%, 90%, 100%, 200% or more in comparison with the level in a control human haploid ESC which has not been exposed to an agent which artificially inactivates that gene.

According to one embodiment, genome editing may be performed using engineered endonucleases to inactivate or activate a gene. This approach refers to a reverse genetics method using artificially engineered nucleases to cut and create specific double-stranded breaks at a desired location(s) in the genome, which are then repaired by cellular endogenous processes such as, homology directed repair (HDS) and nonhomologous end-joining (NFfEJ). NFfEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Meganucleases—

Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8,163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—

Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is FokI. Additionally FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break. Repair of these double-stranded breaks through the nonhomologous end-joining (NHEJ) pathway most often results in small deletions or small sequence insertions. Since each repair made by NHEJ is unique, the use of a single nuclease pair can produce an allelic series with a range of different deletions at the target site. The deletions typically range anywhere from a few base pairs to a few hundred base pairs in length, but larger deletions have successfully been generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, CA).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www.talendesign.org). TALEN can also be designed and obtained commercially from e.g., Sangamo Biosciences™ (Richmond, CA).

CRISPR-Cas System—

Many bacteria and archea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components. The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. *Science* (2012) 337: 816-821.). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded brakes in a variety of different species (Cho et al., 2013; Cong et al., 2013; DiCarlo et al., 2013; Hwang et al., 2013a,b; Jinek et al., 2013; Mali et al., 2013).

The CRIPSR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded brakes produced by CRISPR/Cas can undergo homologous recombination or NHEJ.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder Flexible algorithm for identifying specific Cas9 targets in genomes and the CRISPR Optimal Target Finder.

In order to use the CRISPR system, both gRNA and Cas9 should be expressed in a target cell. The insertion vector can contain both cassettes on a single plasmid or the cassettes are expressed from two separate plasmids. CRISPR plasmids are commercially available such as the px330 plasmid from Addgene.

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, electroporated into the cells, and positive selection is performed to isolate homologous recombinants. These homologous recombinants contain a local duplication that is separated by intervening vector sequence, including the selection cassette. In the second step, targeted clones are subjected to negative selection to identify cells that have lost the selection cassette via intrachromosomal recombination between the duplicated sequences. The local recombination event removes the duplication and, depending on the site of recombination, the allele either retains the introduced mutation or reverts to wild type. The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After electroporation and positive selection, homologously targeted clones are identified. Next, a second targeting vector that contains a region of homology with the desired mutation is electroporated into targeted clones, and negative selection is applied to remove the selection cassette and introduce the mutation. The final allele contains the desired mutation while eliminating unwanted exogenous sequences.

According to a particular embodiment, the mutant population is generated by insertional mutagenesis. In some embodiments insertional mutagenesis is accomplished by introducing a gene trap vector into the haploid human cells of the present invention.

The term "gene trap vector" refers to a vector that comprises a nucleic acid construct capable of inserting into and potentially inactivating an endogenous cellular gene, e.g., a gene in the nucleus of a mammalian cell. Typically, insertion of the nucleic acid construct into the gene both disrupts the gene and facilitates its identification and/or isolation. A cell having such an insertion is considered a "mutant cell". The inserted nucleic acid serves as a "molecular tag" that can be used to isolate or otherwise identify endogenous genomic DNA located nearby, as discussed further below. In some embodiments the nucleic acid construct comprises DNA that encodes a reporter molecule ("reporter") that, when expressed, allows identification of a cell that contains the construct inserted into its genome. Such DNA may be referred to as a "reporter gene". In some embodiments the reporter molecule facilitates detection and/or isolation of a cell that contains the construct. In some embodiments the construct lacks a genetic element, such as a promoter or a polyadenylation (polyA) sequence, which element is normally required for expression or that significantly increases expression, so that effective expression of the reporter following introduction of the vector into a cell occurs only if the construct inserts into an endogenous gene. Examples of reporters are discussed herein. For example, in some embodiments a readily detectable protein, such as a fluorescent protein or enzyme, may be used. In some embodiments a selectable marker is used. In some embodiments activity of a reporter is used to identify a cell having a gene trap construct insertion in an endogenous gene.

Gene trap vectors of a variety of different designs may be used in various embodiments. Various gene trap vectors are described in WO/2011/006145, the contents of which are incorporated herein. In some embodiments a gene trap vector comprises a nucleic acid construct comprising a promoterless reporter gene flanked by an upstream splice acceptor (SA) site and a downstream polyadenylation sequence. In other words, the promoterless reporter gene is positioned downstream from a splice acceptor site and upstream from a polyA sequence (also referred to as a "polyA site" or "polyA signal"). When inserted into an intron of an expressed gene, the gene trap construct is transcribed from the endogenous promoter of that gene in the form of a fusion transcript in which the exon(s) upstream of the insertion site is spliced in frame to the reporter gene. Such a gene trap vector may be referred to as a "promoter trap" gene trap vector. Transcription terminates prematurely at the inserted polyA site, so that the resulting fusion transcript encodes a truncated and non-functional version of the cellular protein fused to the reporter. The reporter allows identification of cells in which the gene trap vector has inserted into an actively transcribed locus. Such gene trap vectors both inactivate and report the expression of the trapped gene at the insertion site and provide a nucleic acid tag that permits rapid identification of the disrupted gene. In some embodiments a gene trap vector does not encode a reporter but instead encodes a different protein. In some embodiments a gene trap vector does not encode a protein but simply causes premature termination at a polyA site inserted into an endogenous gene.

A variety of splice acceptor sites can be used in a gene trap vector in various embodiments. In some embodiments a SA site is an adenoviral SA site. In some embodiments a SA from the long fiber gene of adenovirus type 40 is used (Carette et al. 2005 The Journal of Gene Medicine 7(8) 1053-1062). Other strong adenoviral SA sites are those derived from the fiber or hexon gene of different adenoviral serotypes. A variety of polyA sequences can be used in the gene trap vector. In some embodiments a polyA sequence is a bovine growth hormone polyA sequence.

In some embodiments a gene trap vector is a polyA trap vector. A polyA trap vector comprises a nucleic acid construct comprising (i) a reporter gene comprising a nucleic acid sequence that encodes a reporter, operably linked to a promoter; and (ii) a splice donor (SD) site located downstream of the reporter gene. The gene trap vector lacks a polyA sequence, so that efficient synthesis of the reporter can only occur if the vector inserts in an intron and a polyA site is provided by splicing to downstream exons. When inserted into an intron of an endogenous gene, the transcript expressed from the gene trap promoter is spliced to the downstream exons of the endogenous gene, the most 3' of which comprises a polyA sequence, resulting in a fusion transcript that terminates with the polyA sequence of the endogenous gene. Since the fusion transcript is expressed from the inserted promoter, polyA trap vectors trap genes independently of whether the endogenous gene is expressed. The reporter allows identification of cells in which the gene trap vector has inserted into an intron, and the inserted DNA can be used to identify genomic sequences close to the insertion site. In some embodiments of the invention the SD site in an adenoviral SD site. In some embodiments, a polyA trap vector further comprises an IRES sequence downstream of the termination codon of the reporter gene and upstream of the splice donor site.

A variety of different promoters can be used, e.g., in a gene trap vector that comprises a promoter. A promoter capable of directing expression in the haploid human cells in which the gene trap vector is used can be selected by one of ordinary skill in the art. In some embodiments a promoter is an RNA polymerase II promoter (i.e., a promoter that directs transcription by RNA polymerase II). In some embodiments a promoter is a constitutive promoter. In some embodiments a promoter is a strong promoter active in a wide range of mammalian cell types, such as the CMV immediate-early promoter or major intermediate-early promoter, other mammalian viral promoters such as the herpes simplex virus (HSV) promoter, SV40 or other polyoma virus promoters, or adenovirus promoters. In some embodiments a promoter is a mammalian promoter, such as the elongation factor-1alpha (EF1alpha), phosphoglycerate kinase-1 (PGK), histone, or hTERT promoter. In some embodiments a promoter is regulatable, e.g., inducible or repressible. Examples of regulatable promoters include heat shock promoters, metallothionein promoter, and promoters that comprise an element responsive to a small molecule such as tetracycline or a related compound (e.g., doxycycline), or a hormone. For example, in some embodiments an inducible promoter comprises a hormone response element that renders the promoter responsive to a ligand for a hormone receptor. Hormone receptors include, e.g., the estrogen, progesterone, and glucocorticoid receptors. Ligands include physiological ligands, e.g., estrogen, progesterone, or cortisol, and non-physiological ligands, e.g., tamoxifen, dexamethasone. It will be understood that in various embodiments the cell expresses or is modified to express or contain appropriate trans-acting proteins typically comprising a DNA binding domain, activation or repression domain, and ligand-binding domain, that render the promoter responsive to a ligand.

In some embodiments a gene trap vector comprises first and second nucleic acid constructs that contain first and second reporter genes, respectively. The reporter genes are typically different. The first nucleic acid construct comprises a reporter gene operably linked to a promoter active in a near-haploid mammalian cell of interest. The other nucleic acid construct comprises a promoterless gene trap construct or a polyA trap construct such as those described above. A reporter encoded by the first reporter gene is used to identify cells in which the gene trap vector has integrated into the genome. A reporter encoded by the second reporter gene is used to identify cells in which such integration occurs in an endogenous gene. In some embodiments a first reporter gene encodes a selectable marker and a second reporter gene encodes a detectable marker.

In some embodiments a gene trap vector comprising a transposon is used to perform insertional mutagenesis in the human haploid cells. In some embodiments a transposon is a piggyBac transposon. A piggyBac transposon system is described in Wang, W., et al., Genome Res. 2009 19: 667-673. It contains splice acceptor (SA) Beta-geo or SA-T2A-Beta-gal-T2A-Neo gene-trap cassette flanked by the 59 and 39 PB terminal DNA repeats (59 PBTR and 39 PBTR).

In some embodiments insertion of a gene-trap vector is reversible, i.e., the inserted nucleic acid construct can be readily excised and the insertion site repaired. For example, in some embodiments recognition sites for a site-specific recombinase such as LoxP or FRT are inserted at the both ends of the gene-trap cassette, so that the integrated vectors can excised with the corresponding recombinase (e.g., Cre or Flp). In embodiments in which a transposon is used, the corresponding transposase may be used to reverse the insertion. In some embodiments a precise excision of the inserted gene trap construct occurs while in some embodiments a small amount of heterologous DNA remains after excision (e.g., a LoxP site). In some embodiments, reversal of the phenotype of a mutant cell upon excision of the gene trap construct confirms that the insertion was responsible for the phenotype.

Gene trap constructs may be made using standard methods of recombinant DNA technology and genetic engineering and can be introduced into cells using various types of vectors. In certain embodiments a gene trap vector is a viral vector, e.g., a retroviral (e.g., lentiviral), adenoviral, or herpes viral vector that comprises the gene trap construct, e.g., as part of its genome. The viral vector can be a virus (viral particle), which is used to infect cells, thereby introducing the gene trap construct. Following infection, at least a portion of the viral genome or a copy thereof integrates into the cellular genome, typically at random sites within the cell's DNA. In certain embodiments a retroviral vector is employed to deliver the gene trap construct to a near-haploid mammalian cell. Retroviral vectors and methods of using retroviruses to introduce exogenous DNA into mammalian cells are well known in the art. A retroviral vector typically comprises LTRs, which can be derived from various types of retroviruses. LTR(s) may be genetically modified to provide desired properties, and the viral genome can be modified, e.g., to lack promoter activities and/or to comprise regulatory elements suitable for propagation and selection in bacteria, such as an origin of replication and an antibiotic resistance marker. The gene trap construct is positioned between the LTRs. Infectious, replication-competent retroviral gene-trap particles can be produced by transfecting a retroviral plasmid comprising the gene trap construct into a retrovirus packaging cell line using standard methods. The packaging cells are cultured, and viral particles released into the media are collected (e.g., as supernatants) for subsequent use, e.g., to infect mammalian hear-haploid cells. In some embodiments a gene trap vector is a plasmid. In some embodiments, a plasmid gene trap vector is linearized prior to introducing it into cells.

In some embodiments, the human haploid cells described herein are contacted with a gene trap vector under conditions suitable for uptake of the vector and insertion of the construct into the genome. A wide variety of methods can be used to introduce a gene trap vector into the human haploid cells. Examples include viral infection (e.g., retroviral infection), transfection (e.g., using calcium-phosphate or lipid-based transfection reagents), electroporation, microinjection, etc. One of skill in the art can select an appropriate method based, e.g., on the nature of the vector and cell. It will be appreciated that, typically, not all cells contacted with a gene trap vector will take up the vector, and stable insertion of the construct into the genome may not occur in all cells that take up the vector. In some embodiments insertional mutagenesis is performed such that the average number of insertions per cell is between 0.1 and 2, e.g., between 0.5 and 1. The average number of insertions can be controlled, for example, by using an appropriate ratio of cells to vectors.

In some embodiments, the haploid human cells that have been contacted with a gene trap vector under conditions suitable for uptake and insertion of the construct are maintained in culture for a period of time prior to identifying, isolating, or assessing cells that have incorporated the construct into their genome. For example, cells may be cultured for between 1 and about 20 days prior to identification, isolation, or characterization. In some embodiments, cells that have taken up the construct and, in some embodiments, have the construct inserted into their genome, are identified or isolated. In some embodiments, cells are identified or isolated based at least in part on a reporter, e.g., a reporter encoded by the gene trap vector and inserted into the genome. For example, cells can be subjected to sorting or cultured under selective conditions so as to eliminate at least, e.g., 95%, 98%, 99%, 99.9%, or more of the cells that do not express a reporter. In some embodiments a reporter-based selection step is not performed. In some embodiments, e.g., in the case of a promoterless gene trap vector, omitting a reporter-based selection may broaden the mutagenized cell population to include types of gene-trap insertions that may otherwise be less amenable to identification, e.g., poorly expressed genes.

In some embodiments, the cells are cultured as single cells so as to generate a clonal population (or homogeneous population) of mutated haploid human stem cells. In this embodiment, each clonal population is cultured in a separate container (e.g. culture dish).

In other embodiments, a heterogeneous population of haploid human stem cells is cultured in a single dish. Thus cells with different inactivated genes are cultured in the same dish The assay of the present invention is carried out by exposing (e.g. contacting) the population of cells with a cytotoxic therapy.

The term "cytotoxic therapy" as used in refers to a therapy that inhibits or prevents the function of cells and/or causes destruction of cells (cell death), and/or exerts anti-neoplastic/anti-proliferative effects, for example, prevents directly or indirectly the development, maturation or spread of neoplastic tumor cells. In one embodiment, the cytotoxic therapy causes a cytostatic effect.

In one embodiment, the cytotoxic therapy refers to a radiation therapy-nonlimiting examples of which include X-rays, gamma rays, charged particle therapy, brachytherapy, alpha particles and radioisotopes.

In another embodiment, the cytotoxic therapy refers to a substance—for example a chemical or biological agent.

Exemplary substances include small molecule agents, antibodies, peptides, nucleic acid agents and other chemicals.

In one embodiment, the candidate agent is a chemotherapeutic agent.

Exemplary chemotherapeutic agents are provided in Table 1A herein below.

TABLE 1A

Examples of chemotherapeutic agents

| Class | Type of Agent | Name | Disease |
|---|---|---|---|
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan | Multiple myeloma, breast, ovary |
| | | Chlorambucil | Chronic lymphocytic leukemia, primary macroglobulinemia, Hodgkin's disease, non-Hodgkin's lymphomas |
| | | Estramustine | Prostate |
| | Ethylenimines and Methylmelamines | Hexamethyl-melamine | Ovary |
| | | Thiotepa | Bladder, breast, ovary |
| | Alkyl Sulfonates | Busulfan | Chronic granulocytic leukemia |
| | Nitrosoureas | Carmustine | Hodgkin's disease, non-Hodgkin's lymphomas, primary brain tumors, multiple myeloma, malignant melanoma |
| | | Lomustine | Hodgkin's disease, non-Hodgkin's lymphomas, primary brain tumors, small-cell lung |
| | | Semustine | Primary brain tumors, stomach, colon |
| | | Streptozocin | Malignant pancreatic insulinoma, malignant carcinoid |
| | Triazenes | Dacarbazine | Malignant melanoma, Hodgkin's |
| | | Procarbazine | disease, soft-tissue sarcomas |
| | | Aziridine | |

TABLE 1A-continued

Examples of chemotherapeutic agents

| Class | Type of Agent | Name | Disease |
|---|---|---|---|
| Antimetabolites | Folic Acid Analogs | Methotrexate Trimetrexate | Acute lymphocytic leukemia, choriocarcinoma, mycosis fungoides, breast, head and neck, lung, osteogenic sarcoma |
| | Pyrimidine Analogs | Fluorouracil Floxuridine | Breast, colon, stomach, pancreas, ovary, head and neck, urinary bladder, premalignant skin lesions (topical) |
| | | Cytarabine | Acute granulocytic and acute |
| | Purine Analogs and Related Inhibitors | Azacitidine Mercaptopurine | lymphocytic leukemias Acute lymphocytic, acute granulocytic, and chronic granulocytic leukemias |
| | | Thioguanine | Acute granulocytic, acute lymphocytic, and chronic granulocytic leukemias |
| | | Pentostatin | Hairy cell leukemia, mycosis fungoides, chronic lymphocytic leukemia |
| | | Fludarabine | Chronic lymphocytic leukemia, Hodgkin's and non-Hodgkin's lymphomas, mycosis fungoides |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | | Vindesine | Vinca-resistant acute lymphocytic leukemia, chronic myelocytic leukemia, melanoma, lymphomas, breast |
| | Epipodophyl-Lotoxins | Etoposide Teniposide | Testis, small-cell lung and other lung, breast, Hodgkin's disease, non-Hodgkin's lymphomas, acute granulocytic leukemia, Kaposi's sarcoma |
| | Antibiotics | Dactinomycin | Choriocarcinoma, Wilms' tumor, rhabdomyosarcoma, testis, Kaposi's sarcoma |
| | | Daunorubicin | Acute granulocytic and acute lymphocytic leukemias |
| | | Doxorubicin 4'-Deoxydoxorubicin | Soft-tissue, osteogenic, and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung, and genitourinary tract; |

TABLE 1A-continued

Examples of chemotherapeutic agents

| Class | Type of Agent | Name | Disease |
|---|---|---|---|
| | | Plicamycin | Hodgkin's disease, non-Hodgkin's lymphomas Testis, malignant hypercalcemia |
| | | Mitomycin | Stomach, cervix, colon, breast, pancreas, bladder, head and neck |
| | Enzymes | L-Asparaginase | Acute lymphocytic leukemia |
| | Taxanes | Docetaxel Paclitaxel | Breast, ovarian |
| | Biological Response Modifiers | Interferon Alfa | Hairy cell leukemia, Kaposi's sarcoma, melanoma, carcinoid, renal cell, ovary, bladder, non-Hodgkin's lymphomas, mycosis fungoides, multiple myeloma, chronic granulocytic leukemia |
| | | Tumor Necrosis Factor | Investigational |
| | | Tumor-Infiltrating Lymphocytes | Investigational |
| Miscellaneous Agents | Platinum Coordination Complexes | Cisplatin Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essential thrombocytosis, malignant melanoma |
| | Methyl Hydrazine Derivative | Procarbazine | Hodgkin's disease |
| | Adrenocortical Suppressant | Mitotane Aminoglutethimide | Adrenal cortex Breast |
| Hormones and Antagonists | costeroids | | Acute and chronic lymphocytic leukemias, non-Hodgkin's lymphomas, Hodgkin's disease, breast |
| | Progestins | Hydroxy-progesterone caproate Medroxy-progesterone acetate Megestrol acetate | Endometrium, breast |
| | Estrogens | Diethylstil-bestrol Ethinyl estradiol | Breast, prostate |
| | Antiestrogen | Tamoxifen | Breast |
| | Androgens | Testosterone propionate Fluoxymesterone | Breast |

TABLE 1A-continued

Examples of chemotherapeutic agents

| Class | Type of Agent | Name | Disease |
|---|---|---|---|
| | Antiandrogen | Flutamide | Prostate |
| | Gonadotropin-Releasing hormone analog | Leuprolide Goserelin | Prostate, Estrogen-receptor-positive breast |

Additional anti-cancer drugs that may be screened include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

Exposing the cells with the candidate therapy can be performed under any in vitro conditions. When the candidate therapy is an agent, the candidate agent may be in direct contact with the cells. According to some embodiments of the invention, the cells are incubated with the candidate agent. The conditions used for incubating the cells are selected for a time period/concentration of cells/concentration of candidate agent/ratio between cells and candidate agent and the like which enable the candidate agent to induce cellular changes, such as changes in transcription and/or translation rate of specific genes, proliferation rate, differentiation, cell death, necrosis, apoptosis and the like.

Following exposure of the candidate therapy with the cells, the method continues by selecting cells using a selection approach based on cell survival may be used. Cells that survive in the presence of the candidate therapy may be isolated, and one or more genes mutated in one or more of the cells are identified (e.g. using known sequencing methods). In some embodiments cells that have been contacted with a gene trap vector are maintained in culture prior to exposure with the candidate therapy for a period of to allow time for changes in gene expression and gene product level resulting from a mutation to occur and potentially give rise to a resistant phenotype.

In some embodiments cells that show a resistance to an activity of the candidate agent are expanded in culture after being isolated or identified, e.g., after having survived a survival-based selection. In some embodiments cells are expanded for between 2 and 30 days.

A variety of methods can be used to identify the genes that have been inactivated or overactivated (e.g. genes that have a gene trap vector or portion thereof inserted therein). In some embodiments inverse PCR is used to identify genomic sequences flanking the insertion. In some embodiments splinkerette PCR is used (Horn, C., et al., Nat. Genet., 39: 807-8, 2007). In some embodiments 5'-RACE (rapid amplification of cDNA ends) is used to amplify cellular sequences contained in a gene-trap fusion transcript (see, e.g., Nature Methods, 2(8), 2005). See also Stanford, W., et al. Methods in Enzymology, Vol. 420, 2006). Examples of identifying genes mutagenized using a gene trap vector are described in WO/2011/006145. In some embodiments, sequences flanking the insertion are recovered and sequenced from large populations of cells simultaneously using "high throughput", "next-generation", or "massively parallel" sequencing. Such sequencing techniques can comprise sequencing by synthesis (e.g., using Solexa technology), sequencing by ligation (e.g., using SOLiD technology from Applied Biosystems), 454 technology, or pyrosequencing. In some embodiments thousands, tens of thousands or more sequencing reactions are performed in parallel, generating millions or even billions of bases of DNA sequence per "run". See, e.g., Shendure J & Ji H. Nat. Biotechnol., 26(10):1135-45, 2008, Mardis E R (2008) Next-generation DNA sequencing methods. Annu Rev Genomics Hum Genet. 9:387-402; and/or Metzger, M., Nat Rev Genet. 2010; 11(1):31-46, for non-limiting discussion of some of these technologies. It will be appreciated that sequencing technologies are evolving and improving rapidly. In some embodiments massively parallel sequencing by synthesis is used. In some embodiments Linear Amplification Mediated-PCR (LAM-PCR), followed by ssDNA linker ligation and massively parallel sequencing is used. The populations of cells that are resistant to the activity of the candidate agent are selected, and genomic regions that are enriched for insertions are identified. Such regions contain candidate genetic elements, e.g., genes, involved in the phenotype of interest. In some embodiments 10,000 or more, e.g., between 10,000 and 100,000; 10,000 and 500,000; or between 10,000 and 1 million, 5 million, 10 million, 20 million, 50 million, 100 million, insertions, or more, are analyzed. Once the DNA is isolated and, in some embodiments amplified, it can be cloned into a vector and/or sequenced. The DNA can be used as a probe to identify further sequences located nearby in the genome, e.g., by probing a cDNA or genomic library. The sequence can be used to search sequence databases, e.g., publicly available databases such as those available through Entrez at the National Center for Biotechnology Information website (www.ncbi.nlm.nih.gov/), e.g., GenBank, RefSeq, Protein, and Nucleotide. Since the human genome is completely sequenced it will generally be possible to readily identify most genes based on a relatively small amount of partial sequence data. Sequences may be aligned with the human genome using appropriate software. The University of California, Santa Cruz (UCSC) Genome Browser website (genome.ucsc.edul) provides a large database of publicly available sequence and annotation data along with an integrated tool set useful for, e.g., examining the genomes of organisms, aligning sequence to genomes, and performing various other analyses (Rhead B, et al. The UCSC Genome Browser database: update 2010. Nucleic Acids Research. 2010; 38:D613-D619). In some embodiments Bowtie alignment software is used (Langmead B, et al. Genome Biology. 2009; 10). Insertion sites can be identified as located in genomic regions annotated to contain genes.

In some embodiments the method of analysis focuses on insertions obtained in a given screen that are present in genes and compares them to insertions present in an unselected mutagenized population of haploid human ES cells (e.g., a population mutagenized at the same time as the cells subjected to screening). Enrichment of a particular gene in a particular screen can be calculated by comparing how often that gene is mutated in the screen compared to how often the gene carries an insertion in a control dataset obtained by analyzing insertion sites in an unselected population. A p-value (optionally corrected for false discovery rate) can be calculated using a suitable statistical test, such as the one-sided Fisher exact test. In some embodiments, analysis comprises obtaining a proximity index for a given insertion as the inverse value of the average distances with its neighboring insertion sites. The inverse value is calculated from the average distance (in base pairs) between the given insertion and the two neighboring upstream insertions and the two next downstream insertion sites. This method of analysis identifies insertion-rich regions and includes sense and antisense insertions and facilitates identification of non-annotated elements.

Once the gene/genes has/have been identified that brings about resistance to the candidate agent, the present inventors contemplate analyzing the gene sequence and or expression therefrom in a cell sample of the subject.

The analyzing may be effected once or on multiple occasions (i.e. periodically during the course of the cancer treatment). In one embodiment, the analyzing is effected prior to the start of a new cycle of chemotherapy.

The cell sample may be derived from any tissue or body fluid of the subject. Exemplary body fluids contemplated by the present invention include, but are not limited to blood, serum, plasma, urine, saliva, sweat etc. In one embodiment, the cell sample is derived from the primary tumor sample. Additionally, or alternatively, the cell sample may be derived from a metastasized tumor.

In one embodiment, a cell sample (e.g. biopsy) is taken from a single source in the patient. In another embodiment, the cell sample (e.g. biopsy) is taken from multiple regions of the patient.

According to a particular embodiment, the cell sample may be analyzed for a nucleic acid variation in the identified gene. According to this embodiment, when the sequence of the identified gene is different to the sequence of that gene in a healthy subject (or to the sequence of that gene in a subject known not to be resistant to the effects of the agent) this is indicative that the candidate therapy should not be used (at least as a single therapy) for treating the disease (e.g. it may be ruled out entirely for treating that disease or it may be ruled in for use as combination therapy only, or it may be ruled in for use together with a sensitizing agent).

Non-limiting examples of such nucleic acid variations include a missense mutation, i.e., a mutation which changes an amino acid residue in the protein encoded by the identified gene with another amino acid residue and thereby abolishes the enzymatic activity of the protein; a nonsense mutation, i.e., a mutation which introduces a stop codon in a protein encoded by the identified gene, e.g., an early stop codon which results in a shorter protein devoid of the enzymatic activity; a frameshift mutation, i.e., a mutation, usually, deletion or insertion of nucleic acid(s) which changes the reading frame of the protein encoded by the identified gene, and may result in an early termination by introducing a stop codon into a reading frame (e.g., a truncated protein, devoid of the enzymatic activity), or in a longer amino acid sequence (e.g., a readthrough protein) which affects the secondary or tertiary structure of the protein and results in a non-functional protein, devoid of the enzymatic activity of the "wild-type" or non-mutated polypeptide; a readthrough mutation due to a frameshift mutation or a modified stop codon mutation (i.e., when the stop codon is mutated into an amino acid codon), with an abolished enzymatic activity; a promoter mutation, i.e., a mutation in a promoter sequence, usually 5' to the transcription start site of a gene, which results in down-regulation of a specific gene product; a regulatory mutation, i.e., a mutation in a region upstream or downstream, or within a gene, which affects the expression of the gene product; a deletion mutation, i.e., a mutation which deletes coding nucleic acids in a gene sequence and which may result in a frameshift mutation or an in-frame mutation (within the coding sequence, deletion of one or more amino acid codons); an insertion mutation, i.e., a mutation which inserts coding or non-coding nucleic acids into a gene sequence, and which may result in a frameshift mutation or an in-frame insertion of one or more amino acid codons; an inversion, i.e., a mutation which results in an inverted coding or non-coding sequence; a splice mutation (i.e., a mutation which results in abnormal splicing or poor splicing; and a duplication mutation, i.e., a mutation which results in a duplicated coding or non-coding sequence, which can be in-frame or can cause a frameshift.

To determine sequence alterations [e.g., a single nucleotide polymorphism (SNP)] in the identified gene, DNA is first obtained from the cell sample of the tested subject.

Once the sample is obtained, DNA is extracted using methods which are well known in the art, involving tissue mincing, cell lysis, protein extraction and DNA precipitation using 2 to 3 volumes of 100% ethanol, rinsing in 70% ethanol, pelleting, drying and resuspension in water or any other suitable buffer (e.g., Tris-EDTA). Preferably, following such procedure, DNA concentration is determined such as by measuring the optical density (OD) of the sample at 260 nm (wherein 1 unit OD=50 µg/ml DNA).

To determine the presence of proteins in the DNA solution, the OD 260/OD 280 ratio is determined. Preferably, only DNA preparations having an OD 260/OD 280 ratio between 1.8 and 2 are used in the following procedures described hereinbelow.

The sequence alteration (or SNP) of some embodiments of the invention can be identified using a variety of methods. One option is to determine the entire gene sequence of a PCR reaction product (see sequence analysis, hereinbelow). Alternatively, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

Restriction Fragment Length Polymorphism (RFLP):

This method uses a change in a single nucleotide (the SNP nucleotide) which modifies a recognition site for a restriction enzyme resulting in the creation or destruction of an RFLP. Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807-6817, 1990). However, this method requires the use of osmium tetroxide and piperidine, two highly noxious chemicals which are not suited for use in a clinical laboratory.

The DNA sample is preferably amplified prior to determining sequence alterations, since many genotyping methods require amplification of the DNA region carrying the sequence alteration of interest.

In any case, once DNA is obtained, determining the presence of a sequence alteration in the identified gene is effected using methods which typically involve the use of oligonucleotides which specifically hybridize with the nucleic acid sequence alterations in the identified gene, such as those described hereinabove.

The term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly to respective naturally-occurring portions.

Oligonucleotides designed according to the teachings of some embodiments of the invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

The oligonucleotide of some embodiments of the invention is of at least 17, at least 18, at least 19, at least 20, at least 22, at least 25, at least 30 or at least 40, bases specifically hybridizable with sequence alterations described hereinabove.

Additional methods of detecting sequence alterations involve directly determining the identity of the nucleotide at the alteration site by a sequencing assay, an enzyme-based mismatch detection assay, or a hybridization assay. The following is a description of some preferred methods which can be utilized by some embodiments of the invention.

Sequencing Analysis—

The isolated DNA is subjected to automated dideoxy terminator sequencing reactions using a dye-terminator (unlabeled primer and labeled di-deoxy nucleotides) or a dye-primer (labeled primers and unlabeled di-deoxy nucleotides) cycle sequencing protocols. For the dye-terminator reaction, a PCR reaction is performed using unlabeled PCR primers followed by a sequencing reaction in the presence of one of the primers, deoxynucleotides and labeled di-deoxy nucleotide mix. For the dye-primer reaction, a PCR reaction is performed using PCR primers conjugated to a universal or reverse primers (one at each direction) followed by a sequencing reaction in the presence of four separate mixes (correspond to the A, G, C, T nucleotides) each containing a labeled primer specific the universal or reverse sequence and the corresponding unlabeled di-deoxy nucleotides.

Microsequencing Analysis—

This analysis can be effected by conducting microsequencing reactions on specific regions of the identified gene which may be obtained by amplification reaction (PCR) such as mentioned hereinabove. Genomic or cDNA amplification products are then subjected to automated microsequencing reactions using ddNTPs (specific fluorescence for each ddNTP) and an appropriate oligonucleotide microsequencing primer which can hybridize just upstream of the alteration site of interest. Once specifically extended at the 3' end by a DNA polymerase using a complementary fluorescent dideoxynucleotide analog (thermal cycling), the primer is precipitated to remove the unincorporated fluorescent ddNTPs. The reaction products in which fluorescent ddNTPs have been incorporated are then analyzed by electrophoresis on sequencing machines (e.g., ABI 377) to determine the identity of the incorporated base, thereby identifying the sequence alteration in the identified gene of some embodiments of the invention.

It will be appreciated that the extended primer may also be analyzed by MALDI-TOF Mass Spectrometry. In this case, the base at the alteration site is identified by the mass added onto the microsequencing primer [see Haff and Smirnov, (1997) Nucleic Acids Res. 25(18):3749-50].

Solid phase microsequencing reactions which have been recently developed can be utilized as an alternative to the microsequencing approach described above. Solid phase microsequencing reactions employ oligonucleotide microsequencing primers or PCR-amplified products of the DNA fragment of interest which are immobilized. Immobilization can be carried out, for example, via an interaction between biotinylated DNA and streptavidin-coated microtitration wells or avidin-coated polystyrene particles.

In such solid phase microsequencing reactions, incorporated ddNTPs can either be radiolabeled [see Syvanen, (1994),] Clin Chim Acta 1994; 226(2):225-236] or linked to fluorescein (see Livak and Hainer, (1994) Hum Mutat 1994; 3(4):379-385]. The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such asp-nitrophenyl phosphate).

Other reporter-detection conjugates include: ddNTP linked to dinitrophenyl (DNP) and anti-DNP alkaline phosphatase conjugate [see Harju et al., (1993) Clin Chem 39:2282-2287]; and biotinylated ddNTP and horseradish peroxidase-conjugated streptavidin with o-phenylenediamine as a substrate (see WO 92/15712).

A diagnostic kit based on fluorescein-linked ddNTP with antifluorescein antibody conjugated with alkaline phosphatase is commercially available from GamidaGen Ltd (PRONTO).

Other modifications of the microsequencing protocol are described by Nyren et al. (1993) Anal Biochem 208(1):171-175 and Pastinen et al. (1997) Genome Research 7:606-614.

Mismatch Detection Assays Based on Polymerases and Ligases—

The "Oligonucleotide Ligation Assay" (OLA) uses two oligonucleotides which are designed to be capable of hybridizing to abutting sequences of a single strand of a target molecule. One of the oligonucleotides is biotinylated, and the other is detectably labeled. If the precise complementary sequence is found in a target molecule, the oligonucleotides will hybridize such that their termini abut, and create a ligation substrate that can be captured and detected. OLA is capable of detecting single nucleotide polymorphisms and may be advantageously combined with PCR as described by Nickerson et al. (1990) Proc. Natl. Acad. Sci. U.S.A. 87:8923-8927. In this method, PCR is used to achieve the exponential amplification of target DNA, which is then detected using OLA.

Other amplification methods which are particularly suited for the detection of single nucleotide polymorphism include LCR (ligase chain reaction), Gap LCR (GLCR). LCR uses two pairs of probes to exponentially amplify a specific target. The sequences of each pair of oligonucleotides, is selected to permit the pair to hybridize to abutting sequences of the same strand of the target. Such hybridization forms a substrate for a template-dependant ligase. In accordance with some embodiments of the invention, LCR can be performed with oligonucleotides having the proximal and distal sequences of the same strand of a biallelic marker site. In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide. In an alternative embodiment, the oligonucleotides will not include the biallelic marker, such that when they hybridize to the target molecule, a "gap" is created as described in WO 90/01069. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained.

Ligase/Polymerase-mediated Genetic Bit Analysis™ is another method for determining the identity of a nucleotide at a preselected site in a nucleic acid molecule (WO 95/21271). This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

Hybridization Assay Methods—

Hybridization based assays which allow the detection of single base alterations rely on the use of oligonucleotide which can be 10, 15, 20, or 30 to 100 nucleotides long preferably from 10 to 50, more preferably from 40 to 50 nucleotides. Typically, the oligonucleotide includes a central nucleotide complementary to a polymorphic site of the identified gene and flanking nucleotide sequences spanning on each side of the central nucleotide and substantially complementary to the nucleotide sequences of the identified gene spanning on each side of the polymorphic site. Sequence alteration can be detected by hybridization of the oligonucleotide of some embodiments of the invention to the template sequence under stringent hybridization reactions.

By way of example, hybridization of short nucleic acids (below 200 bp in length, e.g. 17-40 bp in length) can be effected by the following hybridization protocols depending on the desired stringency; (i) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1-1.5° C. below the Tm, final wash solution of 3 M TMACl, 0.01 M sodium phosphate (pH 6.8), 1 mM EDTA (pH 7.6), 0.5% SDS at 1-1.5° C. below the Tm; (ii) hybridization solution of 6×SSC and 0.1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2-2.5° C. below the Tm, final wash solution of 3 M TMACl, 0.01 M sodium phosphate (pH 6.8), 1 mM EDTA (pH 7.6), 0.5% SDS at 1-1.5° C. below the Tm, final wash solution of 6×SSC, and final wash at 22° C.; (iii) hybridization solution of 6×SSC and 1% SDS or 3 M TMACl, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature.

The detection of hybrid duplexes can be carried out by a number of methods. Typically, hybridization duplexes are separated from unhybridized nucleic acids and the labels bound to the duplexes are then detected. Such labels refer to radioactive, fluorescent, biological or enzymatic tags or labels of standard use in the art. A label can be conjugated to either the oligonucleotide probes or the nucleic acids derived from the biological sample (target). For example, oligonucleotides of some embodiments of the invention can be labeled subsequent to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, lissamine, phycoerythrin, rhodamine (Perkin Elmer Cetus), Cy2, Cy3, Cy3.5, Cy5, Cy5.5, Cy7, FluorX (Amersham) and others [e.g., Kricka et al. (1992), Academic Press San Diego, Calif] can be attached to the oligonucleotides.

Traditional hybridization assays include PCR, RT-PCR, RNase protection, in-situ hybridization, primer extension, Southern blot, Northern Blot and dot blot analysis.

Those skilled in the art will appreciate that wash steps may be employed to wash away excess target DNA or probe as well as unbound conjugate. Further, standard heterogeneous assay formats are suitable for detecting the hybrids using the labels present on the oligonucleotide primers and probes.

Two recently developed assays allow hybridization-based allele discrimination with no need for separations or washes [see Landegren U. et al., (1998) Genome Research, 8:769-776]. The TaqMan assay takes advantage of the 5' nuclease activity of Taq DNA polymerase to digest a DNA probe annealed specifically to the accumulating amplification product. TaqMan probes are labeled with a donor-acceptor dye pair that interacts via fluorescence energy transfer. Cl cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time [see Livak et al., 1995 Hum Mutat 3(4):379-385]. In an alternative homogeneous hybridization based procedure, molecular beacons are used for allele discriminations. Molecular beacons are hairpin-shaped oligonucleotide probes that report the presence of specific nucleic acids in homogeneous solutions. When they bind to their targets they undergo a conformational reorganization that restores the fluorescence of an internally quenched fluorophore (Tyagi et al., (1998) Nature Biotechnology. 16:49].

It will be appreciated that a variety of controls may be usefully employed to improve accuracy of hybridization assays. For instance, samples may be hybridized to an irrelevant probe and treated with RNAse A prior to hybridization, to assess false hybridization.

U.S. Pat. No. 5,451,503 provides several examples of oligonucleotide configurations which can be utilized to detect SNPs in template DNA or RNA.

Hybridization to Oligonucleotide Arrays—

The chip/array technology has already been applied with success in numerous cases. For example, the screening of mutations has been undertaken in the BRCA1 gene, in S. cerevisiae mutant strains, and in the protease gene of HIV-1 virus [see Hacia et al., (1996) Nat Genet 1996; 14(4):441-447; Shoemaker et al., (1996) Nat Genet 1996; 14(4):450-456; Kozal et al., (1996) Nat Med 1996; 2(7):753-759].

The nucleic acid sample which includes the candidate region to be analyzed is isolated, amplified and labeled with a reporter group. This reporter group can be a fluorescent group such as phycoerythrin. The labeled nucleic acid is then incubated with the probes immobilized on the chip using a fluidics station. For example, Manz et al. (1993) Adv in Chromatogr 1993; 33:1-66 describe the fabrication of fluidics devices and particularly microcapillary devices, in silicon and glass substrates.

Once the reaction is completed, the chip is inserted into a scanner and patterns of hybridization are detected. The hybridization data is collected, as a signal emitted from the reporter groups already incorporated into the nucleic acid, which is now bound to the probes attached to the chip. Probes that perfectly match a sequence of the nucleic acid sample generally produce stronger signals than those that have mismatches. Since the sequence and position of each probe immobilized on the chip is known, the identity of the nucleic acid hybridized to a given probe can be determined.

For single-nucleotide polymorphism analyses, sets of four oligonucleotide probes (one for each base type), preferably sets of two oligonucleotide probes (one for each base type of the biallelic marker) are generally designed that span each position of a portion of the candidate region found in the nucleic acid sample, differing only in the identity of the polymorphic base. The relative intensity of hybridization to each series of probes at a particular location allows the identification of the base corresponding to the polymorphic base of the probe.

It will be appreciated that the use of direct electric field control improves the determination of single base mutations (Nanogen). A positive field increases the transport rate of negatively charged nucleic acids and results in a 10-fold increase of the hybridization rates. Using this technique, single base pair mismatches are detected in less than 15 sec [see Sosnowski et al., (1997) Proc Natl Acad Sci USA 1997; 94(4):1119-1123].

Integrated Systems—Another technique which may be used to analyze sequence alterations includes multicomponent integrated systems, which miniaturize and compartmentalize processes such as PCR and capillary electrophoresis reactions in a single functional device. An example of such technique is disclosed in U.S. Pat. No. 5,589,136, which describes the integration of PCR amplification and capillary electrophoresis in chips.

Integrated systems are preferably employed along with microfluidic systems. These systems comprise a pattern of microchannels designed onto a glass, silicon, quartz, or plastic wafer included on a microchip. The movements of the samples are controlled by electric, electro-osmotic or hydrostatic forces applied across different areas of the microchip to create functional microscopic valves and pumps with no moving parts. Varying the voltage controls the liquid flow at intersections between the micro-machined channels and changes the liquid flow rate for pumping across different sections of the microchip.

When identifying sequence alterations, a microfluidic system may integrate nucleic acid amplification, microsequencing, capillary electrophoresis and a detection method such as laser-induced fluorescence detection. In a first step, the DNA sample is amplified, preferably by PCR. The amplification product is then subjected to automated microsequencing reactions using ddNTPs (specific fluorescence for each ddNTP) and the appropriate oligonucleotide microsequencing primers which hybridize just upstream of the targeted polymorphic base. Once the extension at the 3' end is completed, the primers are separated from the unincorporated fluorescent ddNTPs by capillary electrophoresis. The separation medium used in capillary electrophoresis can for example be polyacrylamide, polyethyleneglycol or dextran. The incorporated ddNTPs in the single-nucleotide primer extension products are identified by fluorescence detection. This microchip can be used to process 96 to 384 samples in parallel. It can use the typical four-color laser induced fluorescence detection of ddNTPs.

Allele Specific Oligonucleotide (ASO):

In this method an allele-specific oligonucleotides (ASOs) is designed to hybridize in proximity to the polymorphic nucleotide, such that a primer extension or ligation event can be used as the indicator of a match or a mis-match. Hybridization with radioactively labeled allelic specific oligonucleotides (ASO) also has been applied to the detection of specific SNPs (Conner et al., Proc. Natl. Acad. Sci., 80:278-282, 1983). The method is based on the differences in the melting temperature of short DNA fragments differing by a single nucleotide. Stringent hybridization and washing conditions can differentiate between mutant and wild-type alleles.

Denaturing/Temperature Gradient Gel Electrophoresis (DGGE/TGGE):

Two other methods rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in melting properties of homoduplexes versus heteroduplexes differing in a single nucleotide can detect the presence of SNPs in the target sequences because of the corresponding changes in their electrophoretic mobilities. The fragments to be analyzed, usually PCR products, are "clamped" at one end by a long stretch of G-C base pairs (30-80) to allow complete denaturation of the sequence of interest without complete dissociation of the strands. The attachment of a GC "clamp" to the DNA fragments increases the fraction of mutations that can be recognized by DGGE (Abrams et al., Genomics 7:463-475, 1990). Attaching a GC clamp to one primer is critical to ensure that the amplified sequence has a low dissociation temperature (Sheffield et al., Proc. Natl. Acad. Sci., 86:232-236, 1989; and Lerman and Silverstein, Meth. Enzymol., 155:482-501, 1987). Modifications of the technique have been developed, using temperature gradients (Wartell et al., Nucl. Acids Res., 18:2699-2701, 1990), and the method can be also applied to RNA: RNA duplexes (Smith et al., Genomics 3:217-223, 1988).

Limitations on the utility of DGGE include the requirement that the denaturing conditions must be optimized for each type of DNA to be tested. Furthermore, the method requires specialized equipment to prepare the gels and maintain the needed high temperatures during electrophoresis. The expense associated with the synthesis of the clamping tail on one oligonucleotide for each sequence to be tested is also a major consideration. In addition, long running times are required for DGGE. The long running time of DGGE was shortened in a modification of DGGE called constant denaturant gel electrophoresis (CDGE) (Borrensen et al., Proc. Natl. Acad. Sci. USA 88:8405, 1991). CDGE requires that gels be performed under different denaturant conditions in order to reach high efficiency for the detection of SNPs.

A technique analogous to DGGE, termed temperature gradient gel electrophoresis (TGGE), uses a thermal gradient rather than a chemical denaturant gradient (Scholz, et al., Hum. Mol. Genet. 2:2155, 1993). TGGE requires the use of specialized equipment which can generate a temperature gradient perpendicularly oriented relative to the electrical field. TGGE can detect mutations in relatively small fragments of DNA therefore scanning of large gene segments requires the use of multiple PCR products prior to running the gel.

Single-Strand Conformation Polymorphism (SSCP):

Another common method, called "Single-Strand Conformation Polymorphism" (SSCP) was developed by Hayashi, Sekya and colleagues (reviewed by Hayashi, PCR Meth. Appl., 1:34-38, 1991) and is based on the observation that single strands of nucleic acid can take on characteristic conformations in non-denaturing conditions, and these conformations influence electrophoretic mobility. The complementary strands assume sufficiently different structures that one strand may be resolved from the other. Changes in sequences within the fragment will also change the conformation, consequently altering the mobility and allowing this to be used as an assay for sequence variations (Orita, et al., Genomics 5:874-879, 1989; Orita et al. 1989, Proc. Natl. Acad. Sci. U.S.A. 86:2776-2770).

The SSCP process involves denaturing a DNA segment (e.g., a PCR product) that is labeled on both strands, followed by slow electrophoretic separation on a non-denaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

Dideoxy Fingerprinting (ddF):

The dideoxy fingerprinting (ddF) is another technique developed to scan genes for the presence of mutations (Liu and Sommer, PCR Methods Appli., 4:97, 1994). The ddF technique combines components of Sanger dideoxy sequencing with SSCP. A dideoxy sequencing reaction is performed using one dideoxy terminator and then the reaction products are electrophoresed on nondenaturing polyacrylamide gels to detect alterations in mobility of the termination segments as in SSCP analysis. While ddF is an improvement over SSCP in terms of increased sensitivity, ddF requires the use of expensive dideoxynucleotides and this technique is still limited to the analysis of fragments of the size suitable for SSCP (i.e., fragments of 200-300 bases for optimal detection of mutations).

In addition to the above limitations, all of these methods are limited as to the size of the nucleic acid fragment that can be analyzed. For the direct sequencing approach, sequences of greater than 600 base pairs require cloning, with the consequent delays and expense of either deletion sub-cloning or primer walking, in order to cover the entire fragment. SSCP and DGGE have even more severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs. The ddF technique, as a combination of direct sequencing and SSCP, is also limited by the relatively small size of the DNA that can be screened.

Pyrosequencing™ Analysis (Pyrosequencing, Inc. Westborough, MA, USA):

This technique is based on the hybridization of a sequencing primer to a single stranded, PCR-amplified, DNA template in the presence of DNA polymerase, ATP sulfurylase, luciferase and apyrase enzymes and the adenosine 5' phosphosulfate (APS) and luciferin substrates. In the second step the first of four deoxynucleotide triphosphates (dNTP) is added to the reaction and the DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. In the last step the ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a Pyrogram™. Each light signal is proportional to the number of nucleotides incorporated.

Acycloprime™ Analysis (Perkin Elmer, Boston, Massachusetts, USA):

This technique is based on fluorescent polarization (FP) detection. Following PCR amplification of the sequence containing the SNP of interest, excess primer and dNTPs are removed through incubation with shrimp alkaline phosphatase (SAP) and exonuclease I. Once the enzymes are heat inactivated, the Acycloprime-FP process uses a thermostable polymerase to add one of two fluorescent terminators to a primer that ends immediately upstream of the SNP site. The terminator(s) added are identified by their increased FP and represent the allele(s) present in the original DNA sample. The Acycloprime process uses AcycloPol™, a novel mutant thermostable polymerase from the Archeon family, and a pair of AcycloTerminators™ labeled with R110 and TAMRA, representing the possible alleles for the SNP of interest. AcycloTerminator™ non-nucleotide analogs are biologically active with a variety of DNA polymerases. Similarly to 2', 3'-dideoxynucleotide-5'-triphosphates, the acyclic analogs function as chain terminators. The analog is incorporated by the DNA polymerase in a base-specific manner onto the 3'-end of the DNA chain, and since there is no 3'-hydroxyl, is unable to function in further chain elongation. It has been found that AcycloPol has a higher affinity and specificity for derivatized AcycloTerminators than various Taq mutant have for derivatized 2',3'-dideoxynucleotide terminators.

Reverse Dot Blot:

This technique uses labeled sequence specific oligonucleotide probes and unlabeled nucleic acid samples. Activated primary amine-conjugated oligonucleotides are covalently attached to carboxylated nylon membranes. After hybridization and washing, the labeled probe, or a labeled fragment of the probe, can be released using oligomer restriction, i.e., the digestion of the duplex hybrid with a restriction enzyme. Circular spots or lines are visualized colorimetrically after hybridization through the use of streptavidin horseradish peroxidase incubation followed by development using tetramethylbenzidine and hydrogen peroxide, or via chemiluminescence after incubation with avidin alkaline phosphatase conjugate and a luminous substrate susceptible to enzyme activation, such as CSPD, followed by exposure to x-ray film.

It will be appreciated that advances in the field of SNP detection have provided additional accurate, easy, and inexpensive large-scale SNP genotyping techniques, such as dynamic allele-specific hybridization (DASH, Howell, W. M. et al., 1999. Dynamic allele-specific hybridization (DASH). Nat. Biotechnol. 17: 87-8), microplate array diagonal gel electrophoresis [MADGE, Day, I. N. et al., 1995. High-throughput genotyping using horizontal polyacrylamide gels with wells arranged for microplate array diagonal gel electrophoresis (MADGE). Biotechniques. 19: 830-5], the TaqMan system (Holland, P. M. et al., 1991. Detection of specific polymerase chain reaction product by utilizing the 5'→3' exonuclease activity of Thermus aquaticus DNA polymerase. Proc Natl Acad Sci USA. 88: 7276-80), as well as various DNA "chip" technologies such as the GeneChip microarrays (e.g., Affymetrix SNP chips) which are disclosed in U.S. Pat. No. 6,300,063 to Lipshutz, et al. 2001, which is fully incorporated herein by reference, Genetic Bit Analysis (GBA™) which is described by Goelet, P. et al. (PCT Appl. No. 92/15712), peptide nucleic acid (PNA, Ren B, et al., 2004. Nucleic Acids Res. 32: e42) and locked nucleic acids (LNA, Latorra D, et al., 2003. Hum. Mutat. 22: 79-85) probes, Molecular Beacons (Abravaya K, et al., 2003. Clin Chem Lab Med. 41: 468-74), intercalating dye [Germer, S. and Higuchi, R. Single-tube genotyping without oligonucleotide probes. Genome Res. 9:72-78 (1999)], FRET primers (Solinas A et al., 2001. Nucleic Acids Res. 29: E96), AlphaScreen (Beaudet L, et al., Genome Res. 2001, 11(4): 600-8), SNPstream (Bell P A, et al., 2002. Biotechniques. Suppl.: 70-2, 74, 76-7), Multiplex minisequencing (Curcio M, et al., 2002. Electrophoresis. 23: 1467-72), SnaPshot (Turner D, et al., 2002. Hum Immunol. 63: 508-13), MassEXTEND (Cashman J R, et al., 2001. Drug Metab Dispos. 29: 1629-37), GOOD assay (Sauer S, and Gut I G. 2003. Rapid Commun. Mass. Spectrom. 17: 1265-72), Microarray minisequencing (Liljedahl U, et al., 2003. Pharmacogenetics. 13: 7-17), arrayed primer extension (APEX) (Tonisson N, et al., 2000. Clin. Chem. Lab. Med. 38: 165-70), Microarray primer extension (O'Meara D, et al., 2002. Nucleic Acids Res. 30: e75), Tag arrays (Fan J B, et al., 2000. Genome Res. 10: 853-60), Template-directed incorporation (TDI) (Akula N, et al., 2002. Biotechniques. 32: 1072-8), fluorescence polarization (Hsu T M, et al., 2001. Biotechniques. 31: 560, 562, 564-8), Colorimetric oligonucleotide ligation assay (OLA, Nickerson D A, et al., 1990. Proc. Natl. Acad. Sci. USA. 87: 8923-7), Sequence-coded OLA (Gasparini P, et al., 1999. J. Med. Screen. 6: 67-9), Microarray ligation, Ligase chain reaction, Padlock probes, Rolling circle amplification, Invader assay (reviewed in Shi M M. 2001. Enabling large-scale pharmacogenetic studies by high-throughput mutation detection and genotyping technologies. Clin Chem. 47: 164-72), coded microspheres (Rao K V et al., 2003. Nucleic Acids Res. 31: e66) MassArray (Leushner J, Chiu N H, 2000. Mol Diagn. 5: 341-80), heteroduplex analysis, mismatch cleavage detection, and other conventional techniques as described in Sheffield et al. (1991), White et al. (1992), Grompe et al. (1989 and 1993), exonuclease-resistant nucleotide derivative (U.S. Pat. No. 4,656,127).

As mentioned, the expression level of the identified gene may also be analyzed in the sample of the test subject. When the expression level is different (up-regulated or down-regulated, for example by at least 10%, 20%, 30%, 40%, 50%, 100%, 200% or more) to the expression level of that gene in a healthy subject (or to the expression level of that gene in a subject known not to be resistant to the effects of the agent) this is indicative that the candidate therapy should not be used (at least as a single agent) for treating the disease (e.g. it may be ruled out entirely for treating that disease or it may be ruled in for use as combination therapy only, or it may be ruled in for use together with a sensitizing agent).

The expression level of the RNA encoded by the identified gene can be determined using methods known in the arts. These include for example Northern Blot analysis, RT-PCR analysis, RNA in situ hybridization stain, in situ RT-PCR stain, DNA microarrays/DNA chips, oligonucleotide microarray.

The expression level of the protein encoded by the identified gene can be determined using methods known in the arts. These include for example enzyme linked immunosorbent assay (ELISA), Western blot, Radio-immunoassay (RIA), fluorescence activated cell sorting (FACS), immunohistochemical analysis, in situ activity assay and in vitro activity assays.

Using the above disclosed assay, the present inventors have identified two genes, Replication Timing Regulatory Factor 1 (RIF1) and PIN2/TERF1 Interacting, Telomerase Inhibitor 1 (PINX1) which are associated with resistance to a chemotherapeutic agent.

Thus, according to another aspect of the present invention there is provided a method of ruling out treatment of a cancer with a chemotherapeutic agent in a subject comprising analyzing the sequence and/or expression of Replication Timing Regulatory Factor 1 (RIF1) and/or PIN2/TERF1 Interacting, Telomerase Inhibitor 1 (PINX1) in a tumor sample of the subject wherein an alteration in the sequence and/or level of expression of said RIF1 and/or PINX1 as compared to the sequence and/or expression of said RIF1 and/or PINX1 in a control sample is indicative that the chemotherapeutic agent should be ruled out for treating the cancer in the subject.

Exemplary mRNA sequences for human RIF1 are provided in NM_001177663.1, NM_001177664.1, NM_001177665.1, NM_018151.4 and XM_005246665.2.

Exemplary mRNA sequences for human PINX1 are provided in NM_001284356.1 and NM_017884.5.

Exemplary chemotherapeutic agents which may be ruled out using the above described assay are provided herein above. According to a particular embodiment, the chemotherapeutic agent is an antibiotic—e.g. bleomycin.

Methods of analyzing alterations in sequence and/or level of expressions are described herein above.

In one embodiment, when the sequence of the RIF1 or PINX1 in the tumor sample of the subject is different to the sequence of that gene in a healthy subject (or to the sequence of that gene in a subject known not to be resistant to the effects of the agent) this is indicative that the candidate agent should not be used for treating the disease (i.e. it should be ruled out for treating that disease).

In another embodiment, when the expression level of the RIF1 or PINX1 in the tumor sample of the subject is different (up-regulated or down-regulated, for example by at least 10%, 20%, 30%, 40%, 50%, 100%, 200% or more) to the expression level of that gene in a healthy subject (or to the expression level of that gene in a subject known not to be resistant to the effects of the agent) this is indicative that the candidate agent should not be used for treating the disease (i.e. it should be ruled out for treating that disease).

It will be appreciated that once a candidate chemotherapeutic agent has been ruled out, the present inventors contemplate treating the subject with an alternative agent (or additional) known to be useful for treating that type of tumor.

The agents which may be used to determine the expression level of RIF1 and PINX1 may be provided in a kit for the purpose of determining if a subject is likely to be resistant to the effects of a cytotoxic therapy. The kit may comprise how to carry out the assay.

The kit may comprise agents that specifically bind to the DNA/RNA encoding RIF1 and PINX1 (e.g. nucleic acids that hybridize to same) or agents that specifically bind to the proteins themselves (e.g. antibodies).

As used herein the term "about" refers to ±10% The terms "comprises", "comprising", "includes", "including", "having" and their conjugates mean "including but not limited to".

The term "consisting of" means "including and limited to".

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1. Methods

Human Oocyte Manipulation and Parthenogenetic ES Cell Line Derivation:

Human oocyte donation and pES and swaPS cell line derivation procedures were described previously.[15,35]

Briefly, mature MII oocytes were activated using a calcium ionophore and/or an electrical pulse, followed by 4 hour culture with puromycin. Polar body extrusion and the presence of a single pronucleus indicating haploidy were confirmed, and oocytes were allowed to develop to the blastocyst stage. swaPS cells were derived following activation of an oocyte whose nuclear genome had been swapped with that of another oocyte.[15] ES cell lines were derived by laser-ablation of the trophectoderm[38] and addition of ROCK inhibitor Y-27632 at 10 μM to the derivation medium.[35] Two to three days after plating, remaining trophectoderm cells were laser-ablated, and ICM cells were allowed to grow for 10-14 days until manual picking of the outgrowth was feasible.

Cell Culture:

Unless otherwise stated, human ES cells were cultured on a feeder layer of growth-arrested mouse embryonic fibroblasts in standard human ES cell medium composed of Knockout Dulbecco's Modified Eagle's Medium supplemented with 15% Knockout Serum Replacement (KSR, Thermo Fisher Scientific), 2 mM L-glutamine, 0.1 mM nonessential amino acids, 50 units $mL^{-1}$ penicillin, 50 μg $mL^{-1}$ streptomycin, 0.1 mM β-mercaptoethanol and 8 ng $mL^{-1}$ basic fibroblast growth factor (bFGF). Cells were free of *mycoplasma* and maintained in a humidified incubator at 37° C. and 5% $CO_2$. Passaging was carried out either mechanically with gentle trypsinization using Trypsin Solution A without EDTA (Biological Industries), or enzymatically using TrypLE Express (Thermo Fisher Scientific) with addition of 10 μM ROCK inhibitor Y-27632 (Stemgent) for 1 day or up to 2 days after splitting. Haploid ES cells could also be grown in feeder-free conditions on Matrigel-coated plates (Corning) in mTeSR1 (STEMCELL Technologies) or StemFitN.AK03 (Ajinomoto) media. Rapid expansion of the outgrowth allows isolation of haploid ES cells as early as passage 3.

Isolation and Maintenance of Haploid Human ES Cell Lines.

Following identification of haploid cells in human parthenogenetic ES cell lines at passages 6-8 by either metaphase spread analysis or sub-2c cell sorting (Table 1B and Table 2), haploid ES cell lines were established by sorting the 1c cell population, with diploid cells serving as a reference. Haploid ES cell cultures were further maintained by enrichment rounds of 1c cell sorting every 3-4 passages.

TABLE 1B

Identification of haploid cells in early-passage human parthenogenetic ES cell lines by metaphase spread analysis

| pES cell line | Oocyte donor | Passage no. at analysis | No. of haploid metaphases | No. of diploid metaphases | Total no. of metaphases | % Haploid metaphases |
|---|---|---|---|---|---|---|
| 1 | Aug. 31, 2009 | 4 | 0 | 233 | 233 | 0 |
| 2 | 1043 | 6 | 0 | 278 | 278 | 0 |
| 3 | 1058 | 6 | 0 | 273 | 273 | 0 |
| 4 | 1058 | 6 | 0 | 222 | 222 | 0 |
| 5 | 1058 | 9 | 0 | 50 | 50 | 0 |
| 6 | 1105 | 5 | 0 | 13 | 13 | 0 |
|  |  | 10 | 0 | 140 | 140 | 0 |
| 8 | 1151 | 4 | 0 | 361 | 361 | 0 |
| 9 | 1157 | 6 | 0 | 234 | 234 | 0 |
| 10 | 1160 | 7 | 2 | 150 | 152 | 1.32 |
| 11 | 1160 | 8 | 0 | 194 | 194 | 0 |
|  |  | Total: | 2 | 2148 | 2150 |  |

The derivation of cell lines pES1-6 was reported previously.[15,35]

TABLE 2

Isolation of haploid cells from early-passage human parthenogenetic ES cell lines by sub-2c cell sorting

| | Oocyte donor | Passage number at $1^{st}$ sort | Passage number at $2^{nd}$ sort | Presence of haploid cells at $2^{nd}$ sort |
|---|---|---|---|---|
| pES cell line |  |  |  |  |
| 6 | 1105 | 6 | 10 | Undetected |
| 12 | 1160 | 6 | 10 | Yes |
| swaPS cell line* |  |  |  |  |
| 4 | 1126 | 6 | 11 | Undetected |
| 5 | 1155 | 5 | 9 | Undetected |
| 11 | 1175 | 4 | Sorted population did not survive | |

*swaPS cells are parthenogenetic ES cells derived following activation of an oocyte whose nuclear genome had been swapped with that of another oocyte.[35]

Metaphase Spread Analysis:

For induction of mitotic arrest, growing cells were incubated for 40 min in the presence of 100 ng mL-1 colcemid (Biological Industries), added directly to the culture medium, in a humidified incubator at 37° C. with 5% CO2. The cells were then trypsinized, centrifuged at 1000 RPM at room temperature and gently resuspended in 37° C.-warmed hypotonic solution (2.8 mg mL-1 KCl and 2.5 mg mL-1 sodium citrate) followed by 20-min incubation at 37° C. Cells were fixed by addition of fixative solution (3:1 methanol:acetic acid) and incubation for 5 min at room temperature. Fixation was repeated at least three times following centrifugation and resuspension in fixative solution. Metaphase spreads were prepared on slides and stained using the standard G-banding technique. Karyotype integrity was determined according to the International System for Human Cytogenetic Nomenclature (ISCN) based on the observation of a normal karyotype in at least 80% of analyzed metaphases (minimum of 20 metaphases per analysis).

Live ES Cell Sorting by DNA Content:

Cells were washed with phosphate buffered saline (PBS), dissociated using either TrypLE Select or TrypLE Express (Thermo Fisher Scientific) and stained with 10 µg mL$^{-1}$ Hoechst 33342$^2$ (Sigma-Aldrich) in human ES cell medium at 37° C. for 30 min. Following centrifugation, cells were resuspended in PBS containing 15% KSR and 10 µM ROCK inhibitor Y-27632, filtered through a 70-µm cell strainer (Corning) and sorted using the 405 nm laser in either BD FACSAria III or BD Influx (BD Biosciences). For continued growth, sorted cells were plated with fresh medium containing 10 µM ROCK inhibitor Y-27632 for 24 hours. For comparative analyses, G1-phase cells were sorted from isogenic haploid-enriched and unsorted diploid cultures. Cells that had undergone diploidization relatively recently in culture (within 3 passages after haploid cell enrichment) were isolated by sorting the G2/M-phase peak in haploid-enriched cultures and compared with G2/M-phase diploid cells from unsorted diploid cultures. Note that haploid-enriched cultures also consist of a mixed population of G2/M-phase haploids and G1-phase diploids. Sorting purity was confirmed by rerunning a fraction of sorted samples through the instrument.

Flow Cytometry:

All DNA content profiles were generated based on flow cytometry with Hoechst 33342 staining. Haploid cell proportion was estimated based on the percentage of 1c cells and the relative contribution of G1 cells with regards to other phases of the cell cycle. Estimation of diploidization rate was based on the proportion of haploid cells between consecutive enrichment rounds as well as experimental analysis of h-pES10 diploidization kinetics throughout 7 passages (30 days) by analyzing the DNA content of 2-3 replicates at each passage using flow cytometry with propidium iodide in methanol-fixed and RNase-treated cells. Diploidization rate was estimated by fitting the data to an exponential decay curve. For simultaneous flow cytometry analysis of DNA content and cell surface molecules, cells were washed, dissociated and incubated on ice for 30 min in the presence of 10 µg mL$^{-1}$ Hoechst 33342 (Sigma-Aldrich) and either a conjugated antibody or a secondary antibody diluted 1:200 following a 60 min incubation with a primary antibody. For simultaneous flow cytometry analysis of DNA content and intracellular PDX1, dissociated cells were treated as described for immunofluorescence procedures, with Hoechst 33342 for DNA staining. Primary antibodies are detailed in Table 3. In all flow cytometry procedures, samples were filtered through a 70-µm cell strainer (Corning Life Sciences) and analyzed in either BD FACSAria III or BD Influx (BD Biosciences).

TABLE 3

Primary antibodies used in the Examples

| Antibody | Host species | Type | Isotype | Dilution | Vendor | Catalog no. | Assay |
|---|---|---|---|---|---|---|---|
| Anti-centromere | Human | Polyclonal | NA | 1:50 | Antibodies Incorporated | 15-235-0001 | IF |
| Anti-pH3 | Rabbit | Polyclonal | NA | 1:1,000 | EMD Millipore | 06-570 | IF |
| Anti-human NANOG | Goat | Polyclonal | IgG | 1:100 | R&D Systems | AF1997 | IF |
| Anti-human OCT4 | Goat | Polyclonal | IgG | 1:100 | Santa Cruz Biotechnology | sc-8628 | IF |
| Anti-human SOX2 | Rabbit | Polyclonal | IgG | 1:100 | Stemgent | 09-0024 | IF |
| Anti-human/mouse SSEA4 | Mouse | Monoclonal | IgG | 1:500 | R&D Systems | MAB1435 | IF |
| Alexa Fluor ® 488-conjugated anti-human TRA-1-60 | Mouse | NA | IgM | 1:100 | BD Biosciences | 560173 | IF |
| PE-conjugated anti-human TRA-1-60 | Mouse | Monoclonal | IgM | 1:40 | BD Biosciences | 560884 | FC |
| Anti-human CLDN6 | Mouse | Monoclonal | IgG | 1:40 | R&D Systems | MAB3656 | FC |
| Anti-H3K27me3 | Rabbit | Polyclonal | IgG | 1:400 | EMD Millipore | 07-449 | IF |
| Anti-human NCAM-1/CD56 | Goat | Polyclonal | IgG | 1:150 | R&D Systems | AF2408 | FC |

TABLE 3-continued

Primary antibodies used in the Examples

| Antibody | Host species | Type | Isotype | Dilution | Vendor | Catalog no. | Assay |
|---|---|---|---|---|---|---|---|
| Anti-human FOXA2 | Rabbit | Polyclonal | NA | 1:200 | Cell Signaling Technology | 3143 | IF |
| Anti-human TUJ1 | Rabbit | NA | NA | 1:300 | Sigma-Aldrich | T2200 | IF |
| Anti-human TNNT2 | Rabbit | Polyclonal | IgG | 1:100 | Abcam | ab45932 | IF |
| Anti-human NKX6.1 | Mouse | Monoclonal | IgG | 1:300 | DSHB | F55A10 | IF |
| Anti-human PDX1 | Goat | Polyclonal | IgG | 1:200 | R&D Systems | AF2419 | IF, FC |
| Anti-human NKX6.1 | Mouse | Monoclonal | IgG | 1:300 | DSHB | F55A10 | IF |
| Anti-human α-SMA | Mouse | Monoclonal | IgG | 1:500 | Dako | M0851 | IF |
| Anti-human AFP | Rabbit | Polyclonal | NA | 1:500 | Dako | A0008 | IF |

NA: not available.
IF: immunofluorescence staining.
FC: flow cytometry.

DNA Fluorescence In Situ Hybridization:

DNA FISH was performed as described elsewhere[39] using probes for human chromosomes 2 and 4 and DNA staining with 4',6-diamidino-2-phenylindole (DAPI). Haploidy and diploidy were respectively determined per nucleus based on single or double hybridization signals. ES cells subject to FISH were grown on Matrigel-coated MATEK glass plates for several passages prior to analysis.

Alkaline Phosphatase and Immunofluorescence Staining:

Alkaline phosphatase staining was performed using the Leukocyte Alkaline Phosphatase Kit (Sigma-Aldrich). For immunofluorescence staining, samples were washed with PBS, fixed with 4% paraformaldehyde for 10 min, and permeabilized and blocked in blocking solution (0.1% Triton X-100 and 5% donkey serum in PBS). Cells were incubated with primary antibodies (Table 3) and secondary antibodies diluted 1:500 in blocking solution, and DAPI was used for DNA staining. Cells were washed twice with PBS subsequently to fixation and each incubation step. Images were taken using a Zeiss LSM 510 Meta Confocal Microscope. Centromere quantification was carried out by manually counting centromere foci across individual planes along the Z axis. EdU staining was performed using the Click-iT EdU Alexa Fluor 488 Imaging Kit (Thermo Fisher Scientific). ES cells subject to centromere staining in FIG. 1G and FIG. 5D were grown on Matrigel-coated MATEK glass plates for several passages prior to analysis.

6-TG Resistance Screen:

To generate a gene trap mutant library, 9 replicates of 4-5×10[6] haploid pES10 cells (within one passage after 1c-cell enrichment) were co-transfected with 20 μg 5'-PTK-3' gene trap vector[52] and 20 μg pCyL43 piggyBac transposase plasmid[53] using Bio-Rad Gene Pulser (suspended in 800 μL Opti-MEM, 4-mm cuvettes, 320 V, 250 μF), and replated on a 100×20 mm dish with DR3 MEFs and ROCK inhibitor Y-27632. Selection for insertions into expressed loci was carried out using 0.3 μg mL$^{-1}$ puromycin starting 48 hours post transfection, followed by pooling into a single library, represented by approximately 16,000 resistant colonies. Transfection with 5'-PTK-3' only was used as a negative control. To screen for 6-TG-resistant mutants, the mutant library was grown in the presence of 6 μM 6-TG (Sigma-Aldrich) on DR4 MEFs for 18 days, during which 6 resistant colonies were independently isolated and characterized. Genomic DNA was extracted (NucleoSpin Tissue Kit, MACHEREY-NAGEL) and insertion sites were detected using splinkerette PCR as described previously,[54] followed by PCR product purification and Sanger sequencing (ABI PRISM 3730×1 DNA Analyzer (Applied Biosystems)). Sequences were mapped to the human genome (GRCh38/hg38) using UCSC BLAT search tool.

Isolation of Total DNA and RNA.

Total DNA was isolated using the NucleoSpin Tissue Kit (MACHEREY-NAGEL). Total RNA was isolated using Qiagen RNeasy Kits according to the manufacturer's protocols. To determine total RNA levels per cell, haploid and diploid cells were isolated from the same cultures by sorting the 1c (haploid G1) and 4c (diploid G2/M) populations, respectively. Following growth for 2 passages, cells were harvested and counted, and RNA was isolated from triplicates of 400,000 cells from each cell line and ploidy state (pES10 and pES12, haploid and diploid; 12 samples in total). RNA amounts were quantified using NanoDrop.

Genome Integrity Analysis:

Copy number variation (CNV) analysis was carried out on DNA samples of G1-sorted haploid and diploid pES10 and pES12 cells (Table 4) using Infinium Omni2.5Exome-8 BeadChip single nucleotide polymorphism (SNP) arrays (Illumina) following the manufacturer's protocols. Raw data were processed using Genome Studio Genotyping Module (Illumina) to obtain log R ratios values for analysis using R statistical programming language.

TABLE 4

Samples analyzed by SNP arrays and DNA methylation arrays

| Sample no. | Sample name | Cell line | Passage | Description | Assay* |
|---|---|---|---|---|---|
| 1 | pES10 h-G1 rep1 | h-pES10 | 15 | Haploid ES cells in G1 (1c), 3$^{rd}$ sort, biological replicate 1 | M, S |
| 2 | pES10 h-G1 rep2 | h-pES10 | 19 | Haploid ES cells in G1 (1c), 4$^{th}$ sort, biological replicate 2 | M |
| 3 | pES10 d-G1 rep1 | d-pES10 | 17 | Diploid ES cells in G1 (2c), technical replicate 1 | M, S |
| 4 | pES10 d-G1 rep2 | d-pES10 | 17 | Diploid ES cells in G1 (2c), technical replicate 2 | M |
| 5 | h-pES10 d-G2/M | h-pES10 | 15 | Diploid ES cells in G2/M from a mixed haploid-diploid culture (4c), 3$^{rd}$ sort | M |
| 6 | pES12h-G1 rep1 | h-pES12 | 18 | Haploid ES cells in G1 (1c), 4$^{th}$ sort, biological replicate 1 | M, S |
| 7 | pES12 h-G1 rep2 | h-pES12 | 22 | Haploid ES cells in G1 (1c), 5$^{th}$ sort, biological replicate 2 | M |
| 8 | pES12 d-G1 rep1 | d-pES12 | 18 | Diploid ES cells in G1 (2c), biological replicate 1 | M, S |
| 9 | pES12 d-G1 rep2 | d-pES12 | 18 | Diploid ES cells in G1 (2c), biological replicate 2 | M |
| 10 | NYSCF2 | NYSCF2 | 20 | Diploid IVF ES cell line | M |
| 11 | HuES53 | HuES53 | <20 | Diploid IVF ES cell line | M |
| 12 | HuES64 | HuES64 | <20 | Diploid IVF ES cell line | M |

*M: DNA methylation analysis. S: SNP array analysis.

RNA Sequencing:

Total RNA samples (200 ng-1 µg, RNA integrity number (RIN) >9) were enriched for mRNAs by pull-down of poly(A)$^+$ RNA. RNA-Seq libraries were prepared using the TruSeq RNA Library Prep Kit v2 (Illumina) according to the manufacturer's protocol and sequenced using Illumina NextSeq 500 to generate 85 bp single-end reads. Table 5 provides a detailed list of samples analyzed by RNA-Seq.

TABLE 5

Samples analyzed by RNA-Seq

| Sample no. | Sample name | Cell line | Passage | Description |
|---|---|---|---|---|
| 1 | pES10 h-G1 rep1 | h-pES10 | 15 | Haploid ES cells in G1 (1c), 3$^{rd}$ sort, biological replicate 1 |
| 2 | pES10 h-G1 rep2 | h-pES10 | 19 | Haploid ES cells in G1 (1c), 4$^{th}$ sort, biological replicate 2 |
| 3 | pES10 d-G1 rep1 | d-pES10 | 13 | Diploid ES cells in G1 (2c), biological replicate 1 |
| 4 | pES10 d-G1 rep2 | d-pES10 | 17 | Diploid ES cells in G1 (2c), biological replicate 2 |
| 5 | h-pES10 d-G2/M | h-pES10 | 15 | Diploid ES cells in G2/M from a mixed haploid-diploid culture (4c), 3$^{rd}$ sort |
| 6 | d-pES10 d-G2/M | d-pES10 | 13 | Diploid ES cells in G2/M from a diploid culture (4c) |
| 7 | pES12 h-G1 rep1 | h-pES12 | 18 | Haploid ES cells in G1 (1c), 4$^{th}$ sort, biological replicate 1 |
| 8 | pES12 h-G1 rep2 | h-pES12 | 22 | Haploid ES cells in G1 (1c), 5$^{th}$ sort, biological replicate 2 |
| 9 | pES12 d-G1 rep1 | d-pES12 | 18 | Diploid ES cells in G1 (2c), biological replicate 1 |
| 10 | pES12 d-G1 rep2 | d-pES12 | 18 | Diploid ES cells in G1 (2c), biological replicate 2 |
| 11 | pES10 NPC h-G1 | h-pES10 | 21 | Haploid NCAM1$^+$ NPCs in G1 (1c) derived from ES cells after 4$^{th}$ sort + 10 days culture + 10 days differentiation |
| 12 | pES10 EB h-G1 | h-pES10 | 25 | Haploid EB cells in G1 (1c) derived from ES cells after the 5$^{th}$ sort + 13 days culture + 21 days differentiation |
| 13 | pES10 EB d-G1 | d-pES10 | 12 | Diploid EB cells in G1 (2c) derived from ES cells after 21 days differentiation |
| 14 | pES10 EB d-unsorted | d-pES10 | 12 | Unsorted diploid EBs derived from ES cells after 21 days differentiation |
| 15 | pES12 EB d-unsorted | d-pES12 | 19 | Unsorted diploid EBs derived from ES cells after 21 days differentiation |
| 16 | HuES53 | HuES53 | <20 | Diploid IVF ES cell line |
| 17 | HuES64 | HuES64 | <20 | Diploid IVF ES cell line |

Transcriptome Analysis:

RNA-Seq reads were aligned to the human reference genome (GRCh37/hg19) using TopHat (version 2.0.8b) allowing 5 mismatches. Reads per kilobase per million fragments mapped (RPKM) values were quantified using Cuffquant and normalized using Cuffnorm in Cufflinks (version 2.1.1) to generate relative gene expression levels. Hierarchical clustering analyses were performed on RPKM values using Pearson correlation and average linkage. Analysis of differential gene expression relative to total RNA in haploid and diploid human ES cells (n=4 in each group) was carried out by two complementary strategies, as follows: first, we used Cuffdiff with default parameters, considering differences of >2-fold with FDR <0.05 as significant; second, to identify possibly subtle yet consistent transcriptional differences, we tested for genes whose minimal expression levels across all replicates of a certain group were higher than their maximal expression level across all replicates of the other group. Statistical significance was then determined by two-tailed unpaired Student's t test. Functional annotation enrichment analysis was done by DAVID (using the Benjamini method to determine statistical significance). Imprinting analyses included 75 human imprinted genes (see the Geneimprint website), listed in Table 6. RNA-Seq data from control ES cell line NYSCF1 were published elsewhere[37] (GEO accession number GSE61657). Genome-wide gene expression moving median plots were generated using the R package zoo (version 1.7-12) after removal of genes that were not expressed in the averaged reference diploid sample by flooring to 1 and setting an expression threshold of above 1. RNA-Seq data from different tissues were retrieved from the Genotype-Tissue Expression (GTEx) Portal.[40] Color-coded scales in FIG. 4D correspond to gene expression levels relative to the mean across tissues (left scale) and across each set of ES cell duplicate and EB sample (right scale). Expression microarray analysis was performed as previously[41] by using Affymetrix Human Gene 1.0 ST arrays.

TABLE 6

Imprinted genes used for hierarchical clustering analysis

| Gene | ID | Locus |
|---|---|---|
| TP73 | ENSG00000078900 | chr1: 3547330-3663900 |
| RNU5D-1 | ENSG00000200169 | chr1: 45196726-45196842 |
| DIRAS3 | ENSG00000162595 | chr1: 68167148-68698803 |
| LRRTM1 | ENSG00000162951 | chr2: 79384131-80875905 |
| GPR1 | ENSG00000183671 | chr2: 207040039-207082771 |
| ZDBF2 | ENSG00000204186 | chr2: 207139386-207179148 |
| NAP1L5 | ENSG00000177432 | chr4: 89442135-89629693 |
| FAM50B | ENSG00000145945 | chr6: 3832166-3855971 |
| LIN28B | ENSG00000187772 | chr6: 105404922-105531207 |
| AIM1 | ENSG00000112297 | chr6: 106959793-107018326 |
| PLAGL1 | ENSG00000118495 | chr6: 144261436-144385735 |
| SLC22A2 | ENSG00000112499 | chr6: 160592092-160698670 |
| SLC22A3 | ENSG00000146477 | chr6: 160769299-160932156 |
| DDC | ENSG00000132437 | chr7: 50526133-50633154 |
| GRB10 | ENSG00000106070 | chr7: 50657759-50861159 |
| MAGI2 | ENSG00000187391 | chr7: 77646392-79100524 |
| TFPI2 | ENSG00000105825 | chr7: 93220884-93540577 |
| SGCE | ENSG00000127990 | chr7: 94214541-94285521 |
| PEG10 | ENSG00000242265 | chr7: 94285636-94299007 |
| PPP1R9A | ENSG00000158528 | chr7: 94536513-94925727 |
| DLX5 | ENSG00000105880 | chr7: 96649703-96654409 |
| CPA4 | ENSG00000128510 | chr7: 129932973-129964020 |
| MEST | ENSG00000106484 | chr7: 130125882-130148500 |
| KLF14 | ENSG00000174595 | chr7: 130417400-130418888 |
| DLGAP2 | ENSG00000198010 | chr8: 1449531-1656642 |
| ZFAT | ENSG00000066827 | chr8: 135490030-135725292 |
| ZFAT-AS1 | ENSG00000248492 | chr8: 135490030-135725292 |

TABLE 6-continued

Imprinted genes used for hierarchical clustering analysis

| Gene | ID | Locus |
|---|---|---|
| KCNK9 | ENSG00000169427 | chr8: 140613080-140715299 |
| GLIS3 | ENSG00000107249 | chr9: 3824126-4348392 |
| INPP5F | ENSG00000198825 | chr10: 121485608-121588652 |
| H19 | ENSG00000130600 | chr11: 2016405-2022700 |
| IGF2 | ENSG00000167244 | chr11: 2150341-2182571 |
| IGF2-AS | ENSG00000099869 | chr11: 2150341-2182571 |
| INS | ENSG00000254647 | chr11: 2150341-2182571 |
| KCNQ1 | ENSG00000053918 | chr11: 2465913-2882798 |
| KCNQ1OT1 | ENSG00000269821 | chr11: 2465913-2882798 |
| KCNQ1DN | ENSG00000237941 | chr11: 2891262-2893335 |
| CDKN1C | ENSG00000129757 | chr11: 2904442-2907111 |
| SLC22A18 | ENSG00000110628 | chr11: 2909009-2946476 |
| PHLDA2 | ENSG00000181649 | chr11: 2949502-2950685 |
| OSBPL5 | ENSG00000021762 | chr11: 3108345-3187969 |
| WT1 | ENSG00000184937 | chr11: 32409320-32480315 |
| ANO1 | ENSG00000131620 | chr11: 69924407-70035634 |
| ZC3H12C | ENSG00000149289 | chr11: 109964086-110042566 |
| NTM | ENSG00000182667 | chr11: 131240372-132206716 |
| RBP5 | ENSG00000139194 | chr12: 7276279-7281538 |
| RB1 | ENSG00000139687 | chr13: 48877886-49056122 |
| DLK1 | ENSG00000185559 | chr14: 101192041-101201539 |
| MEG3 | ENSG00000214548 | chr14: 101245746-101327368 |
| RTL1 | ENSG00000254656 | chr14: 101346991-101351184 |
| MKRN3 | ENSG00000179455 | chr15: 23810453-23873064 |
| MAGEL2 | ENSG00000254585 | chr15: 23888690-23891175 |
| NDN | ENSG00000182636 | chr15: 23930564-23932450 |
| NPAP1 | ENSG00000185823 | chr15: 24920540-24928593 |
| SNRPN | ENSG00000128739 | chr15: 25068793-25492435 |
| SNURF | ENSG00000273173 | chr15: 25068793-25492435 |
| UBE3A | ENSG00000114062 | chr15: 25497371-25684128 |
| ATP10A | ENSG00000206190 | chr15: 25922419-26110317 |
| NAA60 | ENSG00000262621 | chr16: 3415098-3627401 |
| ZNF597 | ENSG00000167981 | chr16: 3415098-3627401 |
| TCEB3C | ENSG00000183791 | chr18: 44388352-44627658 |
| DNMT1 | ENSG00000130816 | chr19: 10244020-10341962 |
| MIR371A | ENSG00000199031 | chr19: 54290850-54291423 |
| NLRP2 | ENSG00000022556 | chr19: 55434876-55512510 |
| PEG3 | ENSG00000198300 | chr19: 57202053-57352097 |
| ZIM2 | ENSG00000269699 | chr19: 57202053-57352097 |
| MIMT1 | ENSG00000268654 | chr19: 57352269-57359924 |
| BLCAP | ENSG00000166619 | chr20: 36120873-36156333 |
| NNAT | ENSG00000053438 | chr20: 36120873-36156333 |
| MIR296 | ENSG00000268649 | chr20: 57392186-57392780 |
| MIR298 | ENSG00000216031 | chr20: 57393280-57393368 |
| GNAS | ENSG00000087460 | chr20: 57393973-57486247 |
| GNAS-AS1 | ENSG00000235590 | chr20: 57393973-57486247 |
| DGCR6 | ENSG00000183628 | chr22: 18893540-18924066 |
| DGCR6L | ENSG00000128185 | chr22: 20301798-20307603 |

DNA Methylation Analysis:

DNA methylation analysis was performed on genomic DNA from the samples detailed in Table 4 using Infinium HumanMethylation450 BeachChips (Illumina) following the Infinium HD Methylation Protocol as described previously.[37] DNA methylation data from control ES cell line NYSCF1 were published before (GEO accession number GSE61657).[37] Data were processed and normalized by using subset-quantile within array normalization (SWAN) and adjusted for batch effects using the R package ChAMP (version 1.4.0). DNA methylation levels at CpG sites associated with pluripotency-specific genes and iDMRs were analyzed as described before.[37] For analysis of DNA methylation levels on the X chromosome, probes with average β values of less than 0.4 were filtered out. DMR analysis was facilitated by the lasso function in ChAMP using default settings. DMRs were then assigned to genes by proximity and analyzed for functional annotation enrichment using DAVID (using the Benjamini method to determine statistical significance).

Cell Size Analysis:

Following sorting of haploid and diploid cell populations in G1, the diameter (2r) of viable single cells was measured by Countess Automated Cell Counter (Invitrogen) and their surface area and volume were calculated as $4\pi r^2$ and $4/3\pi r^3$, respectively. Analysis included 7, 4, 8 and 4 technical replicates for 1n pES10, 1n pES12, 2n pES10 and 2n pES12, respectively.

Mitochondrial DNA Abundance Analysis:

Relative mtDNA abundance was analyzed by quantitative PCR (qPCR) by using primers for the mitochondrial gene ND2 (forward primer: 5'-TGTGGHTATACCCTFCCCGTACTA-3' (SEQ ID NO: 1); reverse primer: 5'-CCTGCAAAGATGGTAGAGTAGATGA-3' (SEQ ID NO: 2)) and normalization to nuclear DNA by using primers for the nuclear gene BECNJ (forward primer: 5'-CCCTCATCACAGGGCTCTCTCCA-3' (SEQ ID NO: 3); reverse primer: 5'-GGGACTGTAGGCTGGGAACTATGC-3' (SEQ ID NO: 4)), as described elsewhere.[42] Analysis was performed using Applied Biosystems 7300 Real-Time PCR System with PerfeCTa SYBR Green FastMix (Quanta Biosciences). Analysis included all G1-sorted samples detailed in Table 4 (n=4 for each group, with two biological replicates for each cell line).

All high-throughput data have been deposited at the Gene Expression Omnibus (GEO) under accession number GSE71458.

Embryoid Body Differentiation:

EB differentiation was carried out by detaching ES cell colonies with Trypsin Solution A without EDTA (Biological Industries), followed by resuspension and further culture of cell aggregates in human ES cell medium without bFGF on low attachment plates. Differentiation of haploid ES cells was initiated within 2 passages after 1c-cell enrichment. After 21 days, EB RNA was extracted from unsorted and/or sorted EB cells in G1 following dissociation and staining with 10 µg mL$^{-1}$ Hoechst 33342 (Sigma-Aldrich) at 37° C. for 30 min. Metaphase spread analysis was performed on dissociated EB cells plated on 0.2% gelatin and expanded in human ES cell medium without bFGF.

Differentiation into Neural Progenitor Cells:

NCAM1-positive ES cell-derived NPCs were obtained using a 10-days protocol for efficient neural differentiation[43] with slight modification.[44] Differentiation was initiated within 2 passages after 1c-cell enrichment. RNA was extracted from sorted haploid NCAM1-positive cells in G1 by co-staining with Hoechst 33342 and an anti-human NCAM-1/CD56 primary antibody and a Cy3-conjugated secondary antibody (Jackson Immunoresearch Laboratories) diluted 1:200.

Neuronal Differentiation:

Differentiation into neurons was carried out by following a published protocol[45] based on synergistic inhibition of SMAD signaling[46] with modification, as follows: differentiation was initiated within 2 passages after 1c-cell enrichment with fully confluent ES cells cultured on Matrigel-coated plates in mTeSR1 by replacing the medium with human ES cell medium without bFGF, containing 10 µM SB431542 (Selleckchem) and 2.5 µM LDN-193189 (Stemgent) for 4 days. Subsequently, cells were kept in N2 medium[45] supplemented with 10 µM SB431542 and 2.5 µM LDN-193189 for additional 4 days, followed by 2 days in N2 medium supplemented with B-27 (Thermo Fisher Scientific) and 10 µM DAPT (Stemgent). The cells were then dissociated and replated on 0.01% poly-L-ornithine-(Sigma-Aldrich) and laminin-coated (4 µg/ml, Thermo Fisher Scientific) plates in the presence of 10 µM ROCK inhibitor Y-27632 (Selleckchem), and further cultured in the same medium without Y-27632 for the next 4 days. Neuronal cultures were maintained in N2 medium supplemented with B-27 and 20 ng$^{-1}$ BDNF (R&D) until analysis by immunostaining and FISH on day 20.

Cardiomyocyte Differentiation:

80-90% confluent ES cells grown on Matrigel-coated plates (Corning) in mTeSR1 (STEMCELL Technologies) were subject to an 11-days regimen[47] based on consecutive GSK3 and WNT inhibition with CHIR99021 and IWP-2 (Selleckchem), respectively. Differentiation was initiated within 2 passages after 1c-cell enrichment. On day 11 of differentiation, 1c-cells were sorted and plated for immunostaining.

Differentiation Toward the Pancreatic Lineage:

The protocol utilized here was developed based on several recent publications.[48-50] ES cells grown in feeder-free conditions were differentiated into definitive endoderm by using STEMdiff Definitive Endoderm Kit (Stemcell Technologies) for 3-4 days. Subsequent specification was achieved by a step-wise protocol involving treatment with recombinant human KGF/FGF7 (R&D Systems), LDN-193189 (Stemgent), KAAD-cyclopamine (Stemgent) and retinoic acid (Stemgent). On days 8-11, EGF (R&D System) was used to induce pancreatic progenitor cells (PPCs). Differentiation was initiated within 2 passages after 1c-cell enrichment.

Teratoma Formation Assay:

All experimental procedures in animals were approved by the ethics committee of the Hebrew University. ES cells were trypsinized and approximately 2×10$^6$ cells were resuspended in 100 µL human ES cell medium and 100 µL Matrigel (BD Biosciences), followed by subcutaneous injection into NOD-SCID Il2rg$^{-/-}$ immunodeficient mice (Jackson Laboratory). Eight to twelve weeks after injection, tumors were dissected and subjected to further analysis. Histological slides were prepared from tumor slices cryopreserved in O.C.T. compound (Sakura Finetek) using Leica CM1850 cryostat (Leica Biosystems, 10-µm sections), followed by immunostaining, hematoxylin and eosin staining or FISH analysis. Flow cytometry with Hoechst 33342 staining was performed on dissociated cells from freshly dissected tumors.

Example 2. Determination of Ploidy at Single-Cell Level by Quantification of Centromere Foci We devised a methodology for determining ploidy at single-cell resolution based on centromere protein immunofluorescence staining. As each chromosome normally has one centromere, we reasoned that being able to detect and enumerate centromeres would provide a means to visualize ploidy in individual cells, while also allowing to define cellular identity by co-staining for specific markers.

We first tested this method on cell lines of known ploidies, including haploid-enriched and diploid pES10 cells, triploid soPS2 cells[35] and tetraploid Hybrid1 cells,[36] demonstrating a correlation between ploidy and the counted number of centromeres (FIG. 6A). Centromere counts were within with the expected range of chromosome number. 76% of the haploid-enriched cells showed 15-25 centromere foci, whereas the remaining cells showed 30-48 foci, similar to the range documented in diploid cells (34-51). Importantly, this percentage of haploid cells was consistent with that estimated by DNA FISH (73%, FIG. 6B) and DNA content flow cytometry (73%, FIG. 6C), indicating that centromere foci quantification is a reliable method for identifying haploid ES cells.

The accuracy of counting centromeres decreased with increasing ploidy, due to centromere clustering, which would lead to an underestimation of the actual number of individual centromeres, as well as difficulties in counting large numbers of centromeres in single cells. Observing higher numbers of foci than expected could be explained by visual artifacts or aneuploidy in rare cells. To address whether cell cycle progression altered centromere foci numbers or affected their quantification, we co-stained haploid ES cells for centromere protein and either phospho-histone 3 (pH3, Ser10) or 5-ethynyl-2'-deoxyuridine (EdU) (marking cells entering mitosis and undergoing DNA replication, respectively), to quantify the number of centromeres at different stages of the cell cycle (FIGS. 6D-F). Evidently, centromere foci numbers did not increase during DNA replication, confirming that haploid cells can be accurately detected throughout interphase by centromere staining.

Example 3. Derivation of Haploid Human ES Cells

We generated and analyzed a collection of 14 early-passage (passage ≤9) human pES cell lines for the persistence of haploid cells. All cell lines originated from activated oocytes displaying second polar body extrusion and a single pronucleus. We initially utilized chromosome counting by metaphase spreading and G-banding as a method for unambiguous and quantitative discovery of rare haploid nuclei. Among ten individual pES cell lines, a low proportion of haploid metaphases was found exclusively in a single cell line, pES10 (1.3%, Table 1B). We also used viable FACS with Hoechst 33342 staining, aiming to isolate cells with a DNA content corresponding to less than two chromosomal copies (2c) from four additional lines, leading to the successful enrichment of haploid cells from a second cell line, pES12 (Table 2).

Two individual haploid-enriched ES cell lines were established from both pES10 and pES12 (hereafter referred to as h-pES10 and h-pES12) within five to six rounds of 1c-cell FACS enrichment and expansion (FIG. 1C (pES10), FIG. 5A (pES12)). These cell lines were grown in standard culture conditions for over 30 passages while including cells with a normal haploid karyotype (FIG. 1D, FIG. 5B). However, since diploidization occurred at a rate of 3-9% of the cells per day (FIG. 1E), cell sorting at every three to four passages was required for maintenance and analysis of haploid cells. Further, visualization of ploidy in adherent conditions was enabled by DNA fluorescence in situ hybridization (FISH) (FIG. 1F, FIG. 5c) and quantification of centromere protein foci (FIG. 1G, FIG. 5D; FIG. 6). In addition to their intact karyotype, haploid ES cells did not harbor significant copy number variations (CNVs) relative to their unsorted diploid counterparts (FIG. 5E). Importantly, we did not observe common duplications of specific regions in the two cell lines that would result in pseudo-diploidy. Therefore, genome integrity was preserved throughout haploid-cell isolation and maintenance. As expected, single nucleotide polymorphism (SNP) array analysis demonstrated complete homozygosity of diploid pES10 and pES12 cells across all chromosomes.

Both h-pES10 and h-pES12 exhibited classical human pluripotent stem cell features, including typical colony morphology and alkaline phosphatase activity (FIG. 2A, FIG. 2B). Single haploid ES cells expressed various hallmark pluripotency markers (NANOG, OCT4, SOX2, SSEA4 and TRA1-60), as confirmed in essentially pure haploid cultures by centromere foci quantification (>95% haploids) (FIG. 2C, FIG. 7). Notably, selective flow cytometry enabled to validate the expression of two human ES-cell-specific cell surface markers (TRA-1-60 and CLDN6[18]) in single haploid cells (FIG. 2D). Moreover, sorted haploid and diploid ES cells showed highly similar transcriptional and epigenetic signatures of pluripotency genes (FIG. 2E, FIG. 2F). Since the haploid ES cells were derived as parthenotes, they featured distinct transcriptional and epigenetic profiles of maternal imprinting, owing to the absence of paternally-inherited alleles (FIG. 8).

Haploid cells are valuable for loss-of-function genetic screening because phenotypically-selectable mutants can be identified upon disruption of a single allele. To demonstrate the applicability of this principle in haploid human ES cells, we generated a genome-wide mutant library using a piggy-Bac transposon gene trap system that targets transcriptionally active loci (FIG. 2G, FIG. 8E), and screened for resistance to the purine analog 6-thioguanine (6-TG). Out of six isolated and analyzed 6-TG-resistant colonies, three harbored a gene trap insertion localizing to the nucleoside diphosphate linked moiety X-type motif 5 (NUDT5) autosomal gene (FIG. 2H). NUDT5 disruption was recently confirmed to confer 6-TG resistance in human cells,[51] by acting upstream to the production of 5-phospho-D-ribose-1-pyrophosphate (PRPP), which serves as a phosphoribosyl donor in the hypoxanthine phosphoribosyltransferase 1 (HPRT1)-mediated conversion of 6-TG to thioguanosine monophosphate (TGMP) (FIG. 2I). Detection of a loss-of-function phenotype due to an autosomal mutation validates that genetic screening is feasible in haploid human ES cells.

Example 4. Molecular and Cellular Comparisons of Haploid and Diploid ES Cells

The ability of human ES cells to exist both as haploids and diploids led us to investigate whether these two ploidy states may differ in certain aspects of gene regulation and cell biology. To analyze haploid and diploid ES cells in the same phase of the cell cycle, we used FACS to isolate G1-phase haploid cells (1c) and compared them with isogenic G1-phase diploid cells (2c) from unsorted diploid cultures (FIG. 3A, FIG. 9A). We first aimed to uncover putative ploidy-associated differences by comparing the transcriptomes of haploid and diploid ES cells using RNA sequencing (RNA-Seq), considering that observed changes in expression levels would be relative to the total gene expression of each ploidy state, rather than representing absolute differences. On the genome-scale, undifferentiated haploid and diploid ES cells clustered closely with one another and separately from differentiated embryoid bodies (EBs), indicating resemblance that extends beyond the effects of genetic background (FIG. 3B). Nonetheless, a total of 565 differentially expressed genes were identified (>2-fold change, false discovery rate (FDR)<0.05), corresponding to 275 relatively upregulated genes and 290 relatively down-regulated genes in haploids compared with diploids (FIG. 9B).

Notably, X chromosomal genes were significantly over-represented among the relatively upregulated gene set (40%, $P<0.001$, $\chi^2$ goodness of fit test) (FIG. 3C), and the expression levels of X chromosomal genes alone clearly distinguished between haploid and diploid ES cells; the latter clustering even more closely with their differentiated derivatives than their undifferentiated haploid counterparts (FIG. 3D). These data are in line with an expected differential status of X chromosome inactivation (XCI) in haploid and diploid human ES cells: while the single X chromosome in haploids is transcriptionally active ($X_a$), one of the two X chromosomes in diploids often undergoes XCI ($X_aX_i$)[19] as in female somatic cells. Indeed, haploid human ES cells exhibited a relative increase in X chromosomal gene expression compared with diploids by both RNA-Seq and expression microarray analysis, and lacked expression of the XCI-driving transcript XIST (FIG. 3E, FIG. 3F, FIGS. 9B-D), as observed in diploid $X_aX_a$ human ES cells[20]. XCI is an epigenetic phenomenon, regulated by repressive histone modifications and DNA methylation. H3K27me3 foci were consistently observed in unsorted diploid ES cells, but not in their haploid-enriched counterparts (FIG. 3G). Moreover, methylome analysis showed that the X chromosome DNA methylation signature of haploid ES cells resembles that of diploid male ES cells ($X_aY$), whose single-copy X chromosome is largely hypomethylated, as opposed to the composite pattern of a hypomethylated $X_a$ and a hypermethylated $X_i$ in diploid female cells (FIG. 3H). Interestingly, recently diploidized ES cells remained $X_aX_a$ soon after diploidization (within 3 passages after haploid cell enrichment) by all the above-mentioned assays (FIG. 3A, FIGS. 3E-H).

Normalization to total gene expression, which is inherent to conventional relative gene expression analyses,[21] resulted in seemingly similar expression levels of autosomal genes but higher levels of X-linked genes in haploid compared with diploid ES cells (FIG. 3E, FIG. 9C). However, assuming that the absolute expression of X-linked genes in haploid $X_a$ and diploid $X_aX_i$ cells are equivalent, these data suggest a genome-wide autosomal gene level reduction in haploid cells (FIG. 9E, FIG. 9F). In support of this notion, we found that total RNA amounts isolated from haploid ES cells were significantly lower than those obtained from the same numbers of diploid cells (FIG. 3I). An overall decrease in total gene expression implied that the physical dimensions of these cells may also be altered. Indeed, the average diameter ratio between sorted haploid and diploid ES cells in G1 was around 0.8 (9.6 and 11.5 µm, respectively), corresponding to haploid:diploid ratios of around 0.7 in surface area and around 0.6 in volume (FIG. 3I, FIG. 9G).

We subsequently focused on consistent differential regulation within autosomes. Based on transcriptional and DNA methylation analyses, we found significant enrichment of genes encoding proteins with signal peptides to be relatively downregulated in haploid ES cells (FIG. 9H). Remarkably, we also detected subtle yet significant relative upregulation of 11 genes involved in oxidative phosphorylation in haploid cells, including representatives encoding subunits of four out of the five complexes comprising this pathway (FIG. 3J, FIG. 9I). Furthermore, all 13 mitochondrial genes involved in oxidative phosphorylation were consistently upregulated in haploid cells as well (FIG. 3J), indicating coordinated regulation between these nuclear and mitochondrial genes. This coincides with a 32% increase in the mitochondrial DNA (mtDNA) to nuclear DNA ratio between haploids and diploids (FIG. 3I), suggesting that mitochondrial abundance relative to the nuclear DNA content is relatively higher in haploid cells.

Example 5. Differentiation of Human Haploid ES Cells

We next sought to assess the differentiation potential of haploid human ES cells of parthenogenetic origin. Although mammalian parthenogenetic development is restricted due to the non-equivalence of parental genomes,[22,23] diploid human parthenogenetic pluripotent stem cells are functionally pluripotent as evident by their ability to give rise to all embryonic lineages.[13,24,25] To address whether human parthenogenetic ES cells are capable of multilineage differentiation as haploids, we performed several differentiation assays, followed by ploidy and differentiation status characterizations of the resulting cells. 21-day-old EBs generated by spontaneous differentiation of haploid-enriched and diploid ES cells could not be distinguished by appearance (FIG. 4A), and the morphology of dissociated haploid-cell-derived EB cells was consistent with differentiation (FIG. 10A). Notably, metaphase spread analysis revealed a haploid karyotype (FIG. 4B; 4/4 metaphases), and a largely haploid DNA profile (~70% haploids) was confirmed by flow cytometry in both h-pES10- and h-pES12-derived EB cells (FIG. 4C, FIG. 10B). We then compared the gene expression profiles of G1-sorted haploid ES and EB cells, focusing on 18 genes that showed clear specificity across eight tissues and pluripotent stem cells. For example, our gene set included CHRM1 (cholinergic receptor), KRT1 7 (keratine), MYL1 (myosin), REN (renin), ALB (albumin), CPA1 (carboxypeptidase), SFTPD (surfactant) and MALRD1 (MAM and LDL receptor), which are expressed in the brain, skin, muscle, kidney, liver, pancreas, lung and intestine, respectively (FIG. 4D). Whereas the expression of these lineage-specific genes was negligible in undifferentiated ES cells, all were expressed in haploid and diploid EB cells (FIG. 4D, FIG. 6C). In addition, haploid and diploid EB cells showed insignificant expression of pluripotency-specific genes, consistent with efficient differentiation and acquisition of somatic cell fates of all three embryonic germ layers.

To extend this analysis to more specific and potentially more mature cell types, we subjected haploid ES cells to directed differentiation assays. Haploid ES cells undergoing directed differentiation towards a neural fate for ten days remained haploid while efficiently giving rise to neural cell adhesion molecule 1 (NCAM1)-positive neural progenitor cells (NPCs, ~90% efficiency) (FIG. 4E, FIG. 11A, FIG. 11B). Sorted haploid NPCs expressed multiple neural-lineage-specific genes but not pluripotency-specific genes (FIG. 4F, FIG. 11C), indicating a robust exit from the pluripotent state while taking on a neural fate. XCI is imperative in diploid differentiated female cells, resulting in dosage compensation and a ratio of 1:2 between the X chromosome and autosomes. Since haploid ES cells are incapable of inactivating their single-copy X chromosome, an X:autosomes dosage imbalance of 1:1 should persist into the differentiated state. Indeed, both haploid NPCs and haploid EB cells showed an $X_a$ signature contrary to the $X_aX_i$ signature of diploid EB cells, as indicated by whole-genome expression analysis and XIST levels (FIG. 4G, FIG. 11D).

Neuronal differentiation was not restricted to the progenitor stage as the cells also differentiated with high efficiency (>90%) into mature TUJ1 (also known as β-tubulin III)-positive neurons by 20 days with notable persistence of haploid cells, as shown by both co-staining with centromeres (FIG. 4H; 47% haploids, n=104) and FISH analysis (FIG. 11E, FIG. 11F; 46% haploids, n=200). Similarly, haploid cells differentiated into cardiac troponin T type 2 (TNNT2)-expressing cardiomyocytes (FIG. 4I; 32% haploids, n=97) during an 11-day protocol resulting in spontaneously beating clusters and 39% (n=31) of haploid cells sorted from the whole culture (25% 1c cells) were confirmed as TNNT2-positive (FIG. 4J, FIG. 11G). Next, we differentiated haploid-enriched cultures (~70% haploids) to the pancreatic lineage, analyzing two stages of differentiation by centromere foci analysis, namely, specification to definitive endoderm and further into pancreatic cells. We observed robust differentiation (>90%) of both haploids and diploids into forkhead box A2 (FOXA2)-positive definitive endoderm cells (FIG. 4K; 56% haploids, n=112), and into pancreatic and duodenal homeobox 1 (PDX1)-positive pancreatic cells (FIG. 4I; 13% haploid, n=103), some of which were also positive for NK6 homeobox 1 (NKX6.1). In addition to centromere analysis, the persistence of haploid PDX1-positive cells was also confirmed by flow cytometry (FIG. 4M; 10% PDX1-positive 1c cells; FIG. 11H, FIG. 11I).

Finally, both haploid-enriched human ES cell lines gave rise to teratomas comprising cell types of ectodermal, mesodermal and endodermal origins as shown by histological and immunostaining analyses with TUJ1, α-smooth muscle actin (α-SMA) and α-fetoprotein (AFP) (FIG. 4N, FIG. 12A, FIG. 12B), meeting the most stringent criterion for human pluripotency in vivo. Importantly, no residual undifferentiated OCT4-positive cells could be detected (FIG. 4N, FIG. 12B). Upon dissection, DNA content analysis revealed that a considerable population of h-pES10-derived teratoma cells remained haploid (FIG. 4O). Combined analysis of serial sections from an independent, h-pES12-derived teratoma, by histology and FISH confirmed the existence of in vivo differentiated haploid human cells able to contribute to an organized tissue structure while responding to developmental signals (FIG. 4P). It is worth noting that haploid cells were identified in all analyzed teratomas (n=4), although with variable proportions, which may be influenced by the initial amount of haploid cells and/or the time length of differentiation.

Example 6. Differentiation of Human Haploid ES Cells

Chemotherapies are a central therapy in cancer. However, resistance to chemotherapies has become a major hurdle in the long term success of chemotherapy. Many different pathways have been suggested to be involved in the establishment of resistance to chemotherapies. The present inventors therefore sought to identify genes that their loss-of-function will enable resistance to major chemotherapy drugs. Thus, the loss-of-function haploid libraries described herein were analyzed for genes whose depletion lead to resistance to chemotherapies. Different chemotherapies affecting embryonic stem cells were identified, and cells from the different libraries were exposed to each of the chemotherapies to allow growth of resistant cells, followed by the identification of the genes underlying the resistance. Such screening will empower a global analysis of resistance to chemotherapy.

As a proof of principle the present inventors have exposed the gene trap library of haploid human ES cells to Bleomycin and isolated DNA from the cells before and after treatment. The DNA was analyzed by high throuput sequencing to identify enrichment for specific genes that their knockout enabled the cells to survive in the presence of Bleomycin. About 20 genes showed significant enrichment, among them are RIF1 and PINX1, two genes involved in DNA damage response and telomerase length (see FIG. 13). The analysis demonstrated the genes and pathways that enable resistance to Bleomycin, and drug combination with the chemotherapy can be devised to overcome the resistance to the drug.

Furthermore, the identification of genes that enable resistance to Bleomycin can assist us in identifying the patients whose tumor will show resistance to the drug. Human tumors may be analyzed for copy number variation and gene expression, and thus for each tumor, it is possible to identify whether a specific gene was deleted in the cancer cells. The present analysis of multiple tumors show that some tumors present deletion and/or absence of expression of RIF1 or PINX1, the two genes that their absence would confer resistance to the drug (FIG. 14).

REFERENCES

1. Leeb, M. & Wutz, A. Derivation of haploid embryonic stem cells from mouse embryos. *Nature* 479, 131-4 (2011).
2. Elling, U. et al. Forward and reverse genetics through derivation of haploid mouse embryonic stem cells. *Cell Stem Cell* 9, 563-74 (2011).
3. Yang, H. et al. Generation of genetically modified mice by oocyte injection of androgenetic haploid embryonic stem cells. *Cell* 149, 605-17 (2012).
4. Li, W. et al. Androgenetic haploid embryonic stem cells produce live transgenic mice. *Nature* 490, 407-11 (2012).
5. Li, W. et al. Genetic modification and screening in rat using haploid embryonic stem cells. *Cell Stem Cell* 14, 404-14 (2014).
6. Yang, H. et al. Generation of haploid embryonic stem cells from *Macaca fascicularis* monkey parthenotes. *Cell Res.* 23, 1187-200 (2013).
7. Wutz, A. Haploid mouse embryonic stem cells: rapid genetic screening and germline transmission. *Annu. Rev. Cell Dev. Biol.* 30, 705-22 (2014).
8. Tarkowski, A. K., Witkowska, A. & Nowicka, J. Experimental partheonogenesis in the mouse. *Nature* 226, 162-5 (1970).
9. Kaufman, M. H., Robertson, E. J., Handyside, A. H. & Evans, M. J. Establishment of pluripotential cell lines from haploid mouse embryos. *J. Embryol. Exp. Morphol.* 73, 249-61 (1983).
10. Egli, D. et al. Impracticality of egg donor recruitment in the absence of compensation. *Cell Stem Cell* 9, 293-4 (2011).
11. Leeb, M. & Wutz, A. Haploid genomes illustrate epigenetic constraints and gene dosage effects in mammals. *Epigenetics Chromatin* 6, 41 (2013).
12. Tesar, P. J. et al. New cell lines from mouse epiblast share defining features with human embryonic stem cells. *Nature* 448, 196-9 (2007).
13. Revazova, E. S. et al. Patient-specific stem cell lines derived from human parthenogenetic blastocysts. *Cloning Stem Cells* 9, 432-49 (2007).
14. Kim, K. et al. Recombination signatures distinguish embryonic stem cells derived by parthenogenesis and somatic cell nuclear transfer. *Cell Stem Cell* 1, 346-52 (2007).
15. Paull, D. et al. Nuclear genome transfer in human oocytes eliminates mitochondrial DNA variants. *Nature* 493, 632-7 (2013).
16. Leeb, M. et al. Germline potential of parthenogenetic haploid mouse embryonic stem cells. *Development* 139, 3301-5 (2012).
17. Takahashi, S. et al. Induction of the G2/M transition stabilizes haploid embryonic stem cells. *Development* 141, 3842-7 (2014).
18. Ben-David, U., Nudel, N. & Benvenisty, N. Immunologic and chemical targeting of the tight-junction protein Claudin-6 eliminates tumorigenic human pluripotent stem cells. *Nat. Commun.* 4, 1992 (2013).
19. Silva, S. S., Rowntree, R. K., Mekhoubad, S. & Lee, J. T. X-chromosome inactivation and epigenetic fluidity in human embryonic stem cells. *Proc. Natl. Acad. Sci. U.S.A* 105, 4820-5 (2008).

20. Bruck, T., Yanuka, O. & Benvenisty, N. Human pluripotent stem cells with distinct X inactivation status show molecular and cellular differences controlled by the X-Linked ELK-1 gene. *Cell Rep.* 4, 262-70 (2013).
21. Lovén, J. et al. Revisiting global gene expression analysis. *Cell* 151, 476-82 (2012).
22. McGrath, J. & Solter, D. Completion of mouse embryogenesis requires both the maternal and paternal genomes. *Cell* 37, 179-83 (1984).
23. Barton, S. C., Surani, M. A. & Norris, M. L. Role of paternal and maternal genomes in mouse development. *Nature* 311, 374-6 (1984).
24. Mai, Q. et al. Derivation of human embryonic stem cell lines from parthenogenetic blastocysts. *Cell Res.* 17, 1008-19 (2007).
25. Stelzer, Y., Yanuka, O. & Benvenisty, N. Global analysis of parental imprinting in human parthenogenetic induced pluripotent stem cells. *Nat. Struct. Mol. Biol.* 18, 735-41 (2011).
26. Minkovsky, A., Patel, S. & Plath, K. Concise review: Pluripotency and the transcriptional inactivation of the female Mammalian X chromosome. *Stem Cells* 30, 48-54 (2012).
27. Biancotti, J. C. et al. The in vitro survival of human monosomies and trisomies as embryonic stem cells. *Stem Cell Res.* 9, 218-24 (2012).
28. Zhou, W. et al. HIF1α induced switch from bivalent to exclusively glycolytic metabolism during ESC-to-EpiSC/hESC transition. *EMBO J.* 31, 2103-16 (2012).
29. Shuai, L. et al. Durable pluripotency and haploidy in epiblast stem cells derived from haploid embryonic stem cells in vitro. *J. Mol. Cell Biol.* 1-29 (2015). doi: 10.1093/jmcb/mjv044
30. Carette, J. E. et al. Haploid genetic screens in human cells identify host factors used by pathogens. *Science* 326, 1231-5 (2009).
31. Carette, J. E. et al. Ebola virus entry requires the cholesterol transporter Niemann-Pick C1. *Nature* 477, 340-3 (2011).
32. Wang, T., Wei, J. J., Sabatini, D. M. & Lander, E. S. Genetic screens in human cells using the CRISPR-Cas9 system. *Science* 343, 80-4 (2014).
33. Shalem, O. et al. Genome-scale CRISPR-Cas9 knockout screening in human cells. *Science* 343, 84-7 (2014).
34. Otto, S. P. & Jarne, P. Evolution. Haploids—hapless or happening? *Science* 292, 2441-3 (2001).
35. Noggle, S. et al. Human oocytes reprogram somatic cells to a pluripotent state. *Nature* 478, 70-5 (2011).
36. Cowan, C. A., Atienza, J., Melton, D. A. & Eggan, K. Nuclear reprogramming of somatic cells after fusion with human embryonic stem cells. *Science* 309, 1369-73 (2005).
37. Johannesson, B. et al. Comparable Frequencies of Coding Mutations and Loss of Imprinting in Human Pluripotent Cells Derived by Nuclear Transfer and Defined Factors. *Cell Stem Cell* 15, 634-642 (2014).
38. Chen, A. E. et al. Optimal timing of inner cell mass isolation increases the efficiency of human embryonic stem cell derivation and allows generation of sibling cell lines. *Cell Stem Cell* 4, 103-6 (2009).
39. Rao, P. H., Nandula, S. V & Murty, V. V. Molecular cytogenetic applications in analysis of the cancer genome. *Methods Mol. Biol.* 383, 165-85 (2007).
40. The Genotype-Tissue Expression (GTEx) project. *Nat. Genet.* 45, 580-5 (2013).
41. Yamada, M. et al. Human oocytes reprogram adult somatic nuclei of a type 1 diabetic to diploid pluripotent stem cells. *Nature* 510, 533-6 (2014).
42. Wanet, A. et al. Mitochondrial remodeling in hepatic differentiation and dedifferentiation. *Int. J. Biochem. Cell Biol.* 54, 174-85 (2014).
43. Kim, D.-S. et al. Robust enhancement of neural differentiation from human ES and iPS cells regardless of their innate difference in differentiation propensity. *Stem Cell Rev.* 6, 270-81 (2010).
44. Stelzer, Y., Sagi, I. & Benvenisty, N. Involvement of parental imprinting in the antisense regulation of oncomiR-372-373. *Nat. Commun.* 4, 2724 (2013).
45. Wang, L. et al. Differentiation of hypothalamic-like neurons from human pluripotent stem cells. *J. Clin. Invest.* 125, 796-808 (2015).
46. Chambers, S. M. et al. Highly efficient neural conversion of human ES and iPS cells by dual inhibition of SMAD signaling. *Nat. Biotechnol.* 27, 275-80 (2009).
47. Lian, X. et al. Directed cardiomyocyte differentiation from human pluripotent stem cells by modulating Wnt/β-catenin signaling under fully defined conditions. *Nat. Protoc.* 8, 162-75 (2013).
48. Hua, H. et al. iPSC-derived β cells model diabetes due to glucokinase deficiency. *J. Clin. Invest.* 123, 3146-53 (2013).
49. Pagliuca, F. W. et al. Generation of functional human pancreatic β cells in vitro. *Cell* 159, 428-39 (2014).
50. Rezania, A. et al. Reversal of diabetes with insulin-producing cells derived in vitro from human pluripotent stem cells. *Nat. Biotechnol.* 32, 1121-33 (2014).
51. Doench, J. G. et al. Optimized sgRNA design to maximize activity and minimize off-target effects of CRISPR-Cas9. *Nat. Biotechnol.* (2016). doi: 10.1038/nbt.3437.
52. Cadiñanos, J. & Bradley, A. Generation of an inducible and optimized piggyBac transposon system. *Nucleic Acids Res.* 35, e87 (2007).
53. Wang, W. et al. Chromosomal transposition of PiggyBac in mouse embryonic stem cells. *Proc. Natl. Acad. Sci. U.S.A* 105, 9290-5 (2008).
54. Chen, L. et al. Transposon activation mutagenesis as a screening tool for identifying resistance to cancer therapeutics. *BMC Cancer* 13, 93 (2013).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of selecting an agent for treating a disease in a subject, the method comprising:
  (a) exposing a plurality of isolated haploid human embryonic stem (ES) cells capable of differentiating into a terminally differentiated haploid cell selected from a haploid mature neuron, haploid mature pancreatic cell and haploid cardiomyocyte or haploid cells differentiated from said isolated haploid human ES cells, to an agent, wherein at least a portion of said plurality of cells comprises a distinct artificially inactivated or overactivated gene;
  (b) selecting a cell of said plurality of cells which shows resistance to said agent;
  (c) identifying in said cell said distinct artificially inactivated or overactivated gene; and
  (d) analyzing the sequence and/or expression of said distinct artificially inactivated gene or activated gene in a cell sample of the subject, wherein an alteration in the sequence and/or level of expression of said distinct gene as compared to the sequence and/or expression of said distinct gene in a control sample is indicative of the agent to be used or ruled out for treating the disease in the subject.

2. The method of claim 1, wherein at least a portion of said plurality of haploid ES cells comprises a distinct artificially inactivated gene and wherein a reduction in expression of said distinct gene in said cell sample indicates the agent should be ruled out as a monotherapy.

3. The method of claim 1, wherein said plurality of cells comprises a gene trap vector, or components of a CRISPR system, which brings about inactivation of said distinct artificially inactivated gene.

4. The method of claim 3, wherein said gene trap vector encodes a reporter polypeptide which identifies said distinct artificially inactivated gene.

5. The method of claim 1, wherein said exposing a plurality of haploid human embryonic stem (ES) cells is effected in a single container or in a plurality of containers, wherein each container of said plurality of containers comprises haploid human ES cells with an identical artificially inactivated gene.

6. The method of claim 1, wherein the disease is cancer; optionally wherein said cell sample is a tumor sample.

7. The method of claim 1, wherein said agent is a cytotoxic therapy and comprises a pharmaceutical agent or radiation therapy.

8. The method of claim 7, wherein said pharmaceutical agent is a chemotherapeutic agent.

9. The method of claim 8, wherein said chemotherapeutic agent is an antibiotic.

10. The method of claim 9, wherein said antibiotic is an anthracycline or a chromomycin.

11. The method of claim 1, wherein said pharmaceutical agent is selected from the group consisting of Doxorubicin, Daunorubicin, Mitoxantrone, Idarubicin, Dactinomycin, Plicamycin, Mitomycin and Bleomycin.

12. The method of claim 11, wherein said pharmaceutical agent is Bleomycin.

13. The method of claim 1, wherein said identifying is effected by sequencing DNA of said cells.

14. The method of claim 1, wherein said haploid human ES cells are generated by:
 (a) identifying haploid metaphase cells in a sample from a population of ES cells, wherein the ES cells are derived from an artificially activated human oocyte; and
 (b) sorting the population of ES cells based on cell ploidy to produce a population of haploid human ES cells.

15. The method of claim 14, further comprising maintaining the enriched population of ES cells in culture for at least three passages.

16. The method of claim 14, wherein the haploid metaphase cells in the sample are identified by flow cytometry, centromere protein immunofluorescence staining, metaphase spread analysis, sub-2c cell sorting or DNA fluorescence in situ hybridization.

17. The method of claim 14, wherein the sorting step comprises at least one cycle of fluorescence-activated cell sorting (FACS).

18. The method of claim 14, wherein said haploid cells differentiated from isolated haploid human ES cells are multipotent cells or terminally differentiated cells.

19. The method of claim 1, wherein said cell sample of the subject in step (d) is obtained before a therapeutic treatment of said subject with said agent.

* * * * *